(12) United States Patent
Linsley et al.

(10) Patent No.: US 7,105,166 B1
(45) Date of Patent: *Sep. 12, 2006

(54) SOLUBLE CTLA4 MUTANT MOLECULES AND USES THEREOF

(75) Inventors: Peter S. Linsley, Seattle, WA (US); Jeffrey A. Ledbetter, Seattle, WA (US); Jurgen Bajorath, Lynnwood, WA (US); Robert J. Peach, San Diego, CA (US); William Brady, Bothell, WA (US); Philip Wallace, Seattle, WA (US); Nitin Damle, Upper Saddle River, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 646 days.

This patent is subject to a terminal disclaimer.

(21) Appl. No.: 09/609,915

(22) Filed: Jul. 3, 2000
(Under 37 CFR 1.47)

Related U.S. Application Data

(63) Continuation-in-part of application No. 08/228,208, filed on Apr. 15, 1994, now Pat. No. 6,090,914, which is a continuation-in-part of application No. 08/008,898, filed on Jan. 22, 1993, now Pat. No. 5,770,197, which is a continuation-in-part of application No. 07/723,617, filed on Jun. 27, 1991, now abandoned.

(51) Int. Cl.
*C07K 16/46* (2006.01)
*C07K 14/705* (2006.01)
*C07K 14/725* (2006.01)

(52) U.S. Cl. ............... 424/192.1; 530/387.3; 530/350; 435/69.7; 424/134.1

(58) Field of Classification Search ............ 435/69.5, 435/69.7; 536/23.1; 530/350, 403; 424/192.1
See application file for complete search history.

(56) References Cited

U.S. PATENT DOCUMENTS

| | | | |
|---|---|---|---|
| 5,434,131 A * | 7/1995 | Linsley et al. ............. 514/2 |
| 5,637,481 A | 6/1997 | Ledbetter et al. |
| 5,770,197 A | 6/1998 | Linsley et al. |
| 5,773,253 A * | 6/1998 | Linsley et al. ............. 435/69.7 |
| 5,844,095 A * | 12/1998 | Linsley et al. ............. 530/387.3 |
| 5,851,795 A * | 12/1998 | Linsley et al. ............. 435/69.1 |
| 5,885,579 A | 3/1999 | Linsley et al. |
| 5,885,796 A * | 3/1999 | Linsley et al. ............. 435/69.1 |
| 5,916,560 A | 6/1999 | Larsen et al. |
| 5,958,403 A | 9/1999 | Strom et al. |
| 5,968,510 A | 10/1999 | Linsley et al. |
| 5,977,318 A | 11/1999 | Linsley et al. |
| 5,993,800 A | 11/1999 | Linsley et al. |
| 6,090,914 A * | 7/2000 | Linsley et al. ............. 530/350 |
| 6,132,992 A | 10/2000 | Ledbetter et al. |
| 6,444,792 B1 | 9/2002 | Gray et al. |

FOREIGN PATENT DOCUMENTS

| | | |
|---|---|---|
| EP | 0 613 944 A2 | 9/1994 |
| EP | 0 682 039 A1 | 11/1995 |
| WO | WO 93/19767 | 10/1993 |
| WO | WO 94/28912 | 12/1994 |
| WO | WO 94/29436 | 12/1994 |
| WO | WO 95/33823 | 12/1995 |
| WO | WO 96/14865 | 5/1996 |
| WO | WO 98/31820 | 7/1998 |
| WO | WO 98/33513 | 8/1998 |
| WO | WO 98/56417 | 12/1998 |
| WO | WO 00/23115 | 4/2000 |
| WO | WO 01/54732 A1 | 8/2001 |
| WO | WO 01/90122 A2 | 11/2001 |
| WO | WO 01/92337 | 12/2001 |
| WO | WO 02/02638 | 1/2002 |

OTHER PUBLICATIONS

Peach et al., "Complementarity Determining Region 1 (CDR1)- and CDR3-analogous in CTLA-4 and CD28 Determine the Binding to B7-1," (1994) J. Exp. Med. 180:2049-2058. (Exhibit 236).

Morton et al., "Differential Effects of CTLA-4 Substitutions on the Binding of Human CD80 (B7-1) and CD86 (B7-2)," (1996) J. Immol.Feb. 1; 156:1047-1054. (Exhibit 237).

Sun, Hong et al., "Prevention of Chronic Rejection in Mouse Aortic Allografts by Combined Treatment with CTLA4-Ig and Anti-CD40 Ligand Monoclonal Antibody," Transplantation, 1997, 64:1838-56 (Exhibit 239).

Souza, "Synergistic inhibition of established collagen induced arthritis (CIA) through dual inhibition of ICAM-1 and CD40L pathways," Arthritis and Rhuematism, 1999, p. S60; abstract 64 (Exhibit 240).

Blazar, Bruce R. et al., "Coblockade of the LFAI:ICAM and CD28/CTLA4:B7 Pathways Is A Highly Effective Means of Preventing Acute Lethal Graft-Versus-Host Disease Induced by Fully Major Histocompatibility Complex-Disparate Donor Grafts," Blood, 1995, 85:2607-18 (Exhibit 241).

Alegre et al., "Immunomudulation of transplant rejection using monoclonal antibodies and soluble receptors," Dig. Dis. Sci., 1995, 40:58-64 (Exhibit 244).

Murakami et al., "Identification and characterization of an alternative cytotoxic T lymphocyte-associated protein 4 binding molecule on B cells," Proc. Nat. Acad. Sci. USA, 1996, 3:7838-7842 (Exhibit 245).

(Continued)

Primary Examiner—Lorraine Spector
(74) Attorney, Agent, or Firm—Audrey Sher

(57) ABSTRACT

The present invention provides soluble CTLA4 mutant molecules which bind CD80 and/or CD86 antigen.

12 Claims, 36 Drawing Sheets

OTHER PUBLICATIONS

Peach et al., "Both extracellaular immunoglobulin-like domains of CD80 contain residues critical for binding T cell surface receptors CTLA-4 and CD28," *J. Biol. Chem.*, 1995, 270):21181-21187 (Exhibit 246).

Fargeas et al., "Identification of Residues in the V Domain of CD80 (B7-1) Implicated in Functional Interactions with CD28 and CTLA4," *J. Exp. Med.*, 1995, 182:667-675 (Exhibit 247).

Steurer et al., "Ex Vivo Coating of Islet Cell Allografts with Murin CTLA4/Fc Promotes Graft Tolerance," *J. Immunol.*, 1995, 155:1165-1174 (Exhibit 248).

Guo et al., "Mutational Analysis and an Alternatively Spliced Product of B7 Defines Its CD28/CTLA4-binding Site on Immunoglobulin C-like Domain," *J. Exp. Med.*, 1995, 181:1345-1355 (Exhibit 249).

Peach et al., "CTLA4Ig: A Novel Immunoglobulin Chimera with Immunosuppressive Properties," *Methods*, 1995, 8:116-123 (Exhibit 250).

Rattis et al., "Expression and function of B7-1 (CD80) and B7-2 (CD86) on human epidermal Langerhans cells," *Eur. J. Immunol.*, 1996, 26:449-453 (Exhibit 251).

Najafian, et al., "CTLA4-Ig: a novel immunosuppressive agent," *Exp. Opin. Invest. Drugs*, 2000, 9:2147-2157 (Exhibit 255).

Schwartz, R., "Costimulation of T Lymphocytes: The Role of CD28, CTLA-4, and B7/BB1 in Interleukin-2 Production and Immunotherapy," *Cell*, 1992, 71:1085-1088. (Exhibit 257).

Fanslow, William C. et al., "Regulation of Alloreactivity In Vivo by IL-4 and the Soluble IL-4 Receptor" *The Journal of Immunology*, 1991, 147:535-40 (Exhibit 69).

Brummell, David A. et al., "Probing the Combining Site of an Anti-Carbohydrate Antibody by Saturation-Mutagenesis: Role of the Heavy-Chain CDR3 Residues" *Biochemistry*, 1993, 32:1180-1187. (Exhibit 260).

Weissenhorn, Winifred et al., "VH-Related Idiotopes Detected By Site-Directed Mutagenesis, A Study Induced by the Failure to find CD4 Anti-Idiotypic antibodies Mimicking the cellular receptor of HIV1," *Journal of Immunology*, 1992, 149: 1237-1241 (Exhibit 261).

Aruffo, Alenjandro and Brian Seed, "Molecular Cloning of a CD28 cDNA by a High-Efficiency COS Cell Expression System," PNAS, Dec. 1987, 84:8573-7. (Exhibit 262).

\* cited by examiner

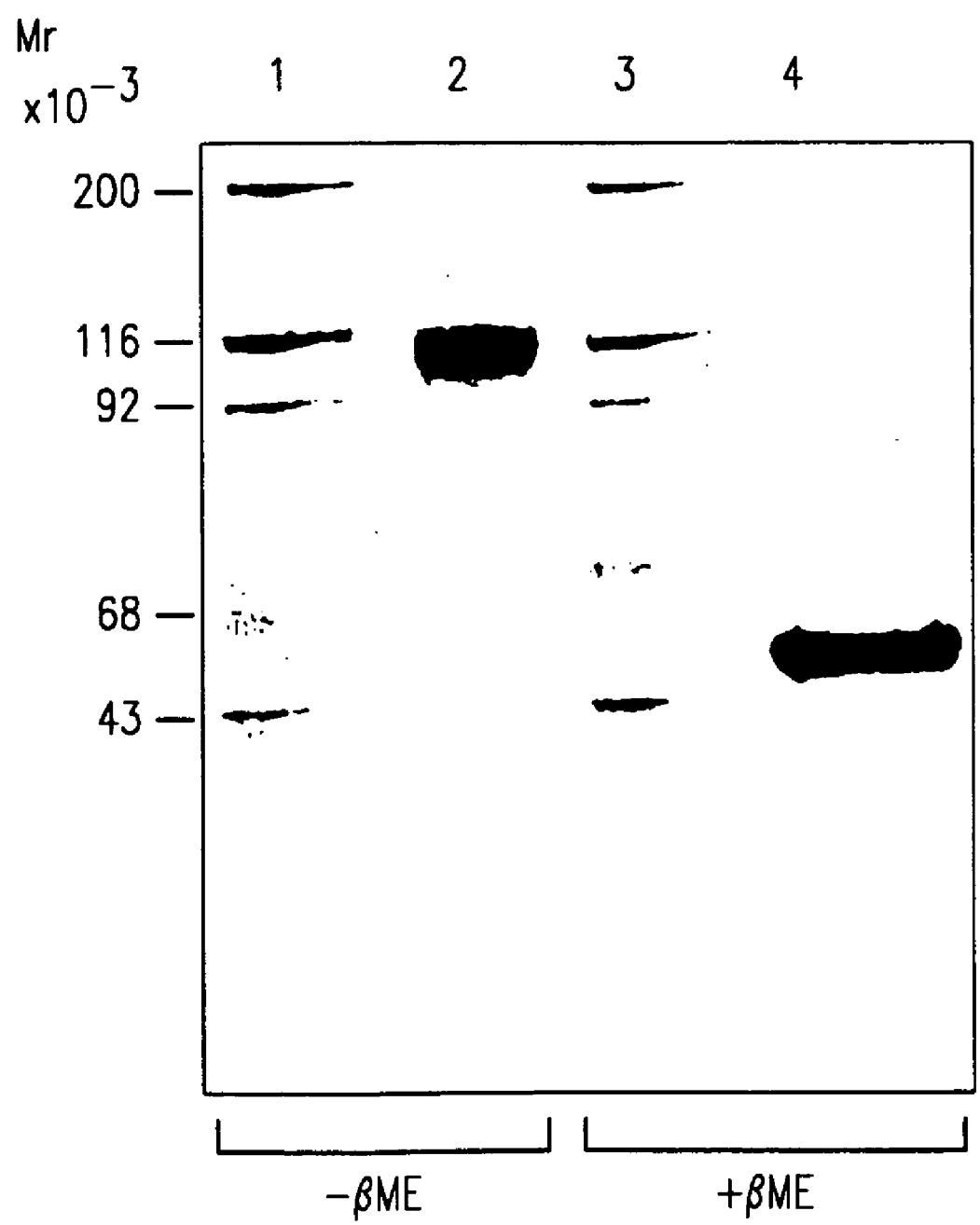

FIG. 3

```
-26
 M   G   V   L   L   T   Q   R   T   L   L   S   L   V   L
ATG GGT GTA CTG CTC ACA CAG AGG ACG CTG CTC AGT CTG GTC CTT    45

-1  +1→
 A   L   L   F   P   S   M   A   S   M   A   M   H   V   A
GCA CTC CTG TTT CCA AGC ATG GCG AGC ATG GCA ATG CAG GTG GCC    90

+10
 Q   P   A   V   V   L   A   S   S   R   G   I   A   S   F
CAG CCT GCT GTG GTA CTG GCC AGC AGC CGA GGC ATC GCC AGC TTT   135

+20                              +30
 V   C   E   Y   A   S   P   G   K   A   T   E   V   R   V
GTG TGT GAG TAT GCA TCT CCA GGC AAA GCC ACT GAG GTC CGG GTG   180

+40
 T   V   L   R   Q   A   D   S   Q   V   T   E   V   C   A
ACA GTG CTT CGG CAG GCT GAC AGC CAG GTG ACT GAA GTC TGT GCG   225

+50                                          +60
 A   T   Y   M   M   G   N   E   L   T   F   L   D   D   S
GCA ACC TAC ATG ATG GGG AAT GAG TTG ACC TTC CTA GAT GAT TCC   270

+70
 I   C   T   G   T   S   S   G   N   Q   V   N   L   T   I
ATC TGC ACG GGC ACC TCC AGT GGA AAT CAA GTG AAC CTC ACT ATC   315

+80                                      +90
 Q   G   L   R   A   M   D   T   G   L   Y   I   C   K   V
CAA GGA CTG AGG GCC ATG GAC ACG GGA CTC TAC ATC TGC AAG GTG   360

GLYCOSYLATION SITE
                  +100                                   ⌐
 E   L   M   Y   P   P   P   Y   Y   L   G   I   G   N   G
GAG CTC ATG TAC CCA CCG CCA TAC TAC CTG GGC ATA GGC AAC GGA   405

+110                             +120
 T   Q   I   Y   V   I   D   P   E   P   C   P   D   S   D
ACC CAG ATT TAT GTG ATT GAT CCA GAA CCG TGC CCA GAT TCT GAC   450

+130
 F   L   L   W   I   L   A   A   V   S   S   G   L   F   F
TTC CTC CTC TGG ATC CTT GCA GCA GTT AGT TCG GGG TTG TTT TTT   495

+140                                     +150
 Y   S   F   L   L   T   A   V   S   L   S   K   M   L   K
TAT AGC TTT CTC CTC ACA GCT GTT TCT TTG AGC AAA ATG CTA AAG   540

+160
 K   R   S   P   L   T   T   G   V   Y   V   K   M   P   P
AAA AGA AGC CCT CTT ACA ACA GGG GTC TAT GTG AAA ATG CCC CCA   585

+170                                     +180
 T   E   P   E   C   E   K   Q   F   Q   P   Y   F   I   P
ACA GAG CCA GAA TGT GAA AAG CAA TTT CAG CCT TAT TTT ATT CCC   630

I   N
ATC AAT                                                       636
```

```
Hctla4   K R S P L T T G V Y V K M P T E . E C E . . K Q F Q P Y F I P I N . . F . A . . . . . P
Muctla4  K R S P L T T G V Y V K M P T E . E C E . . K Q F Q P Y F I P I N . . F . A . . . . . Q
Mcd28    R R N N L L Q V Y V N M T P R R P G L T . . K H H Y Q P Y A P A R D F A A Y R P . . . W
Rcd28    R R N N L L H S D Y M N M T P R R P G P T . . K H H Y Q P Y A P A R D F A A Y R S . . .
Hcd28    K R S L L H S D Y M N M T P R R P G P T R . K H Y Q P Y A P P R D F A A Y R S . . .
Chcd28   K R N N Y R Q T H M N H P R H P H Q K N K G Y P S A P T R D Y T A Y R S W Q P
```

|  | | % B7 BINDING ACTIVITY |
|---|---|---|
| CTLA4Ig | C ──── CKVELMYPPPY ──── | 100 |
| CD28Ig | C ──── C ──── C ──── | <0.1 |
| H S1 | C ──── C ──── C ──── | <0.1 |
| H S2 | C ──── C ──── C ──── | 27 |
| H S3 | C ──── C ──── C ──── | <0.1 |
| H S4 | C ──── C ──── C ──── | 16 |
| H S5 | C ──── C ──── C ──── | <0.1 |
| H S6 | C ──── C ──── C ──── | 20 |
| H S4-34 | C ──── C ──── C ──── | 5 |
| H S4-43 | C ──── C ──── C ──── | 2 |
| H S7 | C ──── C ──── C ──── | 44 |
| H S8 | C ──── C ──── C ──── | 56 |
| H S9 | C ──── C ──── C ──── | 5 |

FIG. 19

```
ATGGGTGTACTGCTCACACAGAGGACGCTGCTCAGTCTGGTCCTTGCACTCCTGTTTCCA                -19
M~~G~~V~~L~~L~~T~~Q~~R~~T~~L~~L~~S~~L~~V~~L~~A~~L~~L~~F~~P~~                -7

AGCATGGCGAGCATGGCAATGCACGTGGCCCAGCCTGCTGTGGTACTGGCCAGCAGCCGA                +42
S~~M~~A~~S~~M~~A~~M~~H~~V~~A~~Q~~P~~A~~V~~V~~L~~A~~S~~S~~R~~                +14
                          +1

GGCATCGCCAGCTTTGTGTGTGAGTATGCATCTCCAGGCAAAGCCACTGAGGTCCGGGTG                +102
G~~I~~A~~S~~F~~V~~C~~E~~Y~~A~~S~~P~~G~~K~~A~~T~~E~~V~~R~~V~~                +34

ACAGTGCTTCGGCAGGCTGACAGCCAGGTGACTGAAGTCTGTGCGGCAACCTACATGATG                +162
T~~V~~L~~R~~Q~~A~~D~~S~~Q~~V~~T~~E~~V~~C~~A~~A~~T~~Y~~M~~M~~                +54

GGGAATGAGTTGACCTTCCTAGATGATTCCATCTGCACGGGCACCTCCAGTGGAAATCAA                +222
G~~N~~E~~L~~T~~F~~L~~D~~D~~S~~I~~C~~T~~G~~T~~S~~S~~G~~N~~Q~~                +74

GTGAACCTCACTATCCAAGGACTGAGGGCCATGGACACGGGACTCTACATCTGCAAGGTG                +282
V~~N~~L~~T~~I~~Q~~G~~L~~R~~A~~M~~D~~T~~G~~L~~Y~~I~~C~~K~~V~~                +94

GAGCTCATGTACCCACCGCCATACTACCTGGGCATAGGCAACGGAACCCAGATTTATGTA                +342
E~~L~~M~~Y~~P~~P~~P~~Y~~Y~~L~~G~~I~~G~~N~~G~~T~~Q~~I~~Y~~V~~                +114

ATTGATCCAGAACCGTGCCCAGATTCTGATCAGGAGCCCAAATCTTCTGACAAAACTCAC                +402
I~~D~~P~~E~~P~~C~~P~~D~~S~~D~~Q~~E~~P~~K~~S~~S~~D~~K~~T~~H~~                +134

ACATCCCCACCGTCCCCAGCACCTGAACTCCTGGGTGGATCGTCAGTCTTCCTCTTCCCC                +462
T~~S~~P~~P~~S~~P~~A~~P~~E~~L~~L~~G~~G~~S~~S~~V~~F~~L~~F~~P~~                +154

CCAAAACCCAAGGACACCCTCATGATCTCCCGGACCCCTGAGGTCACATGCGTGGTGGTG                +522
P~~K~~P~~K~~D~~T~~L~~M~~I~~S~~R~~T~~P~~E~~V~~T~~C~~V~~V~~V~~                +174

GACGTGAGCCACGAAGACCCTGAGGTCAAGTTCAACTGGTACGTGGACGGCGTGGAGGTG                +582
D~~V~~S~~H~~E~~D~~P~~E~~V~~K~~F~~N~~W~~Y~~V~~D~~G~~V~~E~~V~~                +194

CATAATGCCAAGACAAAGCCGCGGGAGGAGCAGTACAACAGCACGTACCGGGTGGTCAGC                +642
H~~N~~A~~K~~T~~K~~P~~R~~E~~E~~Q~~Y~~N~~S~~T~~Y~~R~~V~~V~~S~~                +214

GTCCTCACCGTCCTGCACCAGGACTGGCTGAATGGCAAGGAGTACAAGTGCAAGGTCTCC                +702
V~~L~~T~~V~~L~~H~~Q~~D~~W~~L~~N~~G~~K~~E~~Y~~K~~C~~K~~V~~S~~                +234

AACAAAGCCCTCCCAGCCCCCATCGAGAAAACCATCTCCAAAGCCAAAGGGCAGCCCCGA                +762
N~~K~~A~~L~~P~~A~~P~~I~~E~~K~~T~~I~~S~~K~~A~~K~~G~~Q~~P~~R~~                +254

GAACCACAGGTGTACACCCTGCCCCCATCCCGGGATGAGCTGACCAAGAACCAGGTCAGC                +822
E~~P~~Q~~V~~Y~~T~~L~~P~~P~~S~~R~~D~~E~~L~~T~~K~~N~~Q~~V~~S~~                +274

CTGACCTGCCTGGTCAAAGGCTTCTATCCCAGCGACATCGCCGTGGAGTGGGAGAGCAAT                +882
L~~T~~C~~L~~V~~K~~G~~F~~Y~~P~~S~~D~~I~~A~~V~~E~~W~~E~~S~~N~~                +294

GGGCAGCCGGAGAACAACTACAAGACCACGCCTCCCGTGCTGGACTCCGACGGCTCCTTC                +942
G~~Q~~P~~E~~N~~N~~Y~~K~~T~~T~~P~~P~~V~~L~~D~~S~~D~~G~~S~~F~~                +314

TTCCTCTACAGCAAGCTCACCGTGGACAAGAGCAGGTGGCAGCAGGGGAACGTCTTCTCA                +1002
F~~L~~Y~~S~~K~~L~~T~~V~~D~~K~~S~~R~~W~~Q~~Q~~G~~N~~V~~F~~S~~                +334

TGCTCCGTGATGCATGAGGCTCTGCACAACCACTACACGCAGAAGAGCCTCTCCCTGTCT                +1062
C~~S~~V~~M~~H~~E~~A~~L~~H~~N~~H~~Y~~T~~Q~~K~~S~~L~~S~~L~~S~~                +354

CCGGGTAAATGA
P~~G~~K~~*
```

FIGURE 22

```
ATGGGTGTACTGCTCACACAGAGGACGCTGCTCAGTCTGGTCCTTGCACTCCTGTTTCCA           -19
M~~G~~V~~L~~L~~T~~Q~~R~~T~~L~~L~~S~~L~~V~~L~~A~~L~~L~~F~~P~~          -7

AGCATGGCGAGCATGGCAATGCACGTGGCCCAGCCTGCTGTGGTACTGGCCAGCAGCCGA           +42
S~~M~~A~~S~~M~~A~~M~~H~~V~~A~~Q~~P~~A~~V~~V~~L~~A~~S~~S~~R~~          +14
              +1

GGCATCGCTAGCTTTGTGTGTGAGTATGCATCTCCAGGCAAAGCCACTGAGGTCCGGGTG          +102
G~~I~~A~~S~~F~~V~~C~~E~~Y~~A~~S~~P~~G~~K~~A~~T~~E~~V~~R~~V~~          +34

ACAGTGCTTCGGCAGGCTGACAGCCAGGTGACTGAAGTCTGTGCGGCAACCTACATGATG          +162
T~~V~~L~~R~~Q~~A~~D~~S~~Q~~V~~T~~E~~V~~C~~A~~A~~T~~Y~~M~~M~~          +54

GGGAATGAGTTGACCTTCCTAGATGATTCCATCTGCACGGGCACCTCCAGTGGAAATCAA          +222
G~~N~~E~~L~~T~~F~~L~~D~~D~~S~~I~~C~~T~~G~~T~~S~~S~~G~~N~~Q~~          +74

GTGAACCTCACTATCCAAGGACTGAGGGCCATGGACACGGGACTCTACATCTGCAAGGTG          +282
V~~N~~L~~T~~I~~Q~~G~~L~~R~~A~~M~~D~~T~~G~~L~~Y~~I~~C~~K~~V~~          +94

GAGCTCATGTACCCACCGCCATACTACGAGGGCATAGGCAACGGAACCCAGATTTATGTA          +342
E~~L~~M~~Y~~P~~P~~P~~Y~~Y~~E~~G~~I~~G~~N~~G~~T~~Q~~I~~Y~~V~~         +114

ATTGATCCAGAACCGTGCCCAGATTCTGATCAGGAGCCCAAATCTTCTGACAAAACTCAC          +402
I~~D~~P~~E~~P~~C~~P~~D~~S~~D~~Q~~E~~P~~K~~S~~S~~D~~K~~T~~H~~         +134

ACATCCCCACCGTCCCCAGCACCTGAACTCCTGGGGGGATCGTCAGTCTTCCTCTTCCCC          +462
T~~S~~P~~P~~S~~P~~A~~P~~E~~L~~L~~G~~G~~S~~S~~V~~F~~L~~F~~P~~         +154

CCAAAACCCAAGGACACCCTCATGATCTCCCGGACCCCTGAGGTCACATGCGTGGTGGTG          +522
P~~K~~P~~K~~D~~T~~L~~M~~I~~S~~R~~T~~P~~E~~V~~T~~C~~V~~V~~V~~         +174

GACGTGAGCCACGAAGACCCTGAGGTCAAGTTCAACTGGTACGTGGACGGCGTGGAGGTG          +582
D~~V~~S~~H~~E~~D~~P~~E~~V~~K~~F~~N~~W~~Y~~V~~D~~G~~V~~E~~V~~         +194

CATAATGCCAAGACAAAGCCGCGGGAGGAGCAGTACAACAGCACGTACCGTGTGGTCAGC          +642
H~~N~~A~~K~~T~~K~~P~~R~~E~~E~~Q~~Y~~N~~S~~T~~Y~~R~~V~~V~~S~~         +214

GTCCTCACCGTCCTGCACCAGGACTGGCTGAATGGCAAGGAGTACAAGTGCAAGGTCTCC          +702
V~~L~~T~~V~~L~~H~~Q~~D~~W~~L~~N~~G~~K~~E~~Y~~K~~C~~K~~V~~S~~         +234

AACAAAGCCCTCCCAGCCCCCATCGAGAAAACCATCTCCAAAGCCAAAGGGCAGCCCCGA          +762
N~~K~~A~~L~~P~~A~~P~~I~~E~~K~~T~~I~~S~~K~~A~~K~~G~~Q~~P~~R~~         +254

GAACCACAGGTGTACACCCTGCCCCCATCCCGGGATGAGCTGACCAAGAACCAGGTCAGC          +822
E~~P~~Q~~V~~Y~~T~~L~~P~~P~~S~~R~~D~~E~~L~~T~~K~~N~~Q~~V~~S~~         +274

CTGACCTGCCTGGTCAAAGGCTTCTATCCCAGCGACATCGCCGTGGAGTGGGAGAGCAAT          +882
L~~T~~C~~L~~V~~K~~G~~F~~Y~~P~~S~~D~~I~~A~~V~~E~~W~~E~~S~~N~~         +294

GGGCAGCCGGAGAACAACTACAAGACCACGCCTCCCGTGCTGGACTCCGACGGCTCCTTC          +942
G~~Q~~P~~E~~N~~N~~Y~~K~~T~~T~~P~~P~~V~~L~~D~~S~~D~~G~~S~~F~~         +314

TTCCTCTACAGCAAGCTCACCGTGGACAAGAGCAGGTGGCAGCAGGGGAACGTCTTCTCA         +1002
F~~L~~Y~~S~~K~~L~~T~~V~~D~~K~~S~~R~~W~~Q~~Q~~G~~N~~V~~F~~S~~         +334

TGCTCCGTGATGCATGAGGCTCTGCACAACCACTACACGCAGAAGAGCCTCTCCCTGTCT         +1062
C~~S~~V~~M~~H~~E~~A~~L~~H~~N~~H~~Y~~T~~Q~~K~~S~~L~~S~~L~~S~~         +354

CCGGGTAAATGA
P~~G~~K~~*
```

FIGURE 23

```
ATGGGTGTACTGCTCACACAGAGGACGCTGCTCAGTCTGGTCCTTGCACTCCTGTTTCCA            -19
M~~G~~V~~L~~L~~T~~Q~~R~~T~~L~~L~~S~~L~~V~~L~~A~~L~~L~~F~~P~~            -7

AGCATGGCGAGCATGGCAATGCACGTGGCCCAGCCTGCTGTGGTACTGGCCAGCAGCCGA            +42
S~~M~~A~~S~~M~~A~~M~~H~~V~~A~~Q~~P~~A~~V~~V~~L~~A~~S~~S~~R~~            +14
                 +1

GGCATCGCTAGCTTTGTGTGTGAGTATGCATCTCCAGGCAAATATACTGAGGTCCGGGTG            +102
G~~I~~A~~S~~F~~V~~C~~E~~Y~~A~~S~~P~~G~~K~~Y~~T~~E~~V~~R~~V~~            +34

ACAGTGCTTCGGCAGGCTGACAGCCAGGTGACTGAAGTCTGTGCGGCAACCTACATGATG            +162
T~~V~~L~~R~~Q~~A~~D~~S~~Q~~V~~T~~E~~V~~C~~A~~A~~T~~Y~~M~~M~~            +54

GGGAATGAGTTGACCTTCCTAGATGATTCCATCTGCACGGGCACCTCCAGTGGAAATCAA            +222
G~~N~~E~~L~~T~~F~~L~~D~~D~~S~~I~~C~~T~~G~~T~~S~~S~~G~~N~~Q~~            +74

GTGAACCTCACTATCCAAGGACTGAGGGCCATGGACACGGGACTCTACATCTGCAAGGTG            +282
V~~N~~L~~T~~I~~Q~~G~~L~~R~~A~~M~~D~~T~~G~~L~~Y~~I~~C~~K~~V~~            +94

GAGCTCATGTACCCACCGCCATACTACGAGGGCATAGGCAACGGAACCCAGATTTATGTA            +342
E~~L~~M~~Y~~P~~P~~P~~Y~~Y~~E~~G~~I~~G~~N~~G~~T~~Q~~I~~Y~~V~~            +114

ATTGATCCAGAACCGTGCCCAGATTCTGATCAGGAGCCCAAATCTTCTGACAAAACTCAC            +402
I~~D~~P~~E~~P~~C~~P~~D~~S~~D~~Q~~E~~P~~K~~S~~S~~D~~K~~T~~H~~            +134

ACATCCCCACCGTCCCCAGCACCTGAACTCCTGGGGGGATCGTCAGTCTTCCTCTTCCCC            +462
T~~S~~P~~P~~S~~P~~A~~P~~E~~L~~L~~G~~G~~S~~S~~V~~F~~L~~F~~P~~            +154

CCAAAACCCAAGGACACCCTCATGATCTCCCGGACCCCTGAGGTCACATGCGTGGTGGTG            +522
P~~K~~P~~K~~D~~T~~L~~M~~I~~S~~R~~T~~P~~E~~V~~T~~C~~V~~V~~V~~            +174

GACGTGAGCCACGAAGACCCTGAGGTCAAGTTCAACTGGTACGTGGACGGCGTGGAGGTG            +582
D~~V~~S~~H~~E~~D~~P~~E~~V~~K~~F~~N~~W~~Y~~V~~D~~G~~V~~E~~V~~            +194

CATAATGCCAAGACAAAGCCGCGGGAGGAGCAGTACAACAGCACGTACCGTGTGGTCAGC            +642
H~~N~~A~~K~~T~~K~~P~~R~~E~~E~~Q~~Y~~N~~S~~T~~Y~~R~~V~~V~~S~~            +214

GTCCTCACCGTCCTGCACCAGGACTGGCTGAATGGCAAGGAGTACAAGTGCAAGGTCTCC            +702
V~~L~~T~~V~~L~~H~~Q~~D~~W~~L~~N~~G~~K~~E~~Y~~K~~C~~K~~V~~S~~            +234

AACAAAGCCCTCCCAGCCCCCATCGAGAAAACCATCTCCAAAGCCAAAGGGCAGCCCCGA            +762
N~~K~~A~~L~~P~~A~~P~~I~~E~~K~~T~~I~~S~~K~~A~~K~~G~~Q~~P~~R~~            +254

GAACCACAGGTGTACACCCTGCCCCCATCCCGGGATGAGCTGACCAAGAACCAGGTCAGC            +822
E~~P~~Q~~V~~Y~~T~~L~~P~~P~~S~~R~~D~~E~~L~~T~~K~~N~~Q~~V~~S~~            +274

CTGACCTGCCTGGTCAAAGGCTTCTATCCCAGCGACATCGCCGTGGAGTGGGAGAGCAAT            +882
L~~T~~C~~L~~V~~K~~G~~F~~Y~~P~~S~~D~~I~~A~~V~~E~~W~~E~~S~~N~~            +294

GGGCAGCCGGAGAACAACTACAAGACCACGCCTCCCGTGCTGGACTCCGACGGCTCCTTC            +942
G~~Q~~P~~E~~N~~N~~Y~~K~~T~~T~~P~~P~~V~~L~~D~~S~~D~~G~~S~~F~~            +314

TTCCTCTACAGCAAGCTCACCGTGGACAAGAGCAGGTGGCAGCAGGGGAACGTCTTCTCA            +1002
F~~L~~Y~~S~~K~~L~~T~~V~~D~~K~~S~~R~~W~~Q~~Q~~G~~N~~V~~F~~S~~            +334

TGCTCCGTGATGCATGAGGCTCTGCACAACCACTACACGCAGAAGAGCCTCTCCCTGTCT            +1062
C~~S~~V~~M~~H~~E~~A~~L~~H~~N~~H~~Y~~T~~Q~~K~~S~~L~~S~~L~~S~~            +354

CCGGGTAAATGA
P~~G~~K~~*
```

FIGURE 24

```
ATGGGTGTACTGCTCACACAGAGGACGCTGCTCAGTCTGGTCCTTGCACTCCTGTTTCCA        -19
M~~G~~V~~L~~L~~T~~Q~~R~~T~~L~~L~~S~~L~~V~~L~~A~~L~~L~~F~~P~~         -7

AGCATGGCGAGCATGGCAATGCACGTGGCCCAGCCTGCTGTGGTACTGGCCAGCAGCCGA        +42
S~~M~~A~~S~~M~~A~~M~~H~~V~~A~~Q~~P~~A~~V~~V~~L~~A~~S~~S~~R~~        +14
                    +1

GGCATCGCTAGCTTTGTGTGTGAGTATGCATCTCCAGGCAAATTGACTGAGGTCCGGGTG       +102
G~~I~~A~~S~~F~~V~~C~~E~~Y~~A~~S~~P~~G~~K~~L~~T~~E~~V~~R~~V~~        +34

ACAGTGCTTCGGCAGGCTGACAGCCAGGTGACTGAAGTCTGTGCGGCAACCTACATGATG       +162
T~~V~~L~~R~~Q~~A~~D~~S~~Q~~V~~T~~E~~V~~C~~A~~A~~T~~Y~~M~~M~~        +54

GGGAATGAGTTGACCTTCCTAGATGATTCCATCTGCACGGGCACCTCCAGTGGAAATCAA       +222
G~~N~~E~~L~~T~~F~~L~~D~~D~~S~~I~~C~~T~~G~~T~~S~~S~~G~~N~~Q~~        +74

GTGAACCTCACTATCCAAGGACTGAGGGCCATGGACACGGGACTCTACATCTGCAAGGTG       +282
V~~N~~L~~T~~I~~Q~~G~~L~~R~~A~~M~~D~~T~~G~~L~~Y~~I~~C~~K~~V~~        +94

GAGCTCATGTACCCACCGCCATACTACGAGGGCATAGGCAACGGAACCCAGATTTATGTA       +342
E~~L~~M~~Y~~P~~P~~P~~Y~~Y~~E~~G~~I~~G~~N~~G~~T~~Q~~I~~Y~~V~~       +114

ATTGATCCAGAACCGTGCCCAGATTCTGATCAGGAGCCCAAATCTTCTGACAAAACTCAC       +402
I~~D~~P~~E~~P~~C~~P~~D~~S~~D~~Q~~E~~P~~K~~S~~S~~D~~K~~T~~H~~       +134

ACATCCCCACCGTCCCCAGCACCTGAACTCCTGGGGGGATCGTCAGTCTTCCTCTTCCCC       +462
T~~S~~P~~P~~S~~P~~A~~P~~E~~L~~L~~G~~G~~S~~S~~V~~F~~L~~F~~P~~       +154

CCAAAACCCAAGGACACCCTCATGATCTCCCGGACCCCTGAGGTCACATGCGTGGTGGTG       +522
P~~K~~P~~K~~D~~T~~L~~M~~I~~S~~R~~T~~P~~E~~V~~T~~C~~V~~V~~V~~       +174

GACGTGAGCCACGAAGACCCTGAGGTCAAGTTCAACTGGTACGTGGACGGCGTGGAGGTG       +582
D~~V~~S~~H~~E~~D~~P~~E~~V~~K~~F~~N~~W~~Y~~V~~D~~G~~V~~E~~V~~       +194

CATAATGCCAAGACAAAGCCGCGGGAGGAGCAGTACAACAGCACGTACCGTGTGGTCAGC       +642
H~~N~~A~~K~~T~~K~~P~~R~~E~~E~~Q~~Y~~N~~S~~T~~Y~~R~~V~~V~~S~~       +214

GTCCTCACCGTCCTGCACCAGGACTGGCTGAATGGCAAGGAGTACAAGTGCAAGGTCTCC       +702
V~~L~~T~~V~~L~~H~~Q~~D~~W~~L~~N~~G~~K~~E~~Y~~K~~C~~K~~V~~S~~       +234

AACAAAGCCCTCCCAGCCCCCATCGAGAAAACCATCTCCAAAGCCAAAGGGCAGCCCCGA       +762
N~~K~~A~~L~~P~~A~~P~~I~~E~~K~~T~~I~~S~~K~~A~~K~~G~~Q~~P~~R~~       +254

GAACCACAGGTGTACACCCTGCCCCCATCCCGGGATGAGCTGACCAAGAACCAGGTCAGC       +822
E~~P~~Q~~V~~Y~~T~~L~~P~~P~~S~~R~~D~~E~~L~~T~~K~~N~~Q~~V~~S~~       +274

CTGACCTGCCTGGTCAAAGGCTTCTATCCCAGCGACATCGCCGTGGAGTGGGAGAGCAAT       +882
L~~T~~C~~L~~V~~K~~G~~F~~Y~~P~~S~~D~~I~~A~~V~~E~~W~~E~~S~~N~~       +294

GGGCAGCCGGAGAACAACTACAAGACCACGCCTCCCGTGCTGGACTCCGACGGCTCCTTC       +942
G~~Q~~P~~E~~N~~N~~Y~~K~~T~~T~~P~~P~~V~~L~~D~~S~~D~~G~~S~~F~~       +314

TTCCTCTACAGCAAGCTCACCGTGGACAAGAGCAGGTGGCAGCAGGGGAACGTCTTCTCA      +1002
F~~L~~Y~~S~~K~~L~~T~~V~~D~~K~~S~~R~~W~~Q~~Q~~G~~N~~V~~F~~S~~       +334

TGCTCCGTGATGCATGAGGCTCTGCACAACCACTACACGCAGAAGAGCCTCTCCCTGTCT      +1062
C~~S~~V~~M~~H~~E~~A~~L~~H~~N~~H~~Y~~T~~Q~~K~~S~~L~~S~~L~~S~~       +354

CCGGGTAAATGA
P~~G~~K~~*
```

FIGURE 25

```
ATGGGTGTACTGCTCACACAGAGGACGCTGCTCAGTCTGGTCCTTGCACTCCTGTTTCCA      -19
M~~G~~V~~L~~L~~T~~Q~~R~~T~~L~~L~~S~~L~~V~~L~~A~~L~~L~~F~~P~~       -7

AGCATGGCGAGCATGGCAATGCACGTGGCCCAGCCTGCTGTGGTACTGGCCAGCAGCCGA      +42
S~~M~~A~~S~~M~~A~~M~~H~~V~~A~~Q~~P~~A~~V~~V~~L~~A~~S~~S~~R~~      +14
              +1

GGCATCGCTAGCTTTGTGTGTGAGTATGCATCTCCAGGCAAAACTACTGAGGTCCGGGTG     +102
G~~I~~A~~S~~F~~V~~C~~E~~Y~~A~~S~~P~~G~~K~~T~~T~~E~~V~~R~~V~~      +34

ACAGTGCTTCGGCAGGCTGACAGCCAGGTGACTGAAGTCTGTGCGGCAACCTACATGATG     +162
T~~V~~L~~R~~Q~~A~~D~~S~~Q~~V~~T~~E~~V~~C~~A~~A~~T~~Y~~M~~M~~      +54

GGGAATGAGTTGACCTTCCTAGATGATTCCATCTGCACGGGCACCTCCAGTGGAAATCAA     +222
G~~N~~E~~L~~T~~F~~L~~D~~D~~S~~I~~C~~T~~G~~T~~S~~S~~G~~N~~Q~~      +74

GTGAACCTCACTATCCAAGGACTGAGGGCCATGGACACGGGACTCTACATCTGCAAGGTG     +282
V~~N~~L~~T~~I~~Q~~G~~L~~R~~A~~M~~D~~T~~G~~L~~Y~~I~~C~~K~~V~~      +94

GAGCTCATGTACCCACCGCCATACTACGAGGGCATAGGCAACGGAACCCAGATTTATGTA     +342
E~~L~~M~~Y~~P~~P~~P~~Y~~Y~~E~~G~~I~~G~~N~~G~~T~~Q~~I~~Y~~V~~     +114

ATTGATCCAGAACCGTGCCCAGATTCTGATCAGGAGCCCAAATCTTCTGACAAAACTCAC     +402
I~~D~~P~~E~~P~~C~~P~~D~~S~~D~~Q~~E~~P~~K~~S~~S~~D~~K~~T~~H~~     +134

ACATCCCCACCGTCCCCAGCACCTGAACTCCTGGGGGGATCGTCAGTCTTCCTCTTCCCC     +462
T~~S~~P~~P~~S~~P~~A~~P~~E~~L~~L~~G~~G~~S~~S~~V~~F~~L~~F~~P~~     +154

CCAAAACCCAAGGACACCCTCATGATCTCCCGGACCCCTGAGGTCACATGCGTGGTGGTG     +522
P~~K~~P~~K~~D~~T~~L~~M~~I~~S~~R~~T~~P~~E~~V~~T~~C~~V~~V~~V~~     +174

GACGTGAGCCACGAAGACCCTGAGGTCAAGTTCAACTGGTACGTGGACGGCGTGGAGGTG     +582
D~~V~~S~~H~~E~~D~~P~~E~~V~~K~~F~~N~~W~~Y~~V~~D~~G~~V~~E~~V~~     +194

CATAATGCCAAGACAAAGCCGCGGGAGGAGCAGTACAACAGCACGTACCGTGTGGTCAGC     +642
H~~N~~A~~K~~T~~K~~P~~R~~E~~E~~Q~~Y~~N~~S~~T~~Y~~R~~V~~V~~S~~     +214

GTCCTCACCGTCCTGCACCAGGACTGGCTGAATGGCAAGGAGTACAAGTGCAAGGTCTCC     +702
V~~L~~T~~V~~L~~H~~Q~~D~~W~~L~~N~~G~~K~~E~~Y~~K~~C~~K~~V~~S~~     +234

AACAAAGCCCTCCCAGCCCCCATCGAGAAAACCATCTCCAAAGCCAAAGGGCAGCCCCGA     +762
N~~K~~A~~L~~P~~A~~P~~I~~E~~K~~T~~I~~S~~K~~A~~K~~G~~Q~~P~~R~~     +254

GAACCACAGGTGTACACCCTGCCCCCATCCCGGGATGAGCTGACCAAGAACCAGGTCAGC     +822
E~~P~~Q~~V~~Y~~T~~L~~P~~P~~S~~R~~D~~E~~L~~T~~K~~N~~Q~~V~~S~~     +274

CTGACCTGCCTGGTCAAAGGCTTCTATCCCAGCGACATCGCCGTGGAGTGGGAGAGCAAT     +882
L~~T~~C~~L~~V~~K~~G~~F~~Y~~P~~S~~D~~I~~A~~V~~E~~W~~E~~S~~N~~     +294

GGGCAGCCGGAGAACAACTACAAGACCACGCCTCCCGTGCTGGACTCCGACGGCTCCTTC     +942
G~~Q~~P~~E~~N~~N~~Y~~K~~T~~T~~P~~P~~V~~L~~D~~S~~D~~G~~S~~F~~     +314

TTCCTCTACAGCAAGCTCACCGTGGACAAGAGCAGGTGGCAGCAGGGGAACGTCTTCTCA    +1002
F~~L~~Y~~S~~K~~L~~T~~V~~D~~K~~S~~R~~W~~Q~~Q~~G~~N~~V~~F~~S~~     +334

TGCTCCGTGATGCATGAGGCTCTGCACAACCACTACACGCAGAAGAGCCTCTCCCTGTCT    +1062
C~~S~~V~~M~~H~~E~~A~~L~~H~~N~~H~~Y~~T~~Q~~K~~S~~L~~S~~L~~S~~     +354

CCGGGTAAATGA
P~~G~~K~~*
```

FIGURE 26

```
ATGGGTGTACTGCTCACACAGAGGACGCTGCTCAGTCTGGTCCTTGCACTCCTGTTTCCA    -19
M~~G~~V~~L~~L~~T~~Q~~R~~T~~L~~L~~S~~L~~V~~L~~A~~L~~L~~F~~P~~     -7

AGCATGGCGAGCATGGCAATGCACGTGGCCCAGCCTGCTGTGGTACTGGCCAGCAGCCGA    +42
S~~M~~A~~S~~M~~A~~M~~H~~V~~A~~Q~~P~~A~~V~~V~~L~~A~~S~~S~~R~~    +14
                    +1

GGCATCGCTAGCTTTGTGTGTGAGTATGCATCTCCAGGCAAATGGACTGAGGTCCGGGTG   +102
G~~I~~A~~S~~F~~V~~C~~E~~Y~~A~~S~~P~~G~~K~~W~~T~~E~~V~~R~~V~~    +34

ACAGTGCTTCGGCAGGCTGACAGCCAGGTGACTGAAGTCTGTGCGGCAACCTACATGATG   +162
T~~V~~L~~R~~Q~~A~~D~~S~~Q~~V~~T~~E~~V~~C~~A~~A~~T~~Y~~M~~M~~    +54

GGGAATGAGTTGACCTTCCTAGATGATTCCATCTGCACGGGCACCTCCAGTGGAAATCAA   +222
G~~N~~E~~L~~T~~F~~L~~D~~D~~S~~I~~C~~T~~G~~T~~S~~S~~G~~N~~Q~~    +74

GTGAACCTCACTATCCAAGGACTGAGGGCCATGGACACGGGACTCTACATCTGCAAGGTG   +282
V~~N~~L~~T~~I~~Q~~G~~L~~R~~A~~M~~D~~T~~G~~L~~Y~~I~~C~~K~~V~~    +94

GAGCTCATGTACCCACCGCCATACTACGAGGGCATAGGCAACGGAACCCAGATTTATGTA   +342
E~~L~~M~~Y~~P~~P~~P~~Y~~Y~~E~~G~~I~~G~~N~~G~~T~~Q~~I~~Y~~V~~   +114

ATTGATCCAGAACCGTGCCCAGATTCTGATCAGGAGCCCAAATCTTCTGACAAAACTCAC   +402
I~~D~~P~~E~~P~~C~~P~~D~~S~~D~~Q~~E~~P~~K~~S~~S~~D~~K~~T~~H~~   +134

ACATCCCCACCGTCCCCAGCACCTGAACTCCTGGGGGGATCGTCAGTCTTCCTCTTCCCC   +462
T~~S~~P~~P~~S~~P~~A~~P~~E~~L~~L~~G~~G~~S~~S~~V~~F~~L~~F~~P~~   +154

CCAAAACCCAAGGACACCCTCATGATCTCCCGGACCCCTGAGGTCACATGCGTGGTGGTG   +522
P~~K~~P~~K~~D~~T~~L~~M~~I~~S~~R~~T~~P~~E~~V~~T~~C~~V~~V~~V~~   +174

GACGTGAGCCACGAAGACCCTGAGGTCAAGTTCAACTGGTACGTGGACGGCGTGGAGGTG   +582
D~~V~~S~~H~~E~~D~~P~~E~~V~~K~~F~~N~~W~~Y~~V~~D~~G~~V~~E~~V~~   +194

CATAATGCCAAGACAAAGCCGCGGGAGGAGCAGTACAACAGCACGTACCGTGTGGTCAGC   +642
H~~N~~A~~K~~T~~K~~P~~R~~E~~E~~Q~~Y~~N~~S~~T~~Y~~R~~V~~V~~S~~   +214

GTCCTCACCGTCCTGCACCAGGACTGGCTGAATGGCAAGGAGTACAAGTGCAAGGTCTCC   +702
V~~L~~T~~V~~L~~H~~Q~~D~~W~~L~~N~~G~~K~~E~~Y~~K~~C~~K~~V~~S~~   +234

AACAAAGCCCTCCCAGCCCCCATCGAGAAAACCATCTCCAAAGCCAAAGGGCAGCCCCGA   +762
N~~K~~A~~L~~P~~A~~P~~I~~E~~K~~T~~I~~S~~K~~A~~K~~G~~Q~~P~~R~~   +254

GAACCACAGGTGTACACCCTGCCCCCATCCCGGGATGAGCTGACCAAGAACCAGGTCAGC   +822
E~~P~~Q~~V~~Y~~T~~L~~P~~P~~S~~R~~D~~E~~L~~T~~K~~N~~Q~~V~~S~~   +274

CTGACCTGCCTGGTCAAAGGCTTCTATCCCAGCGACATCGCCGTGGAGTGGGAGAGCAAT   +882
L~~T~~C~~L~~V~~K~~G~~F~~Y~~P~~S~~D~~I~~A~~V~~E~~W~~E~~S~~N~~   +294

GGGCAGCCGGAGAACAACTACAAGACCACGCCTCCCGTGCTGGACTCCGACGGCTCCTTC   +942
G~~Q~~P~~E~~N~~N~~Y~~K~~T~~T~~P~~P~~V~~L~~D~~S~~D~~G~~S~~F~~   +314

TTCCTCTACAGCAAGCTCACCGTGGACAAGAGCAGGTGGCAGCAGGGGAACGTCTTCTCA  +1002
F~~L~~Y~~S~~K~~L~~T~~V~~D~~K~~S~~R~~W~~Q~~Q~~G~~N~~V~~F~~S~~   +334

TGCTCCGTGATGCATGAGGCTCTGCACAACCACTACACGCAGAAGAGCCTCTCCCTGTCT  +1062
C~~S~~V~~M~~H~~E~~A~~L~~H~~N~~H~~Y~~T~~Q~~K~~S~~L~~S~~L~~S~~   +354

CCGGGTAAATGA
P~~G~~K~~*
```

FIGURE 27

SOLUBLE CTLA4 MUTANT MOLECULES AND USES THEREOF

This application is a continuation-in-part of U.S. Ser. No. 08/228,208, filed Apr. 15, 1994, now U.S. Pat. No. 6,090,914, issued Jul. 18, 2000, which was a continuation-in-part of U.S. Ser. No. 08/008,898, filed Jan. 22, 1993, now U.S. Pat. No. 5,770,197, issued Jun. 23, 1998, which was a continuation-in-part of U.S. patent Ser. No. 07/723,617, filed Jun. 27, 1991, now abandoned; the contents of all of which are hereby incorporated by referenced, in their entirety, into the present application.

Throughout this application various publications are referenced. The disclosures of these publications in their entireties are hereby incorporated by reference into this application in order to more fully describe the state of the art to which this invention pertains.

FIELD OF THE INVENTION

The present invention relates to the field of soluble CTLA4 molecules which are mutated from its wildtype counterpart and binds CD80 and/or CD86.

BACKGROUND OF THE INVENTION

Antigen-nonspecific intercellular interactions between T-lymphocytes and antigen-presenting cells (APCs) generate T cell stimulatory signals that generate T cell responses to antigen (Jenkins and Johnson 1993 *Curr. Opin. Immunol.* 5:361–367). Stimulatory signals determine the magnitude of a T cell response to antigen, and whether this response activates or inactivates subsequent responses to antigen (Mueller et al. 1989 *Annu. Rev. Immunol.* 7: 445–480).

T cell activation in the absence of costimulation results in an aborted or anergic T cell response (Schwartz, R. H. 1992 *Cell* 71:1065–1068). One key stimulatory signal is provided by interaction of T cell surface receptors CD28 and CTLA4 with B7 related molecules on APC (e.g., also known as B7-1 and B7-2, or CD80 and CD86, respectively) (P. Linsley and J. Ledbetter 1993 *Annu. Rev. Immunol.* 11:191–212).

The molecule now known as CD80 (B7-1) was originally described as a human B cell-associated activation antigen (Yokochi, T. et al. 1981 *J. Immunol.* 128:823–827; Freeman, G. J. et al. 1989 *J. Immunol.* 143:2714–2722), and subsequently identified as a counterreceptor for the related T cell molecules CD28 and CTLA4 (Linsley, P., et al. 1990 *Proc. Natl. Acad. Sci. USA* 87:5031–5035; Linsley, P. S. et al. 1991(a) *J. Exp. Med.* 173:721–730; Linsley, P. S. et al. 1991(b) *J. Exp. Med.* 174:561–570).

More recently, another counterreceptor for CTLA4 was identified on antigen presenting cells (APC) (Azuma, N. et al. 1993 *Nature* 366:76–79; Freeman 1993(a) *Science* 262:909–911; Freeman, G. J. et al. 1993(b) *J. Exp. Med.* 178:2185–2192; Hathcock, K. L. S., et al. 1994 *J. Exp. Med.* 180:631–640; Lenschow, D. J. et al., 1993 *Proc. Natl. Acad. Sci. USA* 90:11054–11058; Ravi-Wolf, Z., et al. 1993 *Proc. Natl. Acad. Sci. USA* 90:11182–11186; Wu, Y. et al. 1993 *J. Exp. Med.* 178:1789–1793).

This molecule, now known as CD86 (Caux, C., et al. 1994 *J. Exp. Med.* 180:1841–1848), but also called B7-0 (Azuma et al., 1993, supra) or B7-2 (Freeman et al., 1993a, supra), shares about 25% sequence identity with CD80 in its extracellular region (Azuma et al., 1993, supra; Freeman et al., 1993a, supra, 1993b, supra). CD86-transfected cells trigger CD28-mediated T cell responses (Azuma et al., 1993, supra; Freeman et al., 1993a, 1993b, supra).

Comparisons of expression of CD80 and CD86 have been the subject of several studies (Azuma et al. 1993, supra; Hathcock et al., 1994 supra; Larsen, C. P., et al. 1994 *J. Immunol.* 152:5208–5219; Stack, R. M., et al al., 1994 *J. Immunol.* 152:5723–5733). Current data indicate that expression of CD80 and CD86 are regulated differently, and suggest that CD86 expression tends to precede CD80 expression during an immune response.

Soluble forms of CD28 and CTLA4 have been constructed by fusing variable (v)-like extracellular domains of CD28 and CTLA4 to immunoglobulin (Ig) constant domains resulting in CD28Ig and CTLA4Ig. CTLA4Ig binds both CD80 positive and CD86 positive cells more strongly than CD28Ig (Linsley, P. et al. 1994 *Immunity* 1:793–80). Many T cell-dependent immune responses are blocked by CTLA4Ig both in vitro and in vivo. (Linsley, et al., (1991b), supra; Linsley, P. S. et al., 1992(a) *Science* 257:792–795; Linsley, P. S. et al., 1992(b) *J. Exp. Med.* 176:1595–1604; Lenschow, D. J. et al. 1992, *Science* 257: 789–792; Tan, P. et al., 1992 *J. Exp. Med.* 177:165–173; Turka, L. A., 1992 *Proc. Natl. Acad. Sci. USA* 89:11102–11105).

Soluble CTLA4 molecules are effective immunosuppressive agents. There is a need to discover additional soluble CTLA4 molecules for treatments requiring donor-specific and antigen-specific tolerance.

SUMMARY OF THE INVENTION

The invention provides a CTLA4Ig fusion protein reactive with B7 antigen and encoded by DNA deposited as ATCC 68629.

Further, the invention provides a CTLA4Ig fusion protein having the amino acid sequence of a CTLA4Ig fusion protein expressed by a cell deposited as ATCC 10762, wherein said CTLA4Ig fusion protein is reactive with B7 antigen.

The invention also provides a CTLA4Ig fusion protein expressed by a cell deposited as ATCC Accession No. 10762 and a CTLA4Ig fusion protein secreted by a cell deposited as ATCC Accession No. 10762.

Further, the invention provides a CTLA4Ig fusion protein having the amino acid sequence of a CTLA4Ig fusion protein secreted by a cell deposited as ATCC Accession No. 10762, wherein said CTLA4Ig fusion protein is reactive with B7 antigen.

BRIEF DESCRIPTION OF THE FIGURES

FIG. 2: Shows a photograph of a gel obtained from SDS-PAGE chromatographic purification of CTLA4Ig as described in Example 1, infra.

FIG. 3: Shows the nucleotide (SEQ ID NO.: 1) and complete amino acid sequence (SEQ ID NO.: 2) encoding human CTLA4 receptor fused to the oncostatin M signal peptide, and including the newly identified N-linked glycosylation site, as described in Example 1, infra.

A) Control animals treated with PBS (solid lines) or L6 (dotted lines);

B) Animals treated with CTLA4Ig for 14 consecutive days immediately after human islet transplantation;

C) Animals treated with CTLA4Ig every other day for 14 days immediately after human islet transplantation.

Figure 12:
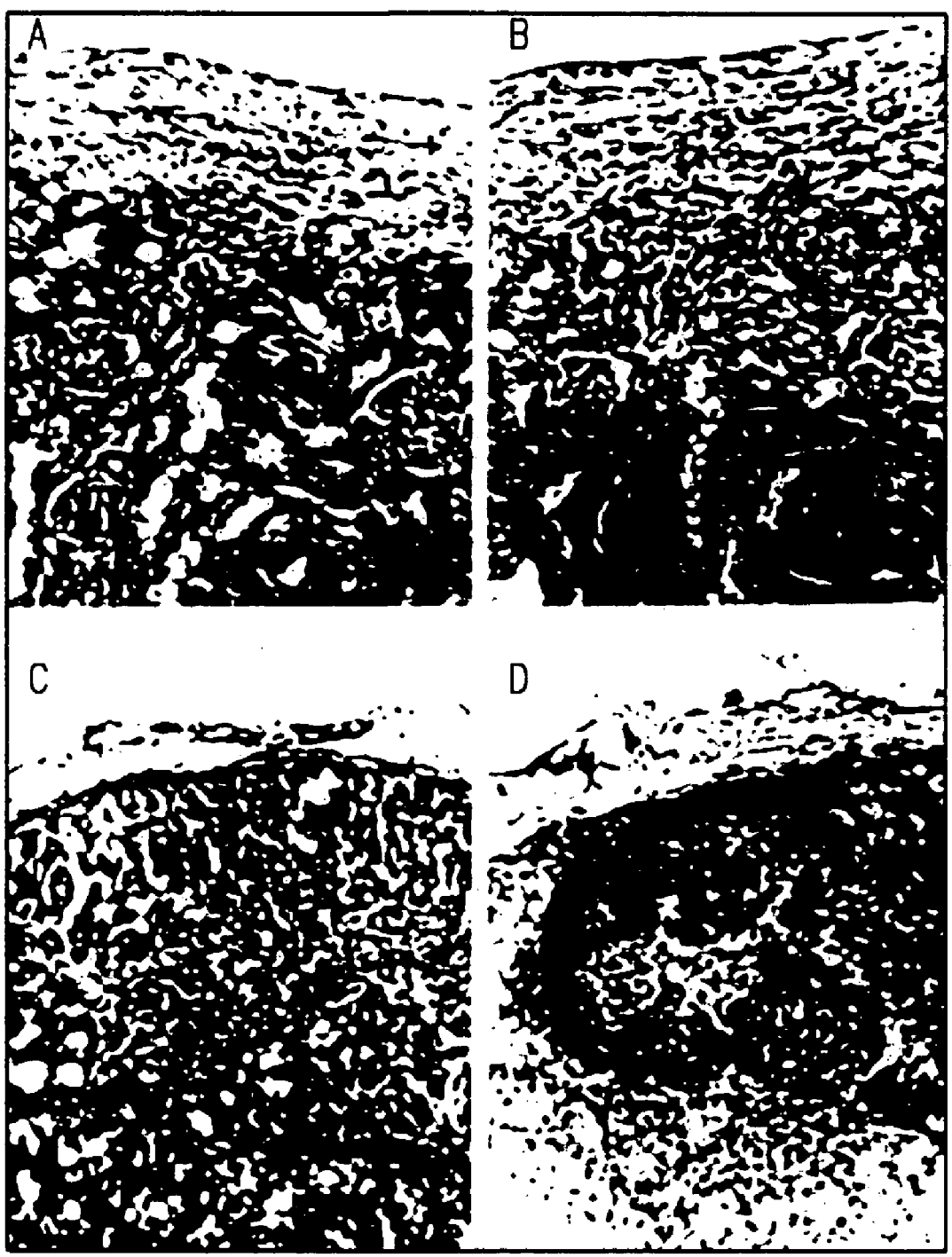

FIG. 12: Shows photographs of histopathology slides of human islets transplanted under the kidney capsule of B10 mice. A) Hematoxylin and eosin staining of human islet grafted in a control B10 mouse; B) The tissue shown in Figure A, stained for insulin; C) Hematoxylin and eosin staining of a human islet in a B10 grafted mouse treated with CTLA4; D) The tissue shown in Figure C, stained for insulin.

Figure 13:
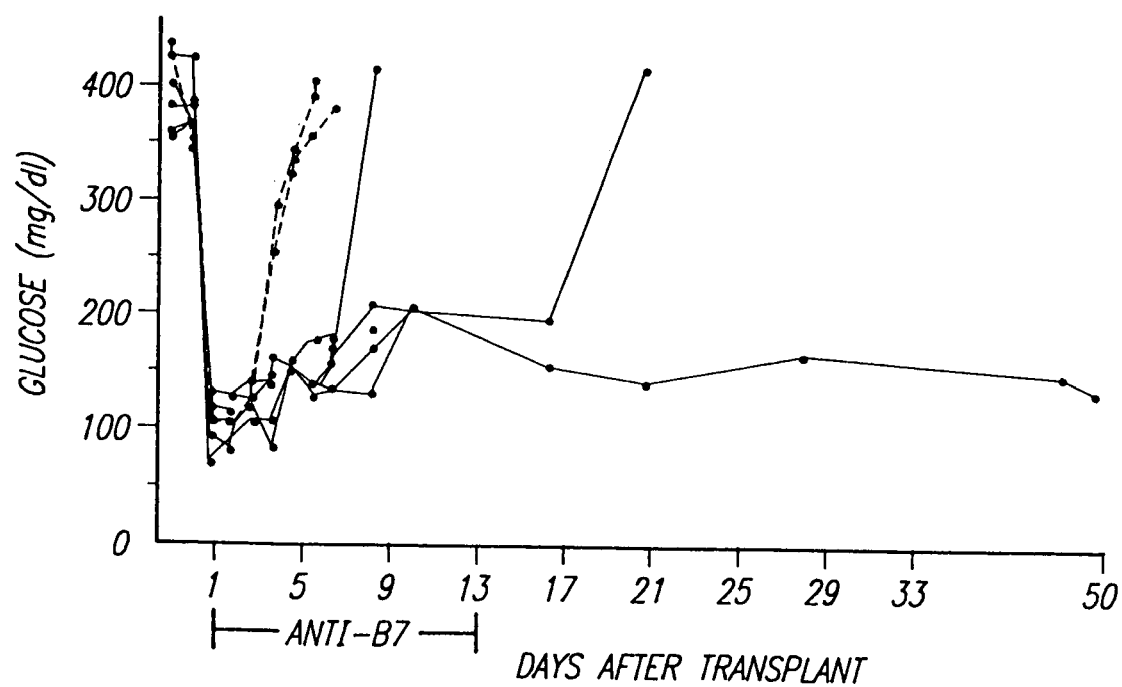

FIG. 13: Depicts a line graph showing the prolongation of islet graft survival with MAb to human B7 in streptozotocin-treated animals.

Figure 14:
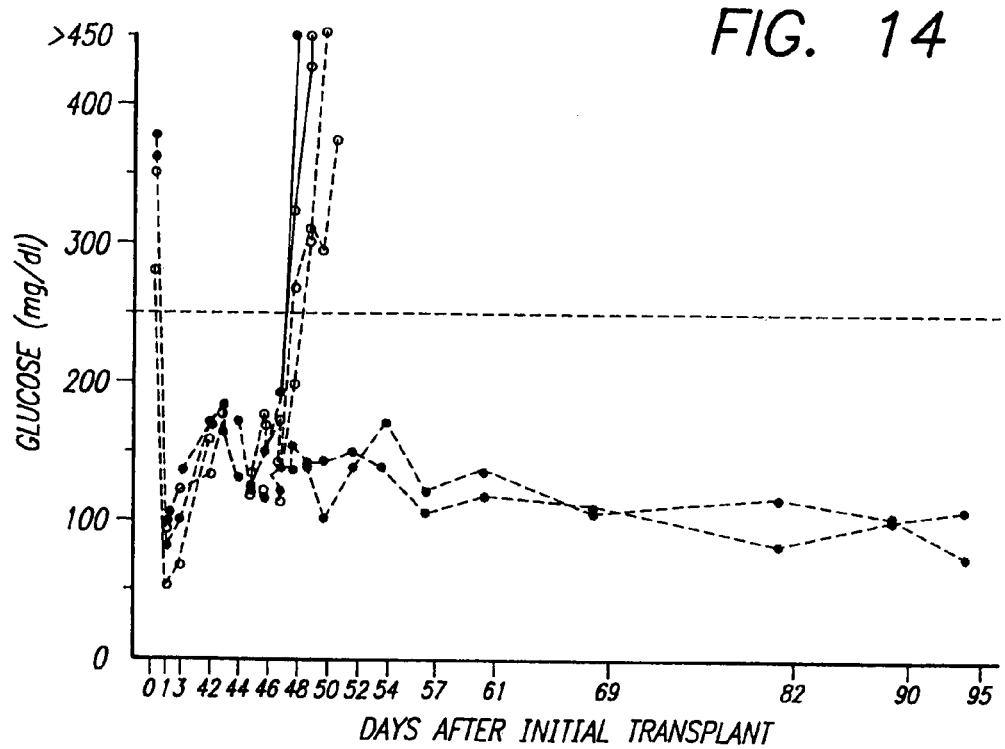

FIG. 14: Depicts a line graph showing induction of donor-specific unresponsiveness to islet graft antigens by CTLA4Ig.

Figure 15:
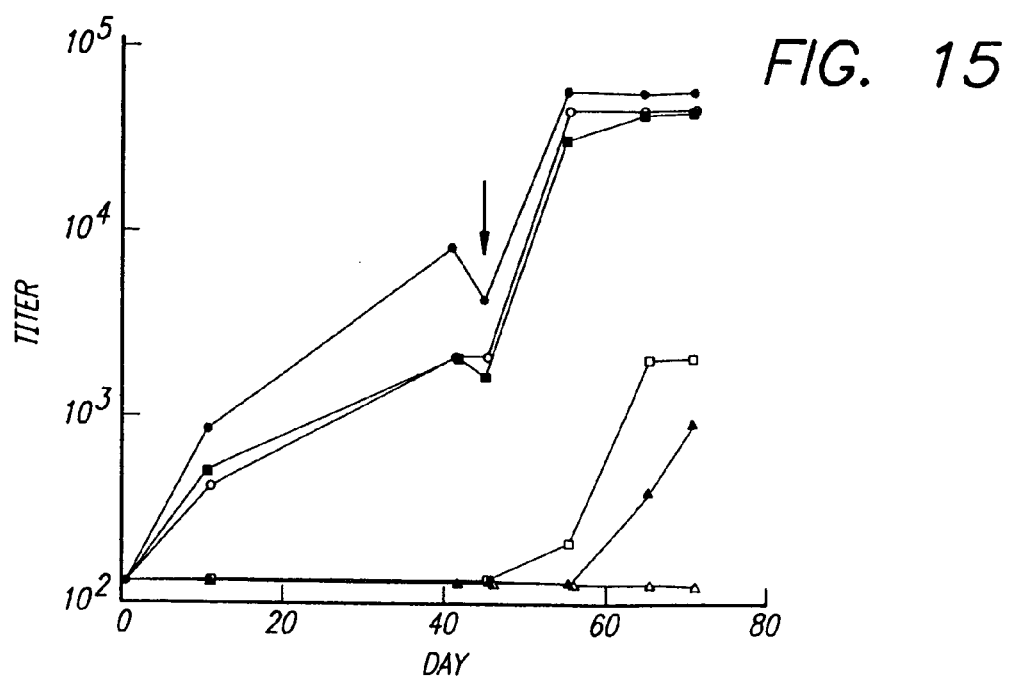

FIG. 15: Depicts a graph showing antibody serum titer levels of mice injected with sheep red blood cells (SRBC), mAb L6 and rat Ig, mAb L6 and anti-IL4, CTLA4Ig and rat Ig, CTLA4Ig and anti-IL4. The X axis measures the antibody-serum titer. The Y axis measures time in days. The closed box represents mice injected with SRBC at day 0 and day 46. The open box represents mice injected with SRBC at day 46. The closed circle represents mice injected with mAb L6 and rat immunoglobulin. The open circle represents mice injected with mAb L6 and anti-IL4 antibody. The closed triangle represents mice injected with CTLA4Ig and rat immunoglobulin. The open triangle represents mice injected with CTLA4Ig and anti-IL4 antibody.

Figure 16:
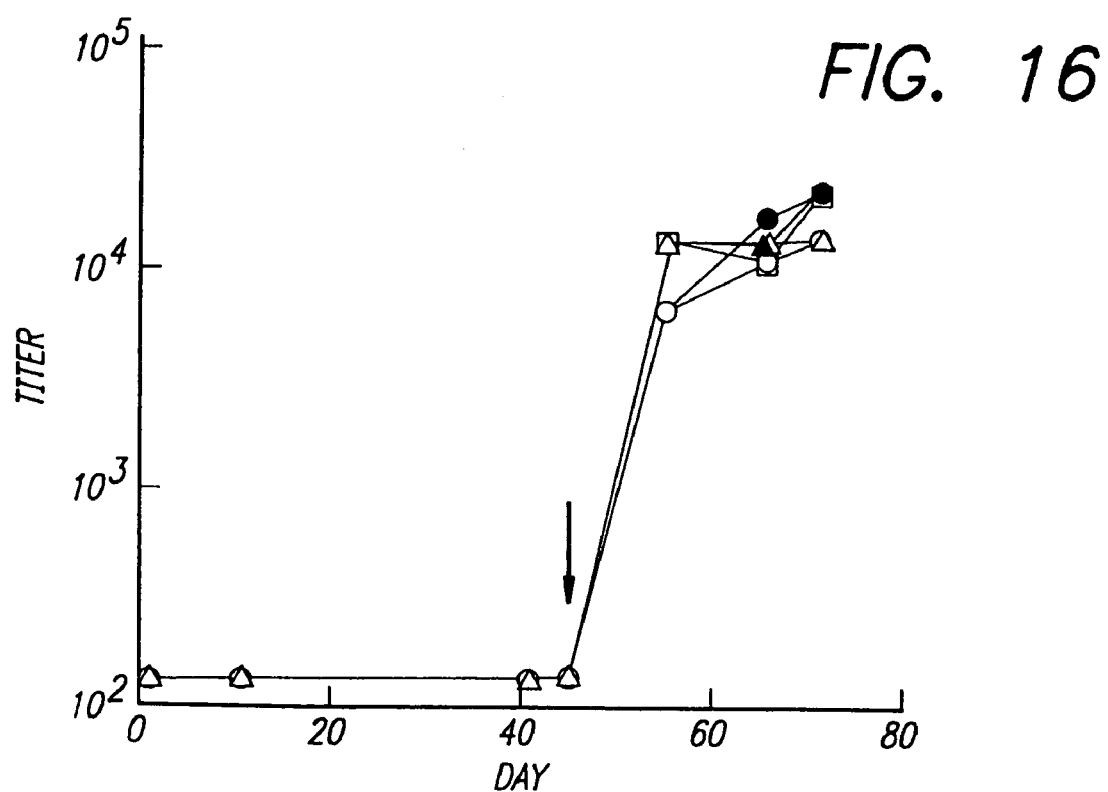

FIG. 16: Depicts a graph showing antibody serum titer levels of mice injected with KLH, mAb L6 and rat Ig, mAb L6 and anti-IL4, CTLA4Ig and rat Ig, CTLA4Ig and anti-IL4. The X axis measures the antibody-serum titer. The Y axis measures time in days. The closed box represents mice injected with keyhole limpet hemocyanin (KLH) at day 46. The closed circle represents mice injected with mAb L6 and rat immunoglobulin. The open circle represents mice injected with mAb L6 and anti-IL4 antibody. The closed triangle represents mice injected with CTLA4Ig and rat immunoglobulin. The open triangle represents mice injected with CTLA4Ig and anti-IL4 antibody.

Figure 17:
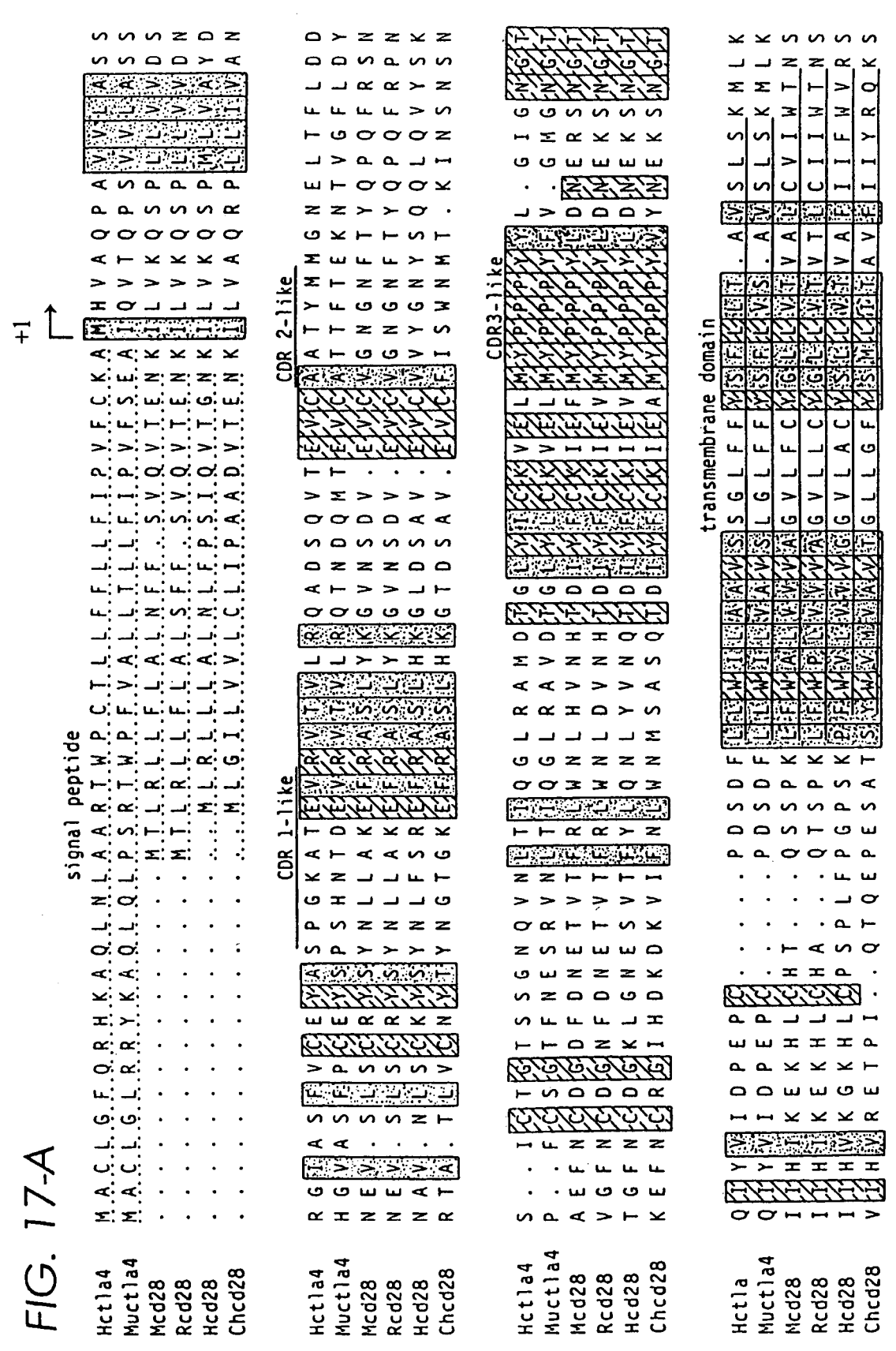

FIG. 17: Depicts sequencing alignment of CD28 and CTLA4 family members. Sequences of human (H) (SEQ ID NO.:7), mouse (M) (SEQ ID NO.:5), rat (R) (SEQ ID NO.:6), and chicken (Ch) CD28 (SEQ ID NO.:8) are aligned with human (SEQ ID NO.: 3) and mouse CTLA4 (SEQ ID NO.:4). The signal peptides are underlined with a dashed line. The transmembrane domains are underlined with a solid line. The CDR-analogous regions are noted. The hatch-filled areas highlight complete conservation of residues while the stipple-filled areas highlight conservative amino acid substitutions in all family members.

Figure 18:
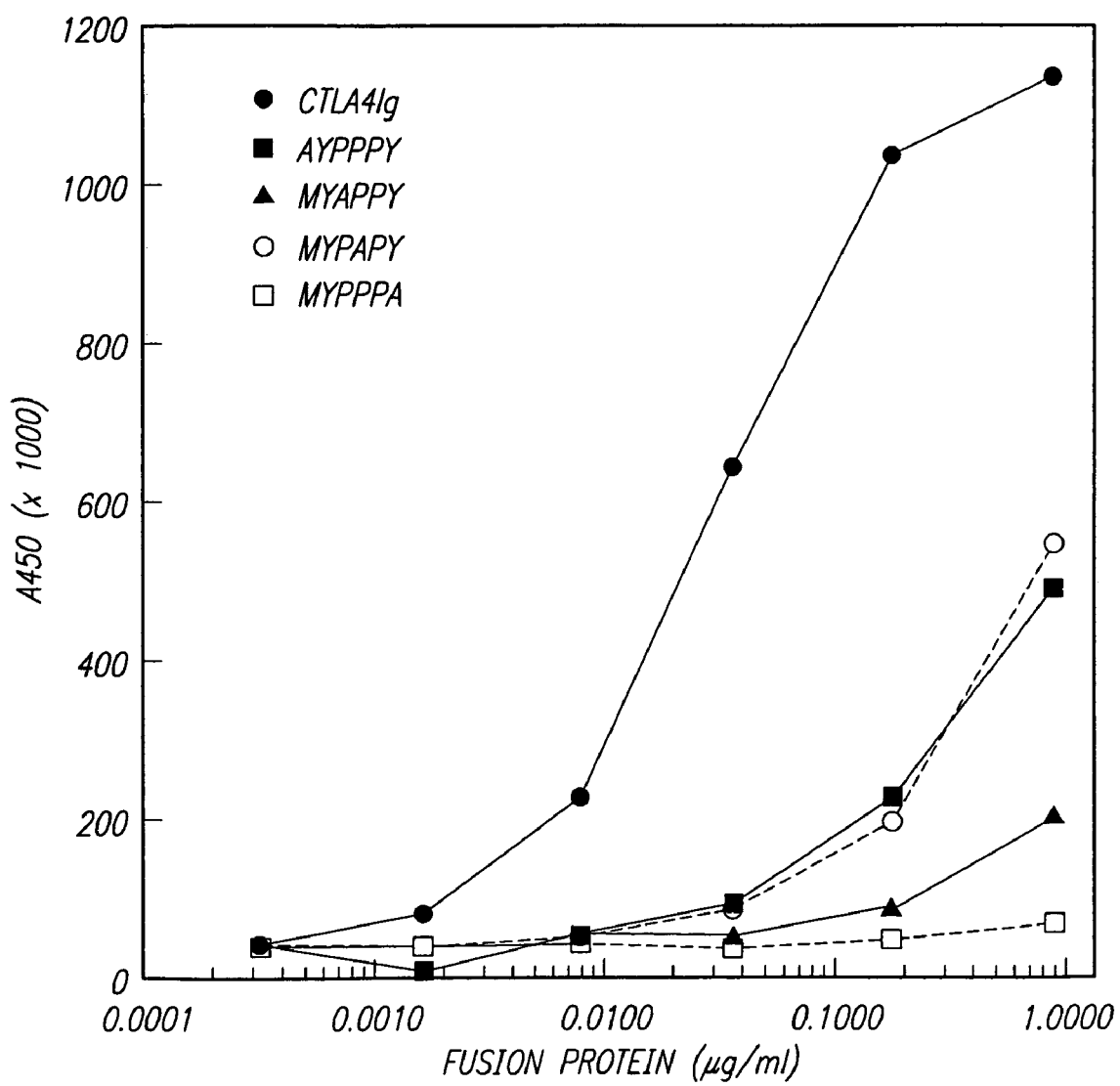

FIG. 18: Depicts a graph showing the results of a binding assay of CTLA4Ig mutants with B7-1. The various CTLA4Ig mutants each have a residue within the MYPPPY motif replaced with an alanine, as described in Example 7, infra.

FIG. 19: Shows a schematic map of CTLA4/CD28Ig hybrid fusion proteins. Open areas represent CD28 sequence; solid areas represent CTLA4 sequence; cross-hatched areas represent beginning of IgG Fc (also refer to Example 7, infra).

Figure 20A:
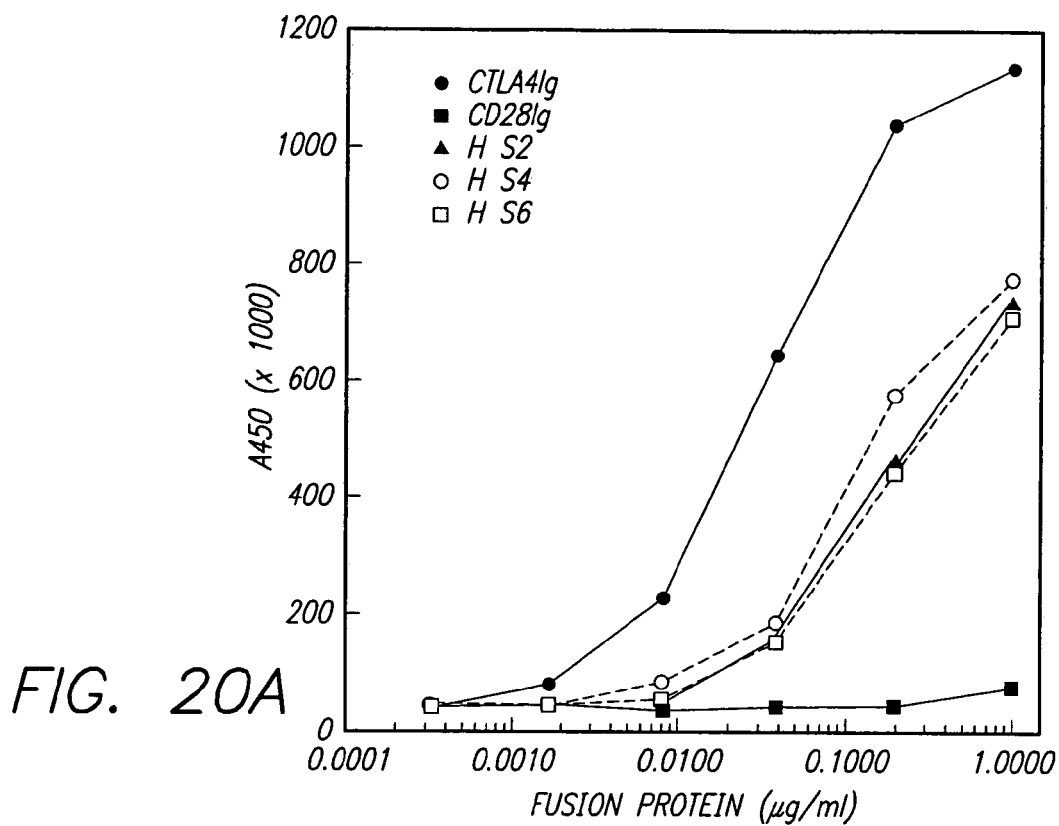
Figure 20B:
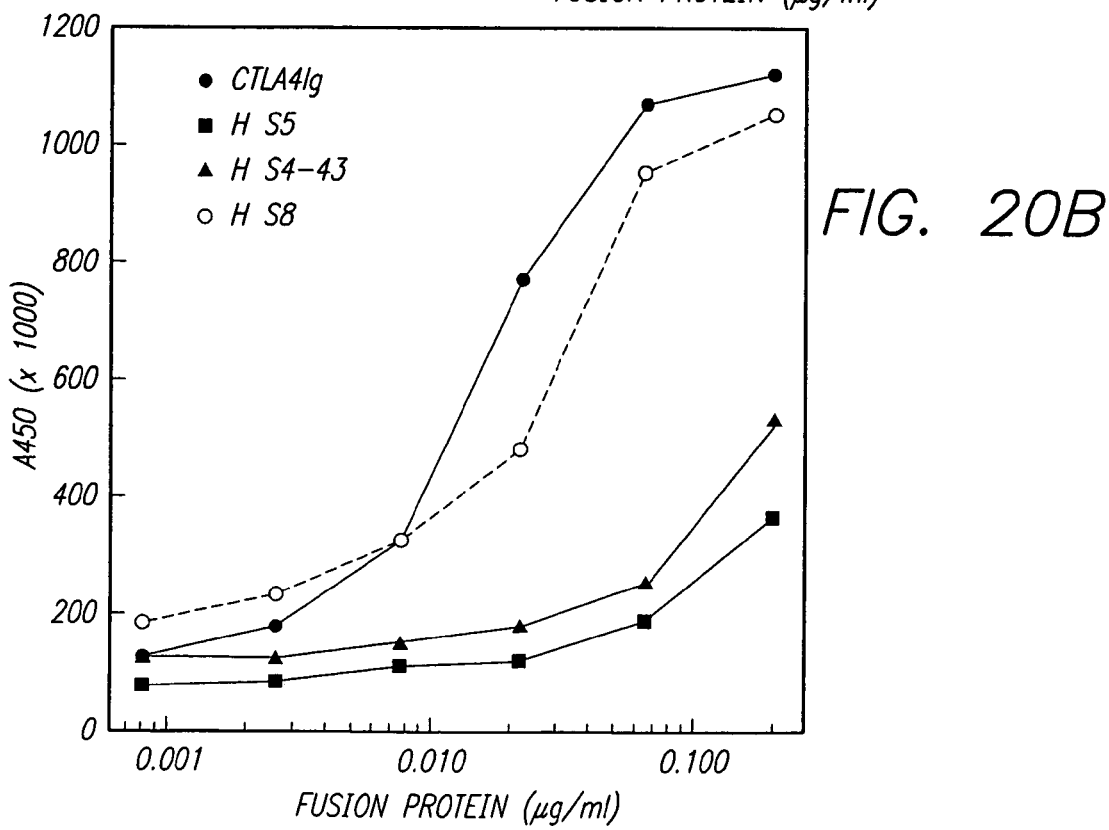

FIGS. 20a–b: Depicts graphs showing the results of a binding assay of CTLA4/CD28 hybrid fusion molecules and B7-1.

A) A comparison of the binding activity of CTLA4Ig, CD28Ig, HS2, HS4, and HS6;

B) A comparison of the binding activity of CTLA4Ig, CD28Ig, HS5, HS4–43, and HS8.

Figure 21:
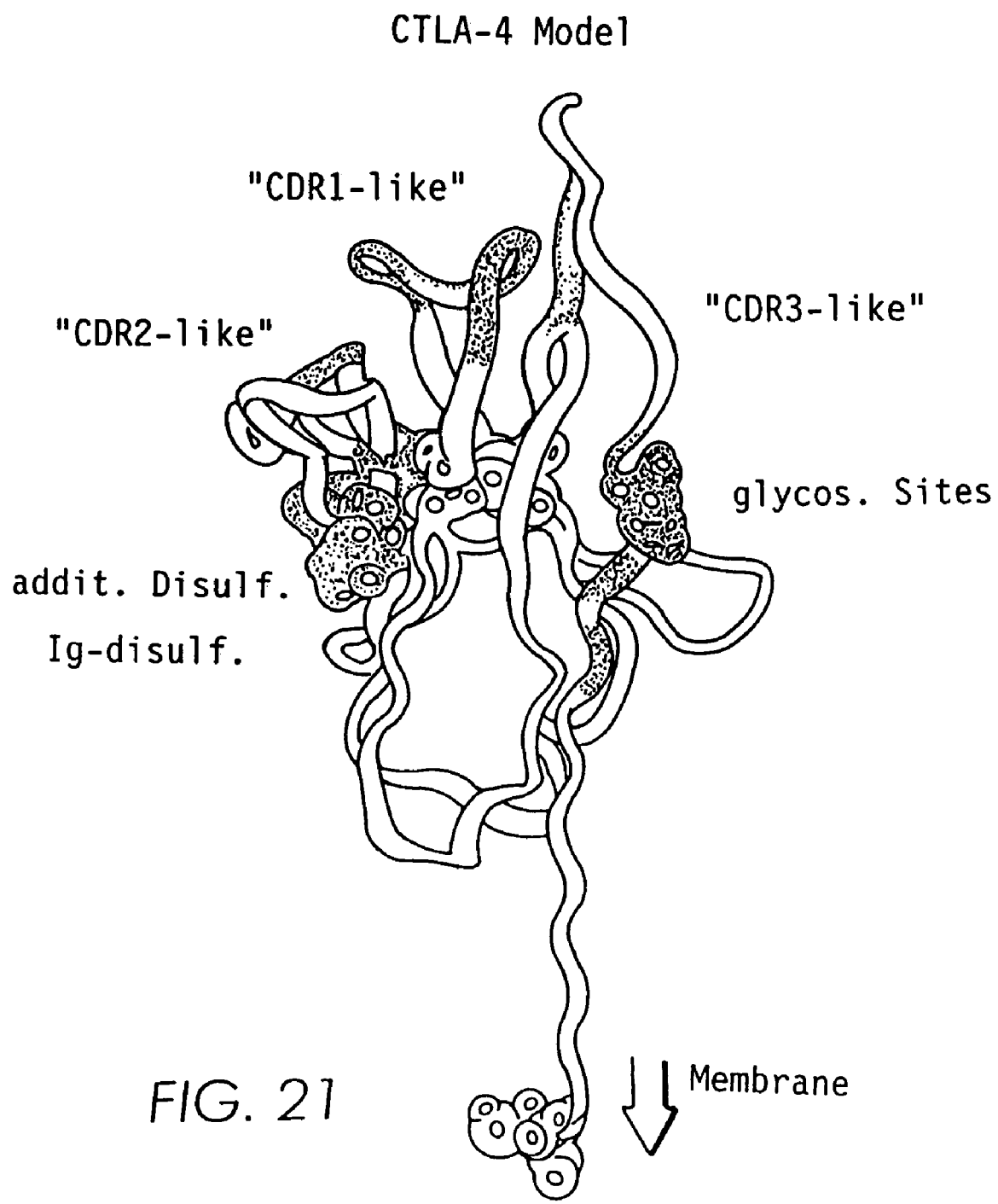

FIG. 21: A molecular model of monomeric CTLA4Ig v-like extracellular domain.

FIG. 22: Depicts the nucleotide (SEQ ID NO.: 9) and amino acid sequence of a CTLA4Ig (SEQ ID NO.: 10) having wildtype extracellular domain of CTLA4.

FIG. 23: Depicts the nucleotide (SEQ ID NO.: 11) and amino acid (SEQ ID NO.: 12) sequences of L104EIg starting at methionine at position +1 to aspartic acid at position +124, or alanine at position −1 to aspartic acid at position +124.

FIG. 24: Depicts the nucleotide (SEQ ID NO. 13 and amino acid sequence (SEQ ID NO.: 14) of L104EA29YIg starting at methionine at position +1 to aspartic acid at position +124, or alanine at position −1 to aspartic acid at position +124.

FIG. 25: Depicts the nucleotide (SEQ ID NO.: 15) and amino acid sequences (SEQ ID NO.: 16) of L104EA29LIg starting at methionine at position +1 to aspartic acid at position +124, or alanine at position −1 to aspartic acid at position +124.

FIG. 26: Depicts the nucleotide (SEQ ID NO.: 17) and amino acid sequences (SEQ ID NO.: 18) of L104EA29TIg starting at methionine at position +1 to aspartic acid at position +124, or alanine at position −1 to aspartic acid at position +124.

FIG. 27: Depicts the nucleotide (SEQ ID NO.: 19) and amino acid sequences (SEQ ID NO.: 20) of L104EA29WIg starting at methionine at position +1 to aspartic acid at position +124, or alanine at position −1 to aspartic acid at position +124.

Figure 28:
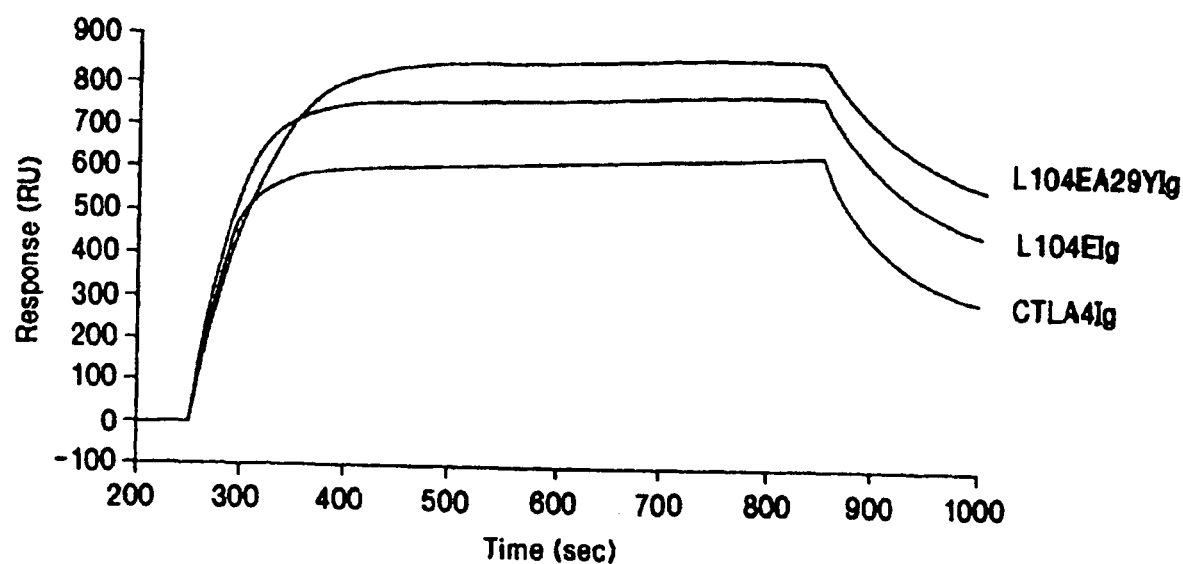

FIG. 28: Depicts the results of an equilibrium binding analysis of L104EA29YIg, L104EIg, and wild-type CTLA4Ig to CD86Ig. L104EA29YIg binds more strongly to CD86Ig than does L104EIg or CTLA4Ig. Equilibrium binding constants (Kd) were determined and shown Example 9, infra. The lower Kd of L104EA29YIg (3.21) than L104EIg (6.06) or CTLA4Ig (13.9) indicates higher binding avidity to CD86Ig. The lower Kd of L104EA29YIg (3.66) than L104EIg (4.47) or CTLA4Ig (6.51) indicates higher binding avidity to CD80Ig.

Figure 29A:
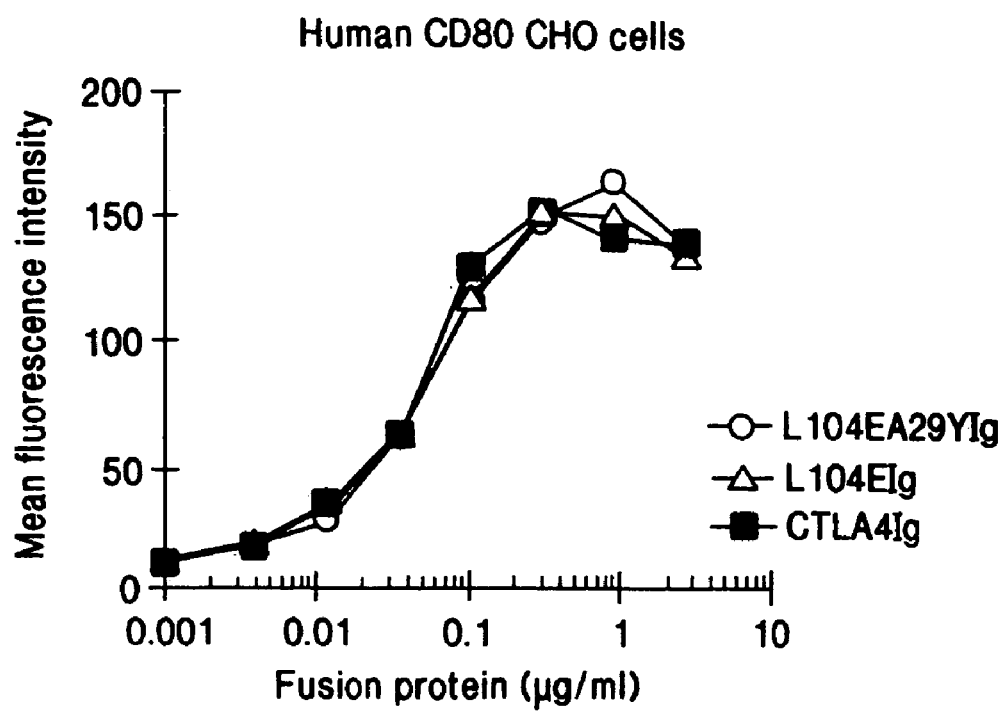
Figure 29B:
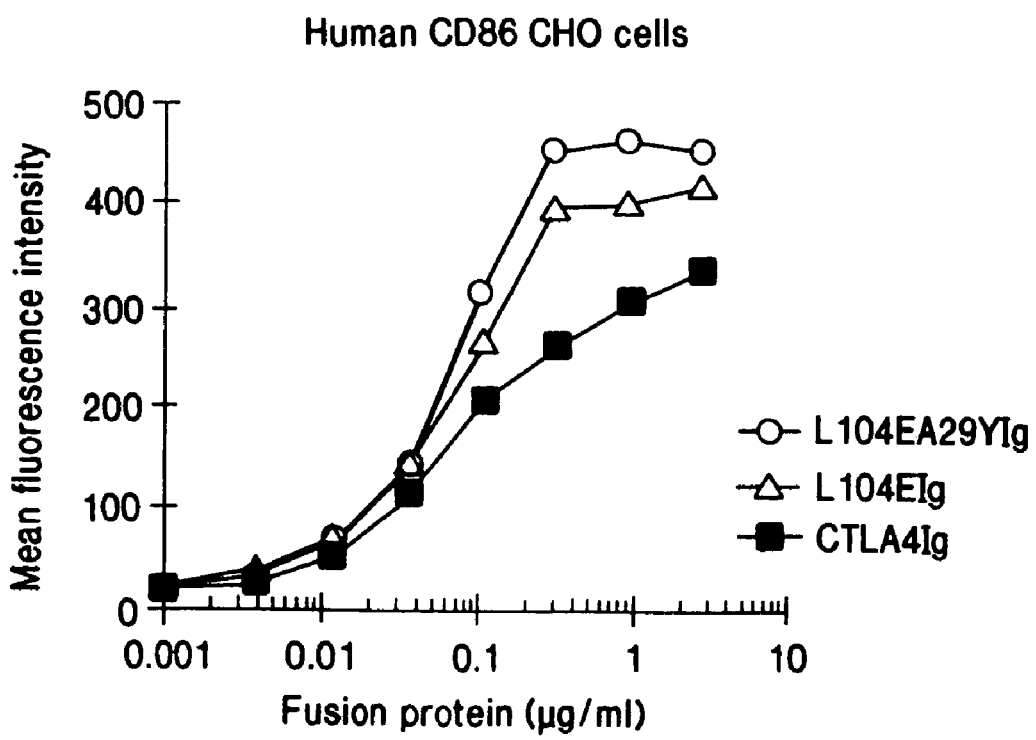

FIG. 29: Depicts the results of a FACS assay, showing L104EA29YIg and L104EIg bind more strongly to CHO cells stably transfected with human CD86 than does CTLA4Ig. A) L104EA29YIg and L104Eig binding to human CD80 CHO-tranfected cells; B) L104EA29YIg and L104Eig binding to human CD86 CHO-tranfected cells.

Figure 30A:
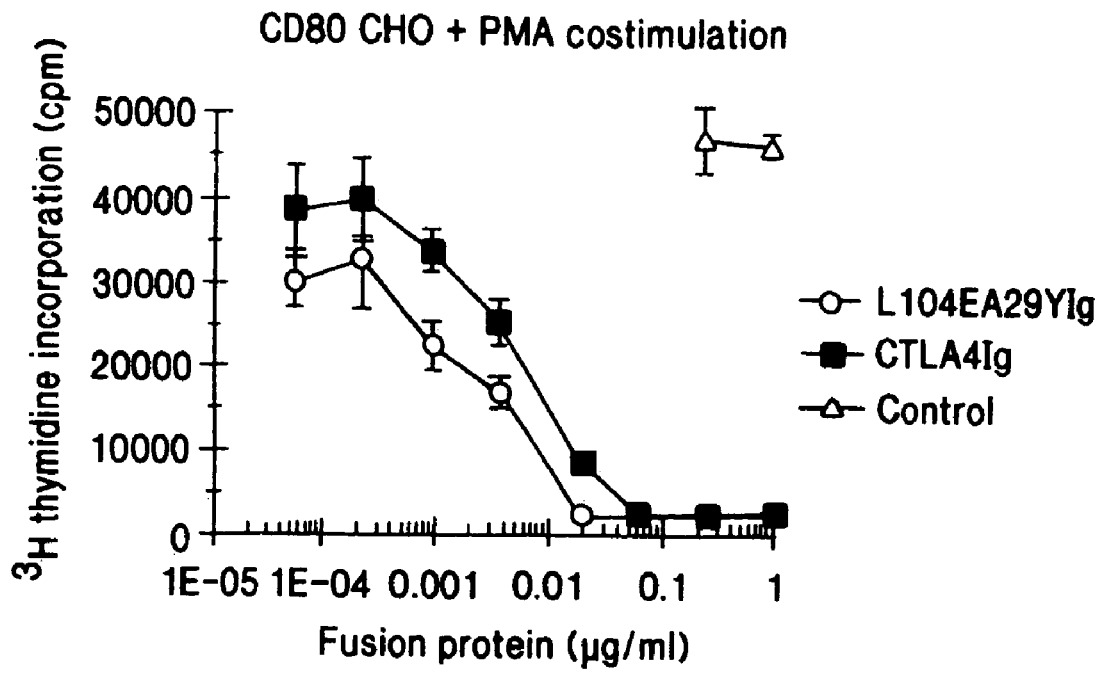
Figure 30B:
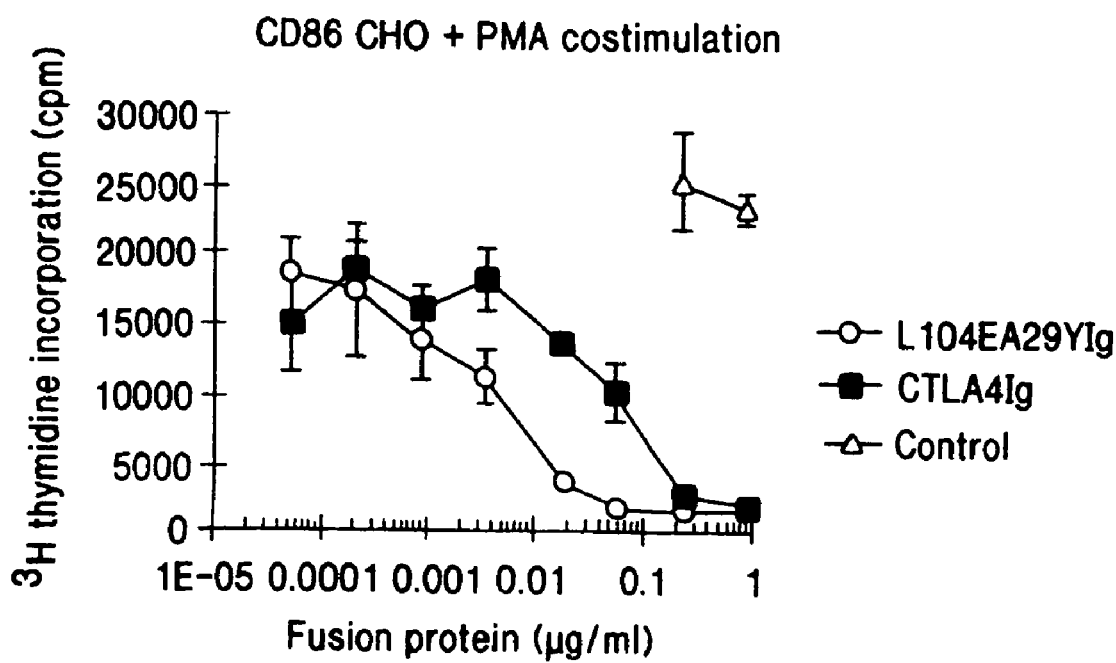

FIG. 30: Depicts the results of in vitro functional assays showing that L104EA29YIg is ~10-fold more effective than CTLA4Ig at inhibiting proliferation of CD86+PMA treated human T cells. Inhibition of CD80+PMA stimulated proliferation by CTLA4Ig and L104EA29YIg is more equivalent. A) L104EA29YIg inhibits proliferation of CD80+PMA treated human T cells; B) L104EA29YIg inhibits proliferation of CD86+PMA treated human T cells.

Figure 31A:
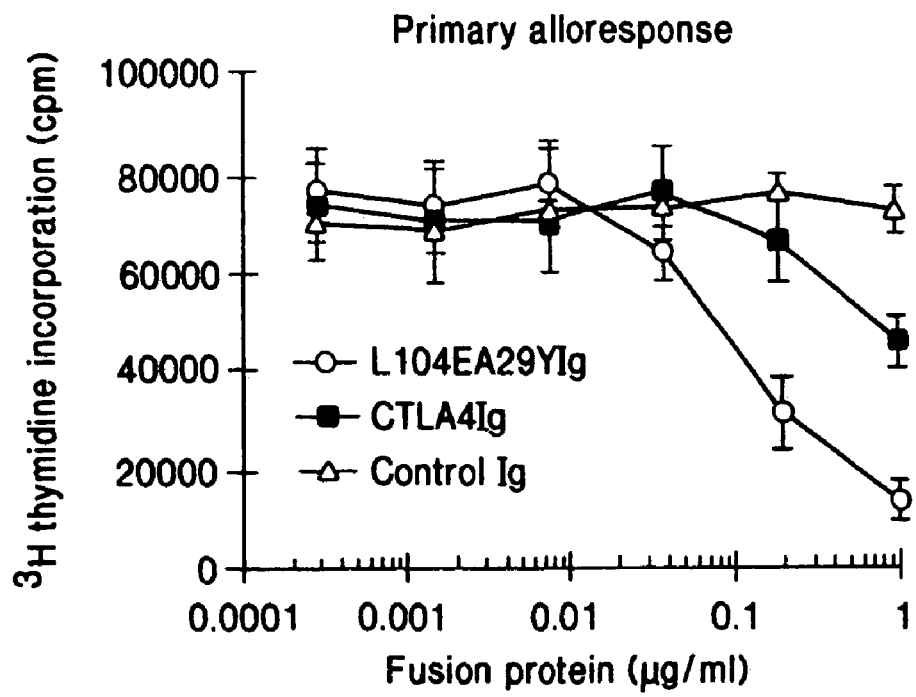
Figure 31B:
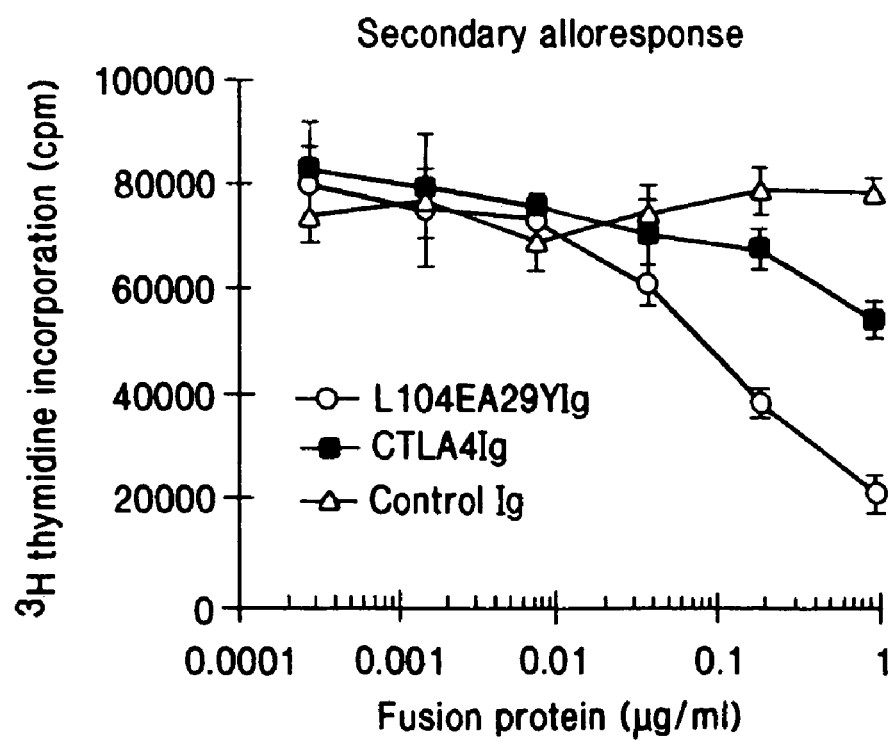

FIG. 31: Depicts the results of in vitro functional assays, showing L104EA29YIg is approximately 10-fold more effective than CTLA4Ig at inhibiting proliferation of primary and secondary allostimulated T cells. A) The effect of L103EA29YIg on primary allostimulated T cells: B) The effect of L103EA29YIg on secondary allostimulated T cells.

Figure 32A:
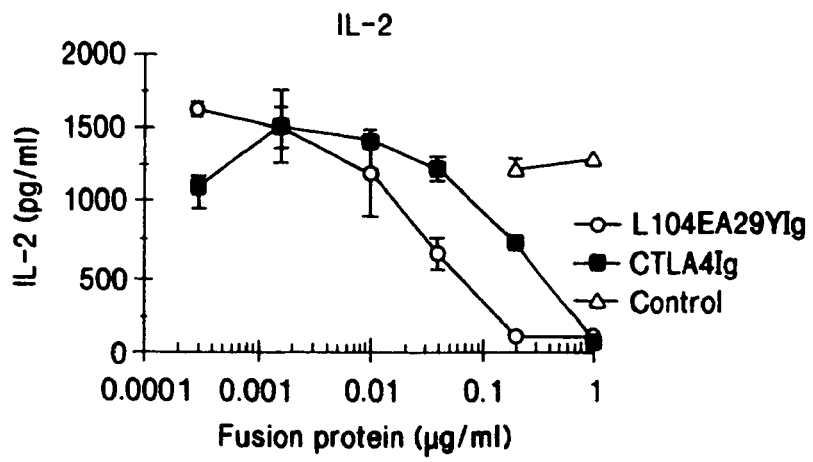
Figure 32B:
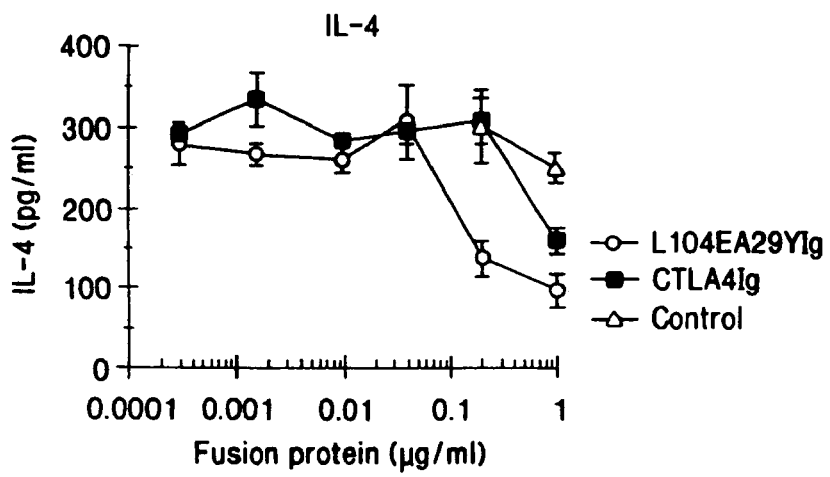
Figure 32C:
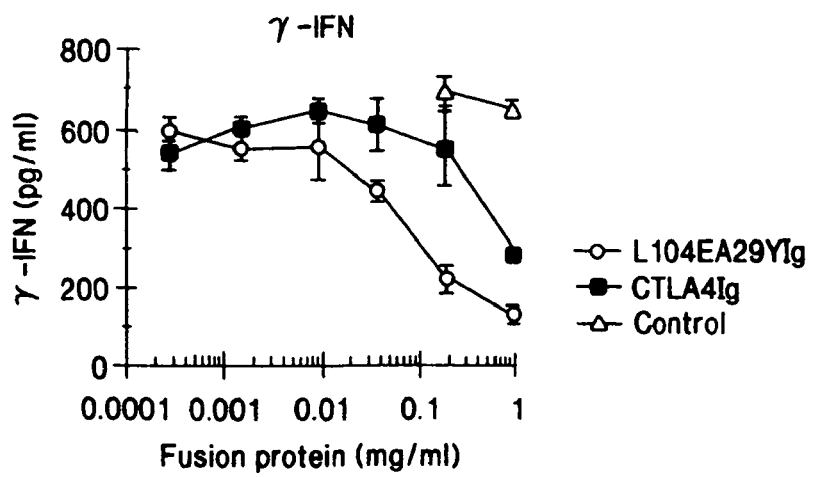

FIG. 32: Depicts the results of in vitro functional assays, showing L104EA29YIg is 5–7-fold more effective than CTLA4Ig at inhibiting IL-2, IL-4, and y-interferon cytokine production of allostimulated human T cells. A) The effect of L104EA29YIg on IL-2 production; B) The effect of L104EA29YIg on IL-4 production; C) The effect of L104EA29YIg on gamma-IFN production.

Figure 33:
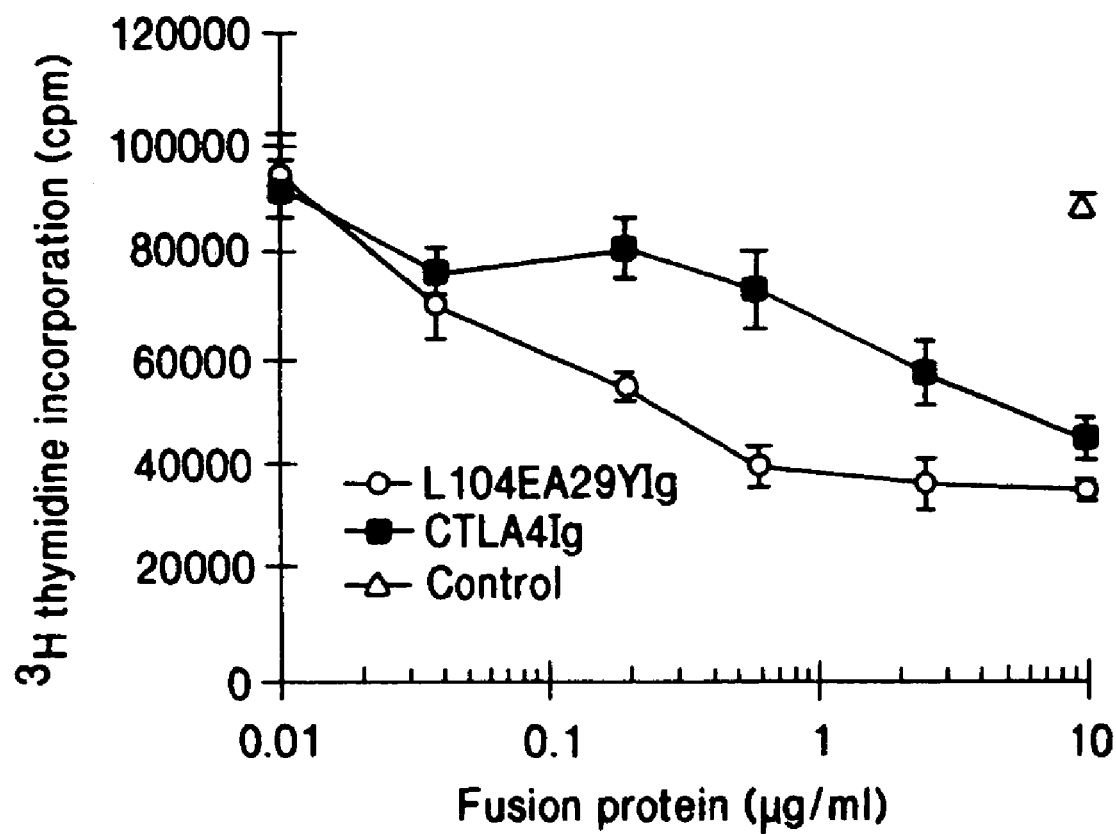

FIG. 33: Depicts the results of in vitro functional assays, showing L104EA29YIg is ~10-fold more effective than CTLA4Ig at inhibiting proliferation of PHA-stimulated monkey PBMC's.

Figure 34A:
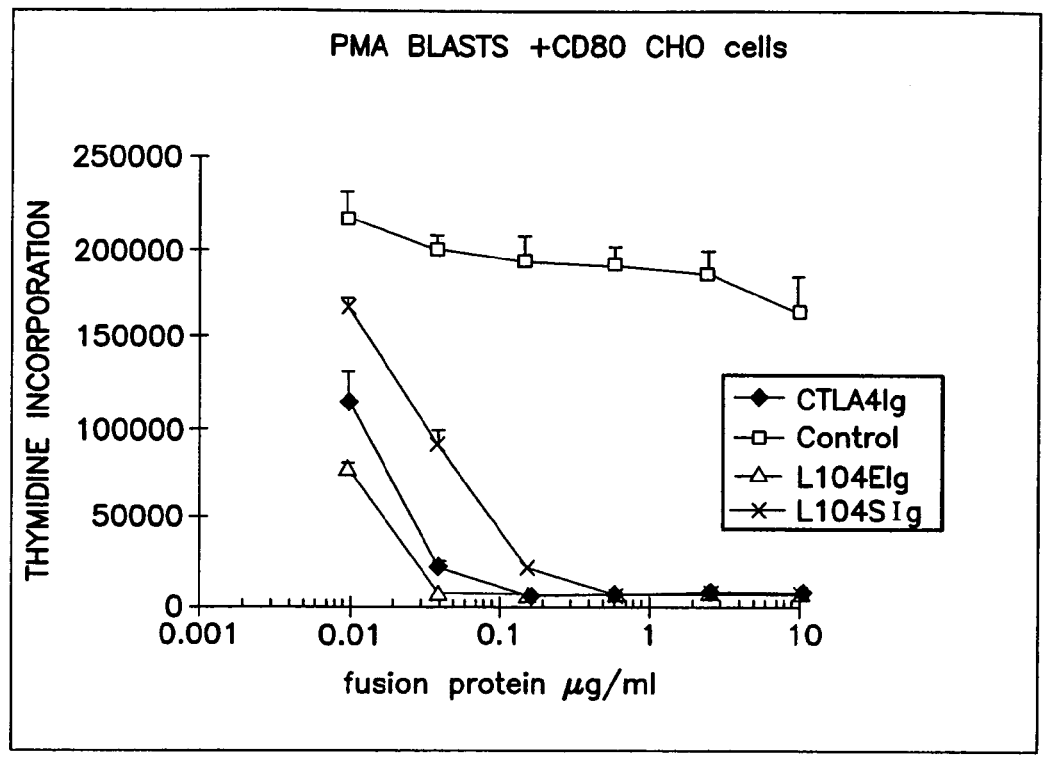

FIG. 34: Depicts the results of in vitro functional assays, showing inhibition of proliferation of T cells stimulated with PMA and CD80-CHO or CD86-CHO cells. A) The inhibitory effect of L104EIg and L104SIg on T cells stimulated with PMA blasts and CD80-CHO cells; B) the inhibitory effect of L104DIg and L104SIg on T cells stimulated with PMA blasts and CD80-CHO cells.

Figure 35A:
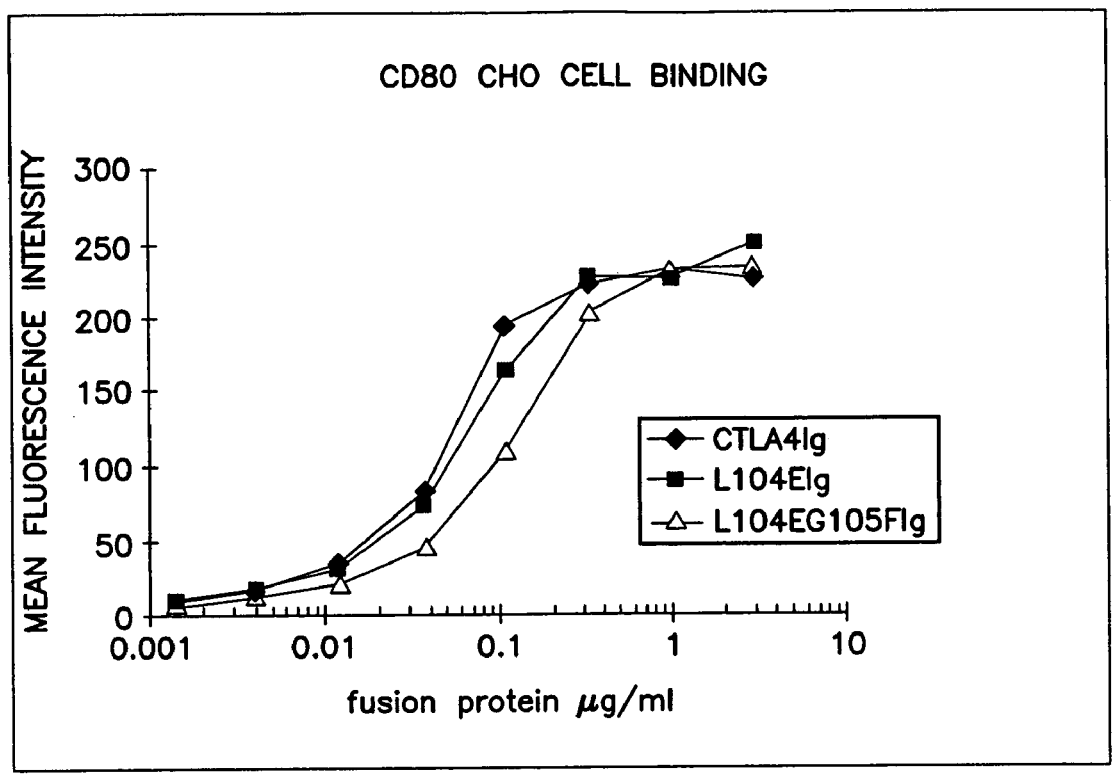
Figure 35B:
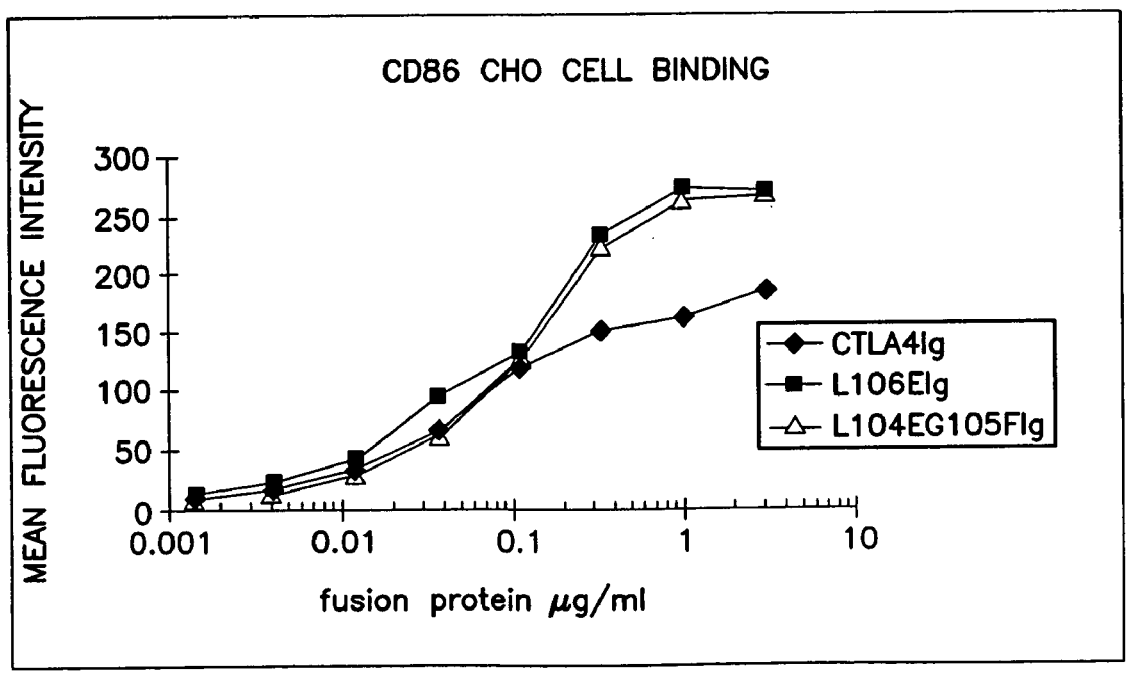

FIG. 35: Depicts the results of a FACS assay, showing L104EIg and L104EG105FIg bind CHO cells stably transfected with human CD80 or CD86. A) L104EIg and L104EG105FIg bind to human CD80 CHO-transfected cells; B) L104EIg and L104E105FIg bind to human CD86 CHO-transfected cells.

Figure 36:
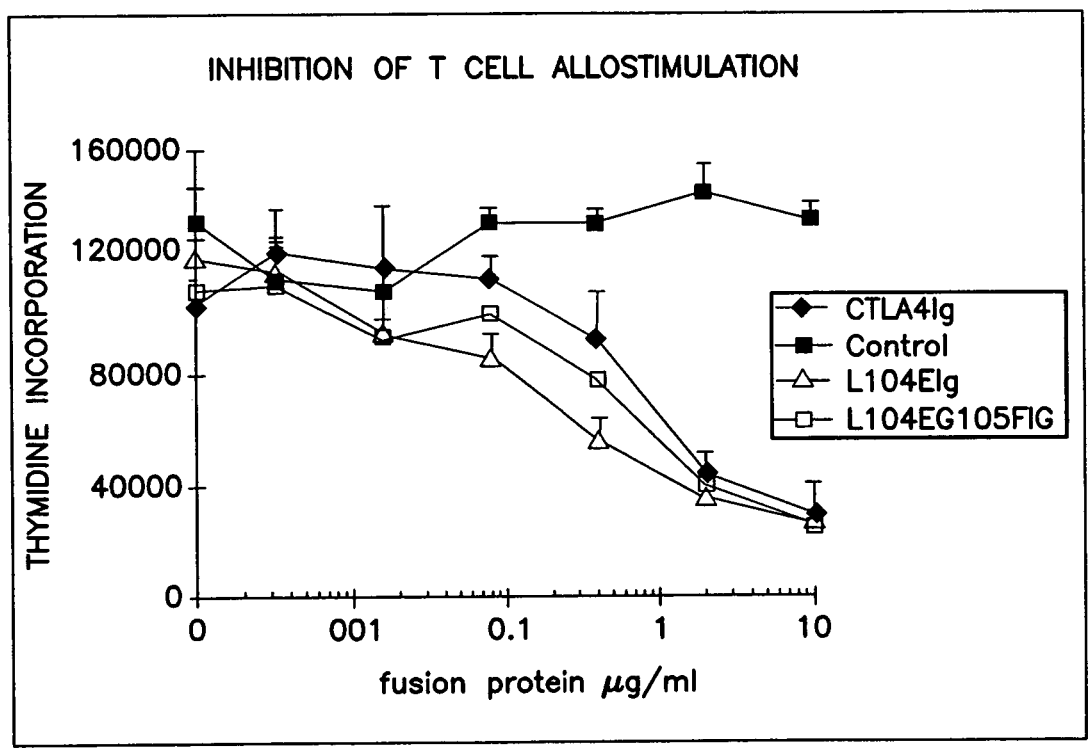

FIG. 36: Depicts the results of in vitro functional assays, showing L104EIg and L104EG105FIg inhibit proliferation of primary allostimulated T cells.

Figure 37A:
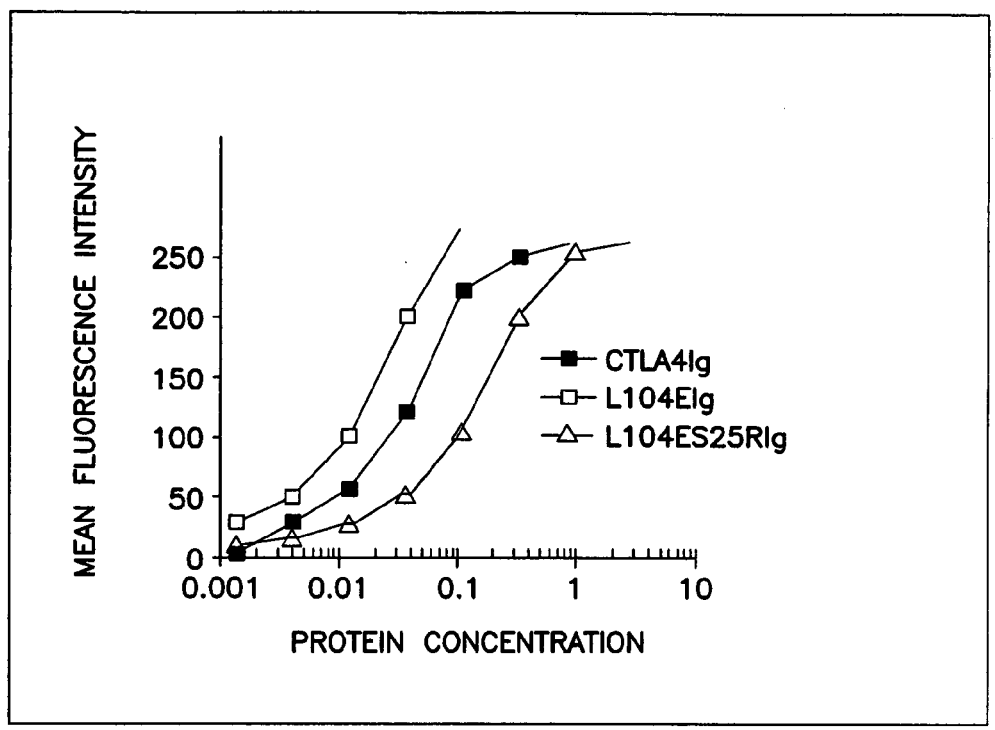
Figure 37B:
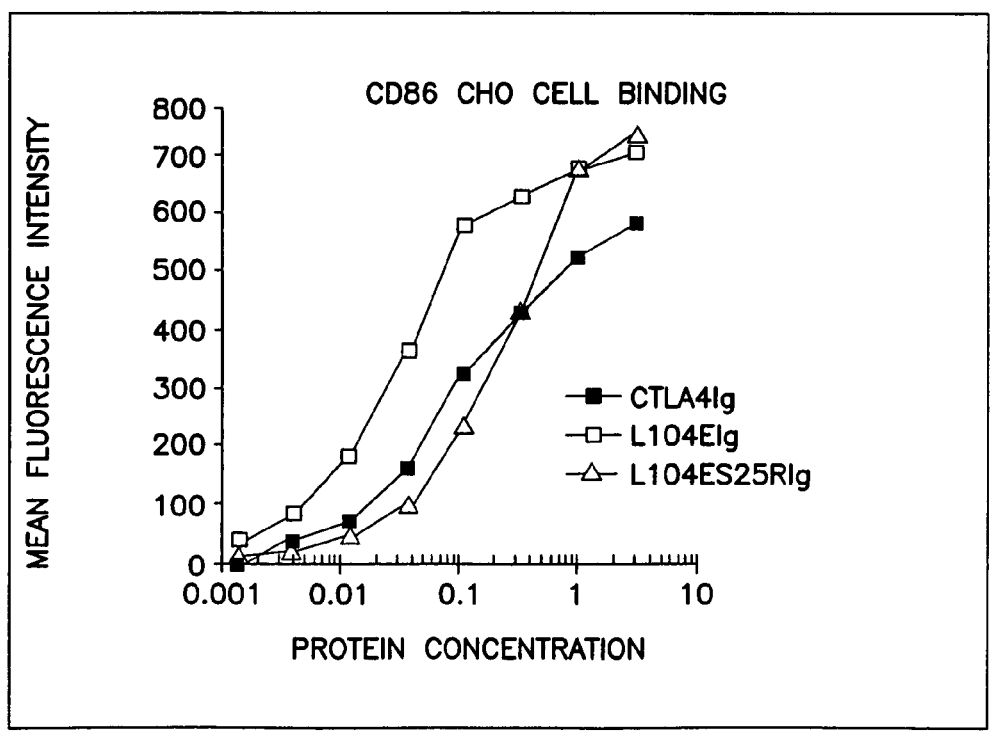

FIG. 37: Depicts the results of a FACS assay, showing L104EIg and L104ES25RIg bind CHO cells stably transfected with human CD80 or CD86. A) L104EIg and L104ES25RIg bind to human CD80 CHO-transfected cells; B) L104EIg and L104ES25RIg bind to human CD86 CHO-transfected cells.

DETAILED DESCRIPTION OF THE INVENTION

Definitions

As used in this application, the following words or phrases have the meanings specified.

As used herein a "CTLA4 mutant molecule" is a molecule including full length CTLA4 or portions thereof (e.g., fragments) having the activity of binding CD80 and/or CD86 and that has a mutation or multiple mutations in the extracellular domain of CTLA4, so that the sequence of the mutant molecule is not identical to the wildtype CTLA4 molecule. The CTLA4 mutant molecules may be fusion molecules comprising a non-CTLA4 molecule attached thereto. The mutant molecules may be soluble (i.e., circulating) or bound to a surface. CTLA4 mutant molecules can be made synthetically or recombinantly.

As used herein, the term "mutation" means a change in the amino acid sequence of the wild-type CTLA4 extracellular domain. The amino acid changes include substitutions, deletions, insertions, additions, or truncations. The mutant molecule can have one or more mutations.

As used herein "the extracellular domain of CTLA4" is the portion of the CTLA4 receptor that extends outside the cell membrane or any portion thereof which recognizes and binds CD80 and/or CD86.

As used herein "CTLA4" has the sequence of wildtype, full length CTLA4 as shown in FIG. 3 of U.S. Pat. Nos. 5,434,131, 5,844,095, 5,851,795, or any portion thereof which binds CD80 or CD86 or interferes with CD80 or CD86 so that it blocks binding to CD28 or CTLA4 (e.g., endogenous CD28 or CTLA4). CTLA4 is a cell surface protein, having an N-terminal extracellular domain, a transmembrane domain, and a C-terminal cytoplasmic domain. The extracellular domain binds to target antigens, such as CD80 or CD86. In a cell, the naturally occurring, wild type CTLA4 protein is translated as an immature polypeptide, which includes a signal peptide at the N-terminal end. The immature polypeptide undergoes post-translational processing, which includes cleavage and removal of the signal peptide to generate a CTLA4 cleavage product having a newly generated N-terminal end that differs from the N-terminal end in the immature form. One skilled in the art will appreciate that additional post-translational processing may occur, which removes one or more of the amino acids from the newly generated N-terminal end of the CTLA4 cleavage product. The mature form of the CTLA4 molecule includes the extracellular domain or any portion thereof which binds to CD80 and/or CD86.

One embodiment of a soluble CTLA4 has been deposited with the American Type Culture Collection (ATCC) 10801 University Blvd., Manassas, Va. 20110-2209, under the provisions of the Budapest Treaty on May 31, 1991 and has been accorded ATCC accession number: 68629. ATCC 68629 is DNA encoding CTLA4Ig. Additionally, the CTLA4Ig-24 CHO cell line has been deposited with the ATCC under the Budapest Treaty on May 31, 1991 and has been accorded accession number ATCC 10762. DNA encoding L104EA29YIg was submitted for deposit on Jun. 19, 2000 with the American Type Culture Collection (ATCC), 10801 University Blvd., Manassas, Va. 20110-2209. The DNA encoding L104EA29YIg has been accorded ATCC accession number PTA-2104.

As used herein a "non-CTLA4 protein sequence" or "non-CTLA4 molecule" means any protein molecule which does not bind CD80 and/or CD86 and does not interfere with the binding of CTLA4 to its target. An example includes, but is not limited to, an immunoglobulin (Ig) constant region or portion thereof. Preferably, the Ig constant region is a human or monkey Ig constant region, e.g., human C(gamma)1, including the hinge, CH2 and CH3 regions. The Ig constant region can be mutated to reduce its effector functions (U.S. Pat. Nos. 5,844,095; 5,851,795; and 5,885,796).

As used herein a "fragment" is any portion of CTLA4 mutant molecule, preferably the extracellular domain of CTLA4 or a portion thereof that recognizes and binds its target, e.g., CD80 and/or CD86.

As used herein "blocks T cell proliferation" means to bind CD80 or CD86, e.g., on APCs, so that T cell proliferation is detectably inhibited by an art recognized test such as by nucleotide incorporation into DNA or clonogenic assay.

As used herein "blocking B7 interaction" means to interfere with the binding of B7 to its ligands such as CD28 and/or CTLA4 thereby obstructing T cell and B cell interaction.

As used herein "regulating functional CTLA4 positive T cell interaction" means to suppress an immune response directly or indirectly.

As used herein "at least a portion" means any part of the molecule which recognizes and binds its target, e.g., CD80 or CD86.

As used herein "immunoproliferative disease" means any disease mediated by T cell interactions with CD80 or CD86 positive cells including but not limited to graft versus host disease (GVHD); psoriasis; immune disorders associated with graft transplantation rejection; T cell lymphoma; T cell acute lymphoblastic leukemia; testicular angiocentric T cell lymphoma; benign lymphocytic angiitis; and autoimmune diseases such as lupus erythematosus, Hashimoto's thyroiditis, primary myxedema, Graves' disease, pernicious anemia, autoimmune atrophic gastritis, Addison's disease, insulin dependent diabetes mellitus, good pasture's syndrome, myasthenia gravis, pemphigus, Crohn's disease, sympathetic ophthalmia, autoimmune uveitis, multiple sclerosis, autoimmune hemolytic anemia, idiopathic thrombocytopenia, primary biliary cirrhosis, chronic action hepatitis, ulceratis colitis, Sjogren's syndrome, rheumatoid arthritis, polymyositis, scleroderma, and mixed connective tissue disease.

In order that the invention herein described may be more fully understood, the following description is set forth.

COMPOSITIONS OF THE INVENTION

The present invention provides soluble CTLA4 mutant molecules which recognize and bind CD80 and/or CD86. In some embodiments, the CTLA4 mutant molecules have similar or lower avidity to CD80 and/or CD86 than CTLA4Ig. The preferred embodiment includes soluble CTLA4 mutants having a higher avidity to CD80 and/or CD86 than CTLA4Ig. The preferred mutant molecules should be better able to interfere or disrupt the priming of antigen specific activated cells than CTLA4Ig The present invention provides CTLA4 mutant molecules comprising at least the extracellular domain of CTLA4 or portions thereof that bind CD80 and/or CD86. The extracellular portion of CTLA4 comprises methionine at position +1 through aspartic acid at position +124 (e.g., FIG. 3 or 22). The extracellular portion of the CTLA4 can comprise alanine at position −1 through aspartic acid at position +124 (e.g., FIG. 3 or 22). The extracellular portion of the CTLA4 can comprise glutamic acid at position +95 through cysteine at position +120. The extracellular portion of the CTLA4 can comprise methionine at position +1 through cysteine at position +21 and glutamic acid at position +95 through aspartic acid at position +122. The extracellular portion of the CTLA4 can comprise methionine at position +1 through tyrosine at position +23 and valine at position +32 through aspartic acid at position +122. The extracellular portion of the CTLA4 can comprise alanine at position +24 through glutamic acid at position +31 and glutamic acid at position +95 through aspartic acid at position +122. The extracellular portion of the CTLA4 can comprise alanine at position +24 through glutamic acid at position +31 and glutamic acid at position +95 through isoleucine at position +112. The extracellular portion of the CTLA4 can comprise alanine at position +24 through glutamic acid at position +31 and tyrosine at position +113 through aspartic acid at position +122. The extracellular portion of the CTLA4 can comprise alanine at position +50 through glutamic acid at position +57 and glutamic acid at position +95 through aspartic acid at position +122. The extracellular portion of the CTLA4 can comprise alanine at position +24 through glutamic acid at position +31; alanine at position +50 through glutamic acid at position +57; and glutamic acid at position +95 through aspartic acid at position +122. The extracellular portion of the CTLA4 can comprise alanine at position +50 through glutamic acid at position +57 and glutamic acid at position +95 through isoleucine at position +112. The extracellular portion of the CTLA4 can comprise alanine at position +24 through glutamic acid at position +31; alanine at position +50 through glutamic acid at position +57; and glutamic acid at position +95 through aspartic acid at position +122. The extracellular portion of CTLA4 can comprise alanine at position +24 through valine at position +94. The extracellular portion of CTLA4 can comprise alanine at position −1 through cysteine at position +21. The extracellular portion of CTLA4 can comprise methionine at position +1 through cysteine at position +21. The extracellular portion of CTLA4 can comprise glutamic acid at position +95 through aspartic acid at position +122. The extracellular portion of CTLA4 can comprise alanine at position −1 through valine at position +94. The extracellular portion of CTLA4 can comprise methionine at position +1 through valine at position +94. The extracellular portion of CTLA4 can comprise alanine at position +24 through glutamic acid at position +31. The extracellular portion of CTLA4 can comprise alanine at position −1 through tyrosine at position +23. The extracellular portion of CTLA4 can comprise methionine at position +1 through tyrosine at position +23. The extracellular portion of CTLA4 can comprise valine at position +32 through aspartic acid at position +122. The extracellular portion of CTLA4 can comprise tyrosine at position +113 through aspartic acid at position +122. The extracellular portion of CTLA4 can comprise glutamic acid at position +95 through isoleucine at position +112. The extracellular portion of CTLA4 can comprise alanine at position +50 through glutamic acid at position +57.

In one embodiment, the soluble CTLA4 mutant molecules comprise one or more mutations (e.g., amino acid substitutions, deletions, or insertions) in the extracellular domain of CTLA4.

For example, the soluble CTLA4 mutant molecules can include a mutation or mutations within or in close proximity to the region encompassed by serine at position +25 through arginine at position +33 (e.g., S25-R33). The mutant CTLA4 molecules can include an amino acid substitution at any one or more of the following positions: S25, P26, G27, K28, A29, T30, E31, or R33.

In another embodiment, the soluble CTLA4 mutant molecules can include a mutation or mutations within or in close proximity to the region encompassed by glutamic acid at position +95 to glycine at position +107 (e.g., E95-G107) The mutant CTLA4 molecules can include an amino acid substitution at any one or more of the following positions: K93, L96, M97, Y98, P99, P100, P101, Y102, Y103, L104, G105, I106, and G107.

Additionally, the invention provides soluble CTLA4 mutant molecules having a mutation or mutations within or in close proximity to the region encompassed by asparagine +108 to isoleucine at position +115 (e.g., N108-I115). The mutant CTLA4 molecule can include an amino acid substitution at any one or more of the following positions: L104, G105, I106, G107, Q111, Y113, or I115. Examples of CTLA4 molecules having mutations in the CTLA4 extracellular domain are included in Tables 2, 3, and 4.

Additionally, the invention provides mutant molecules having one mutation in the extracellular domain of CTLA4. Examples include the following:

| Single-site mutant: | Codon change: |
| --- | --- |
| L104EIg | Glutamic acid GAG |
| L104SIg | Serine AGT |
| L104TIg | Threonine ACG |
| L104AIg | Alanine GCG |
| L104WIg | Tryptophan TGG |
| L104QIg | Glutamine CAG |
| L104KIg | Lysine AAG |
| L104RIg | Arginine CGG |
| L104GIg | Glycine GGG |

Further, the invention provides mutant molecules having two mutations in the extracellular domain of CTLA4. Examples include the following:

| Double-site mutants: | Codon change: |
| --- | --- |
| L104EG105FIg | Phenylalanine TTC |
| L104EG105WIg | Tryptophan TGG |
| L104EG105LIg | Leucine CTT |
| L104ES25RIg | Arginine CGG |
| L104ET32GIg | Glycine GGG |
| L104ET32NIg | Asparagine AAT |
| L104EA29YIg | Tyrosine TAT |
| L104EA29LIg | Leucine TTG |
| L104EA29TIg | Threonine ACT |
| L104EA29WIg | Tryptophan TGG |

Further still, the invention provides mutant molecules having three mutations in the extracellular domain of CTLA4. Examples include the following:

| Triple-site Mutants: | Codon changes: |
| --- | --- |
| L104EA29YS25KIg | Lysine AAA |
| L104EA29YS25KIg | Lysine AAG |
| L104EA29YS25NIg | Asparagine AAC |
| L104EA29YS25RIg | Arginine CGG |

The invention additionally provides soluble CTLA4 mutant molecules comprising an extracellular domain of mutant CTLA4 and a moiety that alters the solubility, affinity and/or valency of the CTLA4 mutant molecule for binding CD80 and/or CD86.

In accordance with a practice of the invention, the moiety can be an immunoglobulin constant region or portion thereof. For in vivo use, it is preferred that the immunoglobulin constant region does not elicit a detrimental immune response in the subject. For example, in clinical protocols, it may be preferred that mutant molecules include human or monkey immunoglobulin constant regions. One example of a suitable immunoglobulin region is human C(gamma)1, comprising the hinge, CH2, and CH3 regions. Other isotypes are possible. Further, other immunoglobulin constant regions are possible (preferably other weakly or non-immunogenic immunoglobulin constant regions). The Ig can have one or more mutations therein, e.g., in the CH2 domain, to reduce effector functions such as CDC or ADCC.

In one embodiment, the soluble CTLA4 mutant molecule comprises the extracellular domain of CTLA4 joined to an immunoglobulin (Ig) portion, wherein the Ig has one or more mutations therein. The Ig portion can include the hinge, CH2, and CH3 regions which can mediate effector function of the soluble CTLA4 mutant molecule, such as binding to Fc receptors, mediating complement-dependent cytotoxicity (e.g., CDC), or mediate antibody-dependent cell-mediated cytotoxicity (e.g., ADCC). The mutation in the immunoglobulin can modulate the binding capability of the immunoglobulin portion to its ligand, such as increase or decrease the binding capability of the immunoglobulin portion to the Fc receptors.

Figure 1:
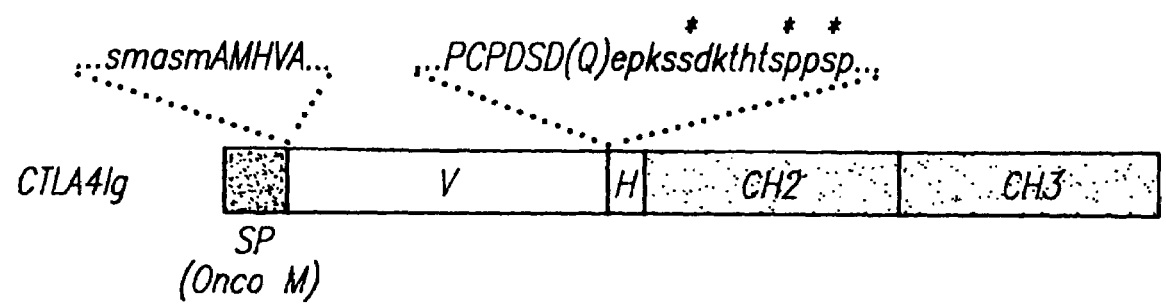
FIG. 1: Shows a schematic representation of a CTLA4Ig fusion construct as described in Example 1, infra.

In a preferred embodiment, the soluble CTLA4 mutant molecule includes the immunoglobulin portion (e.g., hinge, CH2 and CH3 domains), where any or all of the cysteine residues, within the hinge domain are substituted with serine, for example, the cysteines at positions +130, +136, or +139 (FIG. 1 or 22). The mutant molecule may also include the proline at position +148 substituted with a serine, as shown in FIG. 22.

In another preferred embodiment, the soluble CTLA4 mutant molecule includes the immunoglobulin portion (e.g., hinge, CH2 and CH3 domains), having the leucine at position +144 substituted with phenylalanine, the leucine at position +145 substituted with glutamic acid, or glycine at position +147 substituted with alanine.

Other moieties include polypeptide tags. Examples of suitable tags include but are not limited to p97 molecule, env gp120 molecule, E7 molecule, and ova molecule (Dash, B., et al. 1994 *J. Gen. Virol.* 75:1389–97; Ikeda, T., et al. 1994 *Gene* 138:193–6; Falk, K., et al. 1993 *Cell. Immunol.* 150:447–52; Fujisaka, K. et al. 1994 *Virology* 204:789–93). Other molecules are possible (Gerard, C. et al. 1994 *Neuroscience* 62:721; Byrn, R. et al. 1989 63:4370; Smith, D. et al., 1987 *Science* 238:1704; Lasky, L., 1996 *Science* 233: 209).

Soluble CTLA4 mutant molecules can have a junction amino acid residue which is located between the CTLA4 portion and the immunoglobulin portion of the molecule. The junction amino acid can be any amino acid, including glutamine. The junction amino acid can be introduced by molecular or chemical synthesis methods known in the art.

The present invention provides CTLA4 mutant molecules including a signal peptide sequence linked to the N-terminal end of the extracellular domain of the CTLA4 portion of the mutant molecule. The signal peptide can be any sequence that will permit secretion of the mutant molecule, including the signal peptide from oncostatin M (Malik, et al., 1989 *Molec. Cell. Biol.* 9: 2847–2853), or CD5 (Jones, N. H. et al., 1986 *Nature* 323:346–349), or the signal peptide from any extracellular protein.

The invention provides L104EIg (FIG. 23) which is a mutant molecule including a CTLA4 portion encompassing methionine at position +1 through aspartic acid at position +124, a junction amino acid residue glutamine at position +125, and an immunoglobulin portion encompassing glutamic acid at position +126 through lysine at position +357. The portion having the extracellular domain of CTLA4 is mutated so that leucine at position +104 is substituted with glutamic acid. The hinge portion of the mutant molecule is mutated so that the cysteines at positions +130, +136, and +139 are substituted with serine, and the proline at position +148 is substituted with serine. Alternatively, L104EIg can have a CTLA4 portion encompassing alanine at position −1 through aspartic acid at position +124.

The invention provides L104SIg which is a mutant molecule including a CTLA4 portion encompassing methionine at position +1 through aspartic acid at position +124, a junction amino acid residue glutamine at position +125, and an immunoglobulin portion encompassing glutamic acid at position +126 through lysine at position +357. The portion having the extracellular domain of CTLA4 is mutated so that leucine at position +104 is substituted with serine. The hinge portion of the mutant molecule is mutated so that the cysteines at positions +130, +136, and +139 are substituted with serine, and the proline at position +148 is substituted with serine. Alternatively, L104SIg can have a CTLA4 portion encompassing alanine at position −1 through aspartic acid at position +124.

The invention provides L104EA29YIg (FIG. 24) which is a mutant molecule including a CTLA4 portion encompassing methionine at position +1 through aspartic acid at position +124, a junction amino acid residue glutamine at position +125, and the immunoglobulin portion encompassing glutamic acid at position +126 through lysine at position +357. The portion having the extracellular domain of CTLA4 is mutated so that alanine at position +29 is substituted with tyrosine and leucine at position +104 is substituted with glutamic acid. The immunoglobulin portion of the mutant molecule can be mutated, so that the cysteines at positions +130, +136, and +139 are substituted with serine, and the proline at position +148 is substituted with serine. Alternatively, L104EA29YIg can have a CTLA4 portion encompassing alanine at position −1 through aspartic acid at position +124.

The invention provides L104EA29LIg (FIG. 25) which is a mutant molecule including a CTLA4 portion encompassing methionine at position +1 through aspartic acid at position +124, a junction amino acid residue glutamine at position +125, and the immunoglobulin portion encompassing glutamic acid at position +126 through lysine at position +357. The portion having the extracellular domain of CTLA4 is mutated so that alanine at position +29 is substituted with leucine, and leucine at position +104 is substituted with glutamic acid. The immunoglobulin portion of the mutant molecule can be mutated, so that the cysteines at positions +130, +136, and +139 are substituted with serine, and the proline at position +148 is substituted with serine. Alternatively, L104EA29LIg can have a CTLA4 portion encompassing alanine at position −1 through aspartic acid at position +124.

The invention provides L104EA29TIg (FIG. 26) which is a mutant molecule including a CTLA4 portion encompassing methionine at position +1 through aspartic acid at position +124, a junction amino acid residue glutamine at position +125, and the immunoglobulin portion encompassing glutamic acid at position +126 through lysine at position +357. The portion having the extracellular domain of CTLA4 is mutated so that alanine at position +29 is substituted with threonine, and leucine at position +104 is substituted with glutamic acid. The immunoglobulin portion of the mutant molecule can be mutated, so that the cysteines at positions +130, +136, and +139 are substituted with serine, and the proline at position +148 is substituted with serine. Alternatively, L104EA29TIg can have a CTLA4 portion encompassing alanine at position −1 through aspartic acid at position +124.

The invention provides L104EA29WIg (FIG. 27) which is a mutant molecule including a CTLA4 portion encompassing methionine at position +1 through aspartic acid at position +124, a junction amino acid residue glutamine at position +125, and the immunoglobulin portion encompassing glutamic acid at position +126 through lysine at position +357. The portion having the extracellular domain of CTLA4 is mutated so that alanine at position +29 is substituted with tryptophan, and leucine at position +104 is substituted with glutamic acid. The immunoglobulin portion of the mutant molecule can be mutated, so that the cysteines at positions +130, +136, and +139 are substituted with serine, and the proline at position +148 is substituted with serine. Alternatively, L104EA29WIg can have a CTLA4 portion encompassing alanine at position −1 through aspartic acid at position +124.

The invention provides L104EG105FIg which is a mutant molecule including a CTLA4 portion encompassing methionine at position +1 through aspartic acid at position +124, a junction amino acid residue glutamine at position +125, and the immunoglobulin portion encompassing glutamic acid at position +126 through lysine at position +357. The portion having the extracellular domain of CTLA4 is mutated so that leucine at position +104 is substituted with glutamic acid, and glycine at position +105 is substituted with phenylalanine. Alternatively, L104EG105FIg can have a CTLA4 portion encompassing alanine at position −1 through aspartic acid at position +124.

The invention provides L104ES25RIg which is a mutant molecule including a CTLA4 portion encompassing methionine at position +1 through aspartic acid at position +124, a junction amino acid residue glutamine at position +125, and the immunoglobulin portion encompassing glutamic acid at position +126 through lysine at position +357. The portion having the extracellular domain of CTLA4 is mutated so that serine at position +25 is substituted with arginine, and leucine at position +104 is substituted with glutamic acid. Alternatively, L104ES25RIg can have a CTLA4 portion encompassing alanine at position −1 through aspartic acid at position +124.

The invention provides L104EA29YS25KIg which is a mutant molecule including a CTLA4 portion encompassing methionine at position +1 through aspartic acid at position +124, a junction amino acid residue glutamine at position +125, and the immunoglobulin portion encompassing glutamic acid at position +126 through lysine at position +357. The portion having the extracellular domain of CTLA4 is mutated so that serine at position +25 is substituted with lysine, alanine at position +29 is substituted with tyrosine, and leucine at position +104 is substituted with glutamic acid. Alternatively, L104EA29YS25KIg can have a CTLA4 portion encompassing alanine at position −1 through aspartic acid at position +124.

The invention provides L104EA29YS25RIg which is a mutant molecule including a CTLA4 portion encompassing methionine at position +1 through aspartic acid at position +124, a junction amino acid residue glutamine at position +125, and the immunoglobulin portion encompassing glutamic acid at position +126 through lysine at position +357. The portion having the extracellular domain of CTLA4 is mutated so that serine at position +25 is substituted with arginine, alanine at position +29 is substituted with tyrosine, and leucine at position +104 is substituted with glutamic acid. Alternatively, L104EA29YS25RIg can have a CTLA4 portion encompassing alanine at position −1 through aspartic acid at position +124.

The invention further provides nucleic acid molecules comprising nucleotide sequences encoding the amino acid sequences of the soluble CTLA4 mutant molecules of the invention. In one embodiment, the nucleic acid molecule is a DNA (e.g., cDNA) or a hybrid thereof. Alternatively, the nucleic acid molecules are RNA or a hybrid thereof.

Additionally, the invention provides a vector which comprises the nucleotide sequences of the invention. A host vector system is also provided. The host vector system comprises the vector of the invention in a suitable host cell. Examples of suitable host cells include but are not limited to prokaryotic and eukaryotic cells.

The invention further provides methods for producing a protein comprising growing the host vector system of the invention so as to produce the protein in the host and recovering the protein so produced.

CTLA4Ig Codon-Based Mutagenesis

In one embodiment, site-directed mutagenesis and a novel screening procedure were used to identify several mutations in the extracellular domain of CTLA4 that improve binding avidity for CD86, while only marginally altering binding to CD80. In this embodiment, mutations were carried out in residues in serine 25 to arginine 33, the C' strand (alanine 49 and threonine 51), the F strand (lysine 93, glutamic acid 95 and leucine 96), and in methionine 97 through tyrosine 102, tyrosine 103 through glycine 107 and in the G strand at positions glutamine 111, tyrosine 113 and isoleucine 115. These sites were chosen based on studies of chimeric CD28/CTLA4 fusion proteins (J. Exp. Med., 1994, 180: 2049–2058), and on a model predicting which amino acid residue side chains would be solvent exposed, and a lack of amino acid residue identity or homology at certain positions between CD28 and CTLA4. Also, any residue which is spatially in close proximity (5 to 20 Angstrom Units) to the identified residues are considered part of the present invention.

To synthesize and screen soluble CTLA4 mutant molecules with altered affinities for CD86, a two-step strategy was adopted. The experiments entailed first generating a library of mutations at a specific codon of an extracellular portion of CTLA4 and then screening these by BIAcore analysis to identify mutants with altered reactivity to CD80 or CD86.

Methods of Making Compositions of the Invention

Expression of CTLA4 mutant molecules in prokaryotic cells is preferred for some purposes. Prokaryotes most frequently are represented by various strains of bacteria. The bacteria may be a gram positive or a gram negative. Typically, gram-negative bacteria such as *E. coli* are preferred. Other microbial strains may also be used.

Sequences encoding CTLA4 mutant molecules can be inserted into a vector designed for expressing foreign sequences in prokaryotic cells such as *E. coli*. These vectors can include commonly used prokaryotic control sequences which are defined herein to include promoters for transcription initiation, optionally with an operator, along with ribosome binding site sequences, include such commonly used promoters as the beta-lactamase (penicillinase) and lactose (lac) promoter systems (Chang, et al., 1977 *Nature* 198: 1056), the tryptophan (trp) promoter system (Goeddel, et al., 1980 *Nucleic Acids Res.* 8:4057) and the lambda derived $P_L$ promoter and N-gene ribosome binding site (Shimatake, et al., 1981 *Nature* 292:128).

Such vectors will also include origins of replication and selectable markers, such as a beta-lactamase or neomycin phosphotransferase gene conferring resistance to antibiotics so that the vectors can replicate in bacteria and cells carrying the plasmids can be selected for when grown in the presence of ampicillin or kanamycin.

The expression plasmid can be introduced into prokaryotic cells via a variety of standard methods, including but not limited to $CaCl_2$-shock (Cohen, 1972 *Proc. Natl. Acad. Sci. USA* 69:2110, and Sambrook et al. (eds.), "Molecular Cloning: A Laboratory Manual", 2nd Edition, Cold Spring Harbor Press, (1989)) and electroporation.

In accordance with the practice of the invention, eukaryotic cells are also suitable host cells. Examples of eukaryotic cells include any animal cell, whether primary or immortalized, yeast (e.g., *Saccharomyces cerevisiae, Schizosaccharomyces pombe*, and *Pichia pastoris*), and plant cells. Myeloma, COS and CHO cells are examples of animal cells that may be used as hosts. Exemplary plant cells include tobacco (whole plants or tobacco callus), corn, soybean, and rice cells. Corn, soybean, and rice seeds are also acceptable.

Sequences encoding the CTLA4 mutant molecules can be inserted into a vector designed for expressing foreign sequences in a eukaryotic host. The regulatory elements of the vector can vary according to the particular eukaryotic host.

Commonly used eukaryotic control sequences include promoters and control sequences compatible with mammalian cells such as, for example, CMV promoter (CDM8 vector) and avian sarcoma virus (ASV) (πLN vector). Other commonly used promoters include the early and late promoters from Simian Virus 40 (SV40) (Fiers, et al., 1973 *Nature* 273:113), or other viral promoters such as those derived from polyoma, Adenovirus 2, and bovine papilloma virus. An inducible promoter, such as hMTII (Karin, et al., 1982 *Nature* 299:797–802) may also be used.

Vectors for expressing CTLA4 mutant molecules in eukaryotes may also carry sequences called enhancer regions. These are important in optimizing gene expression and are found either upstream or downstream of the promoter region.

Sequences encoding CTLA4 mutant molecules can integrate into the genome of the eukaryotic host cell and replicate as the host genome replicates. Alternatively, the vector carrying CTLA4 mutant molecules can contain origins of replication allowing for extrachromosomal replication.

For expressing the sequences in *Saccharomyces cerevisiae*, the origin of replication from the endogenous yeast plasmid, the 2μ circle could be used. (Broach, 1983 *Meth. Enz.* 101:307). Alternatively, sequences from the yeast genome capable of promoting autonomous replication could be used (see, for example, Stinchcomb et al., 1979 *Nature* 282:39); Tschemper et al., 1980 *Gene* 10:157; and Clarke et al., 1983 *Meth. Enz.* 101:300).

Transcriptional control sequences for yeast vectors include promoters for the synthesis of glycolytic enzymes (Hess et al., 1968 *J Adv. Enzyme Reg.* 7:149; Holland et al., 1978 *Biochemistry* 17:4900). Additional promoters known in the art include the CMV promoter provided in the CDM8 vector (Toyama and Okayama, 1990 *FEBS* 268:217–221); the promoter for 3-phosphoglycerate kinase (Hitzeman et al., 1980 *J. Biol. Chem.* 255:2073), and those for other glycolytic enzymes.

Other promoters are inducible because they can be regulated by environmental stimuli or the growth medium of the cells. These inducible promoters include those from the genes for heat shock proteins, alcohol dehydrogenase 2, isocytochrome C, acid phosphatase, enzymes associated with nitrogen catabolism, and enzymes responsible for maltose and galactose utilization.

Regulatory sequences may also be placed at the 3' end of the coding sequences. These sequences may act to stabilize messenger RNA. Such terminators are found in the 3' untranslated region following the coding sequences in several yeast-derived and mammalian genes.

Exemplary vectors for plants and plant cells include but are not limited to *Agrobacterium* $T_i$ plasmids, cauliflower mosaic virus (CaMV), tomato golden mosaic virus (TGMV).

General aspects of mammalian cell host system transformations have been described by Axel (U.S. Pat. No. 4,399,216 issued Aug. 16, 1983). Mammalian cells can be transformed by methods including but not limited to, transfection in the presence of calcium phosphate, microinjection, electroporation, or via transduction with viral vectors.

Methods for introducing foreign DNA sequences into plant and yeast genomes include (1) mechanical methods, such as microinjection of DNA into single cells or protoplasts, vortexing cells with glass beads in the presence of DNA, or shooting DNA-coated tungsten or gold spheres into cells or protoplasts; (2) introducing DNA by making protoplasts permeable to macromolecules through polyethylene glycol treatment or subjection to high voltage electrical pulses (electroporation); or (3) the use of liposomes (containing cDNA) which fuse to protoplasts.

Expression of CTLA4 mutant molecules can be detected by methods known in the art. For example, the mutant molecules can be detected by Coomassie staining SDS-PAGE gels and immunoblotting using antibodies that bind CTLA4. Protein recovery can be performed using standard protein purification means, e.g., affinity chromatography or ion-exchange chromatography, to yield substantially pure product (R. Scopes in: "Protein Purification, Principles and Practice", Third Edition, Springer-Verlag 1994).

The soluble CTLA4 mutant molecule can be isolated by molecular or chemical synthesis methods. The molecular methods may include the following steps: introducing a suitable host cell with a nucleic acid molecule that expresses and encodes the soluble CTLA4 mutant molecule; culturing the host cell so introduced under conditions that permit the host cell to express the mutant molecules; and isolating the expressed mutant molecules. The signal peptide portion of the mutant molecule permits the expressed protein molecules to be secreted by the host cell. The secreted mutant molecules can undergo post-translational modification, involving cleavage of the signal peptide to produce a mature protein having the CTLA4 and the immunoglobulin portions. The cleavage may occur after the alanine at position −1, resulting in a mature mutant molecule having methionine at position +1 as the first amino acid (FIG. 22). Alternatively, the cleavage may occur after the methionine at position −2, resulting in a mature mutant molecule having alanine at position −1 as the first amino acid.

Making Monoclonal Antibodies of the Invention

Monoclonal antibodies reactive with CTLA4 mutant molecules, may be produced by hybridomas prepared using known procedures, such as those introduced by Kohler and Milstein (Kohler and Milstein, *Nature*, 256:495–97 (1975)), and modifications thereof, to regulate cellular interactions.

These techniques involve the use of an animal which is primed to produce a particular antibody. The animal can be primed by injection of an immunogen (e.g. a soluble CTLA4 mutant molecule) to elicit the desired immune response, i.e. production of antibodies from the primed animal. Lymphocytes derived from the lymph nodes, spleens or peripheral blood of primed, diseased animals can be used to search for a particular antibody. The lymphocyte chromosomes encoding desired immunoglobulins are immortalized by fusing the lymphocytes with myeloma cells, generally in the presence of a fusing agent such as polyethylene glycol (PEG). Any of a number of myeloma cell lines may be used as a fusion partner according to standard techniques; for example, the P3-NS1/1-Ag4-1, P3-x63-Ag8.653, Sp2/0-Ag14, or HL1–653 myeloma lines. These myeloma lines are available from the ATCC, Manassas, Md.

The resulting cells, which include the desired hybridomas, are then grown in a selective medium such as HAT medium, in which unfused parental myeloma or lymphocyte cells eventually die. Only the hybridoma cells survive and can be grown under limiting dilution conditions to obtain isolated clones. The supernatants of the hybridomas are screened for the presence of antibodies of the desired specificity, e.g. by immunoassay techniques using the CTLA4 mutant molecule that has been used for immunization. Positive clones can then be subcloned under limiting dilution conditions, and the monoclonal antibody produced can be isolated.

Various conventional methods can be used for isolation and purification of the monoclonal antibodies so as to obtain them free from other proteins and contaminants. Commonly used methods for purifying monoclonal antibodies include ammonium sulfate precipitation, ion exchange chromatography, and affinity chromatography (Zola et al., in *Monoclonal Hybridoma Antibodies: Techniques and Applications*, Hurell (ed.) pp. 51–52 (CRC Press, 1982)). Hybridomas produced according to these methods can be propagated in vitro or in vivo (in ascites fluid) using techniques known in the art (Fink et al., *Prog. Clin. Pathol.*, 9:121–33 (1984)).

Generally, the individual cell line may be propagated in vitro, for example, in laboratory culture vessels, and the culture medium containing high concentrations of a single specific monoclonal antibody can be harvested by decantation, filtration, or centrifugation.

In addition, fragments of these antibodies containing the active binding region reactive with the extracellular domain of CTLA4 mutant molecule, such as Fab, $F(ab')_2$ and Fv fragments may be produced. Such fragments can be produced using techniques well established in the art (e.g. Rousseaux et al., in *Methods Enzymol.*, 121:663–69, Academic Press (1986)).

Methods for Using the Compositions of the Invention

Additionally, the invention provides methods for regulating functional CTLA4- and CD28-positive T cell interactions with CD80- and/or CD86-positive cells. The methods comprise contacting the CD80- and/or CD86-positive cells with a soluble CTLA4 mutant molecule of the invention thereby regulating functional CTLA4 and/or CD28 T cell interactions with CD80-and/or CD86-positive cells. In one embodiment of the invention, the soluble CTLA4 mutant molecule is a fusion protein that contains at least a portion of the extracellular domain of mutant CTLA4. In another embodiment, the soluble CTLA4 mutant molecule comprises: a first amino acid sequence including the extracellular domain of CTLA4 from methionine at position +1 to aspartic acid at position +124, including at least one mutation; and a second amino acid sequence including the hinge, CH2, and CH3 regions of the human immunoglobulin gamma 1 molecule (FIG. 3 or 22).

The present invention further provides a method for treating immune system diseases (also referred to herein as immunoproliferative diseases) mediated by CD28- and/or CTLA4-positive cell interactions with CD80/CD86-positive cells. In one embodiment, T cell interactions are inhibited.

This method comprises administering to a subject the soluble CTLA4 mutant molecules of the invention to regulate T cell interactions with the CD80- and/or CD86-positive cells.

The present invention also provides method for inhibiting graft versus host disease in a subject. This method comprises administering to the subject a soluble CTLA4 mutant molecule of the invention.

The invention encompasses the use of the soluble CTLA4 mutant molecules together with other immunosuppressants, e.g., cyclosporin (Mathiesen, in: "Prolonged Survival and Vascularization of Xenografted Human Glioblastoma Cells in the Central Nervous System of Cyclosporin A-Treated Rats" 1989 *Cancer Lett.*, 44:151–156), prednisone, azathioprine, and methotrexate (R. Handschumacher "Chapter 53: Drugs Used for Immunosuppression" pages 1264–1276). Other immunosuppressants are possible.

CTLA4 mutant molecules may be used to react with CD80 or CD86 positive cells, such as B cells, to regulate immune responses mediated by T cell interactions with the B7 antigen positive cells or in vitro for leukocyte typing so as to define B cell maturational stages and/or B cell associated diseases (Yokochi et al. J. Immuno. 128(2):823. Surface immunostaining of leukocytes is accomplished by immunofluorescent technology or immunoenzymatic methods but other means of detection are possible.

Soluble CTLA4 mutant molecules may also be used to react with B7 positive cells, including B cells, to regulate immune responses mediated by T cell dependent B cell responses. The B7 antigen expressed on activated B cells and cells of other lineages, and the CD28 receptor expressed on T cells, can directly bind to each other, and this interaction can mediate cell—cell interaction. Such interactions directly trigger the CD28/B7 activation pathway in T cells, leading to cytokine production, T cell proliferation, and B cell differentiation into immunoglobulin producing cells. The activation of B cells that occurs, can cause increased expression of B7 antigen and further CD28 stimulation, leading to a state of chronic inflammation such as in autoimmune diseases, allograft rejection, graft versus host disease or chronic allergic reactions. Blocking or inhibiting this reaction may be effective in preventing T cell cytokine production and T/B cell proliferation and thus preventing or reversing inflammatory reactions.

Soluble CTLA4 mutant molecule can be a potent inhibitor of in vitro lymphocyte functions requiring T and B cell interaction. This indicates the importance of interactions between the B7 antigen and its counter-receptors, CTLA4 and/or CD28.

The soluble CTLA4 mutant molecules are expected to exhibit inhibitory properties in vivo. Under conditions where T cell/B cell interactions are occurring as a result of contact between T cells and B cells, binding of introduced CTLA4 mutant molecules to react with B7 antigen positive cells, for example B cells, may interfere, i.e. inhibit, the T cell/B cell interactions resulting in regulation of immune responses. Because of this exclusively inhibitory effect, CTLA4 mutant molecule is expected to be useful in vivo as an inhibitor of T cell activity, over non-specific inhibitors such as cyclosporine and glucosteroids.

In one embodiment, the CTLA4 mutant molecules may be introduced in a suitable pharmaceutical carrier in vivo, i.e. administered into a subject, e.g., a human subject, for treatment of pathological conditions such as immune system diseases or cancer.

Introduction of CTLA4 mutant molecules in vivo is expected to result in interference with T cell interactions with other cells, such as B cells, as a result of binding of the ligand to B7 positive cells. The prevention of normal T cell interactions may result in decreased T cell activity, for example, decreased T cell proliferation or alter cytokine production.

Under some circumstances, as noted above, the effect of administration of the CTLA4 mutant molecules in vivo is inhibitory, resulting from blocking by CTLA4 mutant molecules and CD28 triggering resulting from T cell/B cell contact. For example, the CTLA4 mutant molecules may block T cell proliferation. Introduction of the CTLA4 mutant molecules in vivo will thus produce effects on both T and B cell-mediated immune responses. The mutant molecules may also be administered to a subject in combination with the introduction of cytokines or other therapeutic reagents.

In an additional embodiment of the invention, other reagents, including derivatives reactive with the CTLA4 mutant molecules are used to regulate T cell interactions. For example, antibodies, and/or antibody fragments reactive with the CTLA4 mutant molecules can be screened to identify those capable of inhibiting the binding of the CTLA4 mutant molecules to CD80 or CD86. The antibodies or antibody fragments such as Fab or F(ab')$_2$ fragments, may then be used to react with the T cells, for example, to inhibit T cell proliferation.

In another embodiment, the CTLA4 mutant molecules may be used to identify additional compounds capable of regulating the interaction between CTLA4 and CD80 or CD86. Such compounds may include small naturally occurring molecules that can be used to react with B cells and/or T cells. For example, fermentation broths may be tested for the ability to inhibit CTLA4/B7 interactions.

The CD28-mediated T cell proliferation pathway is cyclosporine-resistant, in contrast to proliferation driven by the CD3/Ti cell receptor complex (June et al., 1987, supra). Cyclosporine is relatively ineffective as a treatment for GVH disease (Storb, *Blood* 68:119–125 (1986)). GVH disease is thought to be mediated by T lymphocytes which express CD28 antigen (Storb and Thomas, *Immunol. Rev.* 88:215–238 (1985)). Thus, the CTLA4 mutant molecules may be useful alone, or in combination with immunosuppressants such as cyclosporine, for blocking T cell proliferation in GVH disease.

Regulation of CTLA4-positive T cell interactions with B7 positive cells, including B cells, by the methods of the invention may thus be used to treat pathological conditions such as autoimmunity, transplantation, infectious diseases and neoplasia.

The B7-binding molecules described herein may be in a variety of dosage forms which include, but are not limited to, liquid solutions or suspensions, tablets, pills, powders, suppositories, polymeric microcapsules or microvesicles, liposomes, and injectable or infusible solutions. The preferred form depends upon the mode of administration and the therapeutic application.

The most effective mode of administration and dosage regimen for the molecules of the present invention depends upon the severity and course of the disease, the subject's health and response to treatment and the judgment of the treating physician. Accordingly, the dosages of the molecules should be titrated to the individual subject.

The interrelationship of dosages for animals of various sizes and species and humans based on mg/m$^2$ of surface area is described by Freireich, E. J., et al. (Quantitative Comparison of Toxicity of Anticancer Agents in Mouse, Rat, Hamster, Dog, Monkey and Man. Cancer Chemother, Rep., 50, No. 4, 219–244, May 1966).

Adjustments in the dosage regimen may be made to optimize the growth inhibiting response. Doses may be divided and administered on a daily basis or the dose may be reduced proportionally depending upon the situation. For example, several divided doses may be administered daily or the dose may be proportionally reduced as indicated by the specific therapeutic situation.

In accordance with the practice of the invention an effective amount for treating a subject may be between about 0.1 and about 10 mg/kg body weight of subject. Also, the effective amount may be an amount between about 1 and about 10 mg/kg body weight of subject.

The CTLA4 mutant molecules of the invention also have in vitro clinical application. They may be useful in the enumeration of B7 positive cells in the diagnosis or prognosis of some conditions of immunodeficiency, the phenotyping of leukemias and lymphomas, and the monitoring of immunological change following organ transplantation.

ADVANTAGES OF THE PRESENT INVENTION

The discovery of additional CTLA4 mutants are important because they can be important immunosuppressive agents or tools to combat disease. Additionally, soluble CTLA4 mutant molecules having a higher avidity for CD80- or CD86-positive cells compared to wild type CTLA4 have an advantage over wildtype CTLA4 molecules because they are expected to block the priming of antigen specific activated cells with higher efficiency than wild type.

Further, production costs for CTLA4Ig are very high. The high avidity mutant CTLA4Ig molecules having higher potent immunosuppressive properties could be used in the clinic at considerably lower doses than non-mutated CTLA4Ig to achieve similar levels of immunosuppression. Soluble CTLA4 mutant molecules, e.g., L104EA29YIg, could be very cost effective.

The following example is presented to illustrate the present invention and to assist one of ordinary skill in making and using the same. This example is not intended in any way to otherwise limit the scope of the invention.

EXAMPLE 1

The following provides a description of the methods used to generate a nucleotide sequence encoding the CTLA4Ig fusion protein.

Preparation of CTLA4Ig Fusion Protein

A genetic construct encoding CTLA4Ig between the extracellular domain of CTLA4 and an IgCgamma1 domain was constructed in a manner similar to that described above for the CD28Ig construct. The extracellular domain of the CTLA4 gene was cloned by PCR using synthetic oligonucleotides corresponding to the published sequence (Dariavach et al., *Eur. Journ. Immunol.* 18:1901–1905 (1988)).

Because a signal peptide for CTLA4 was not identified in the CTLA4 gene, the N-terminus of the predicted sequence of CTLA4 was fused to the signal peptide of oncostatin M (Malik et al., *Mol. and Cell. Biol.* 9:2847 (1989)) in two steps using overlapping oligonucleotides. For the first step, the oligonucleotide, CTCAGTCTGGTCCTTGCACTC-CTG TTTCCAAGCATGGCGAGCATGGCAATG-CACGTGGCCCAGCC (SEQ ID NO.: 21) (which encoded the C terminal 15 amino acids from the oncostatin M signal peptide fused to the N terminal 7 amino acids of CTLA4) was used as forward primer, and TTTGGGCTCCTGATCA-GAATCTGGGCACGGTTG (SEQ ID NO.: 22) (encoding amino acid residues 119–125 of the amino acid sequence encoding CTLA4 receptor and containing a Bcl I restriction enzyme site) as reverse primer. The template for this step was cDNA synthesized from 1 micro g of total RNA from H38 cells (an HTLV II infected T cell leukemic cell line provided by Drs. Salahudin and Gallo, NCI, Bethesda, Md.). A portion of the PCR product from the first step was reamplified, using an overlapping forward primer, encoding the N terminal portion of the oncostatin M signal peptide and containing a Hind III restriction endonuclease site, CTAGC-CACTGAAGCTTCACCAATGGGTGTACT-GCTCACACAGAGGACGCTGCT CAGTCTGGTCCT-TGCACTC (SEQ ID NO.: 23) and the same reverse primer. The product of the PCR reaction was digested with Hind III and Bcl I and ligated together with a Bcl I/Xba I cleaved cDNA fragment encoding the amino acid sequences corresponding to the hinge, CH2 and CH3 regions of IgCγ1 into the Hind III/Xba I cleaved expression vector, CDM8 or Hind III/Xba I cleaved expression vector pLN.

A schematic map of the resulting CTLA4Ig fusion construct is shown in FIG. 1. Sequences displayed in this figure show the junctions between CTLA4 (upper case letters, unshaded regions) and the signal peptide, SP, of oncostatin M (dark shaded regions), and the hinge, H, of IgC(gamma)1 (stippled regions). The amino acid in parentheses was introduced during construction. Asterisks (*) indicate cysteine to serine mutations introduced in the IgCγ hinge region. The immunoglobulin superfamily V-like domain present in CTLA4 is indicated, as are the CH2 and CH3 domains of IgC(gamma)1.

Expression plasmids, CDM8, containing CTLA4Ig were then transfected into COS cells using DEAE/dextran transfection by modification (Linsley et al., 1991, supra) of the protocol described by Seed and Aruffo, 1987, supra.

Expression plasmid constructs (pi LN or CDM8) containing cDNA encoding the amino acid sequence of CTLA4Ig, was transfected by lipofection using standard procedures into dhfr⁻ CHO lines to obtain novel cell lines stably expressing CTLA4Ig.

DNA encoding the amino acid sequence corresponding to CTLA4Ig has been deposited with the ATCC under the Budapest Treaty on May 31, 1991, and has been accorded ATCC accession number 68629.

A preferred stable transfectant, expressing CTLA4Ig, designated Chinese Hamster Ovary Cell Line, CTLA4Ig-24, was made by screening B7 positive CHO cell lines for B7 binding activity in the medium using immunostaining. Transfectants were maintained in DMEM supplemented with 10% fetal bovine serum (FBS), 0.2 mM proline and 1 micro M methotrexate.

The CTLA4Ig-24 CHO cell line has been deposited with the ATCC under the Budapest Treaty on May 31, 1991 and has been accorded accession number ATCC 10762.

CTLA4Ig was purified by protein A chromatography from serum-free conditioned supernatants (FIG. 2). Concentrations of CTLA4Ig were determined assuming an extinction coefficient at 280 nm of 1.6 (experimentally determined by amino acid analysis of a solution of known absorbance). Molecular weight standards (lanes 1 and 3, FIG. 2) and samples (1 micro grams) of CTLA4Ig (lanes 2 and 4) were subjected to SDS-PAGE (4–12% acrylamide gradient) under non-reducing conditions (- beta ME, lanes 1 and 2) or reducing conditions (+beta ME, lanes 3 and 4) Proteins were visualized by staining with Coomassie Brilliant Blue.

Under non-reducing conditions, CTLA4Ig migrated as a $M_r$ approximately 100,000 species, and under reducing conditions, as a $M_r$ approximately 50,000 species (FIG. 2).

Because the IgC (gamma) hinge disulfides were eliminated during construction, CTLA4Ig, like CD28Ig, is a dimer presumably joined through a native disulfide linkage.

EXAMPLE 2

The following provides a description of the methods used to generate the nucleotide sequence encoding the CTLA4 receptor.

CTLA4 Receptor

To reconstruct DNA encoding the amino acid sequence corresponding to the full length human CTLA4 gene, cDNA encoding amino acids corresponding to a fragment of the transmembrane and cytoplasmic domains of CTLA4 was cloned by PCR and then joined with cDNA encoding amino acids corresponding to a fragment from CTLA4Ig that corresponded to the oncostatin M signal peptide fused to the N-terminus of CTLA4. Procedures for PCR, and cell culture and transfections were as described above in Example 1 using COS cells and DEAE-dextran transfection.

Because the expression of CTLA4 receptor protein in human lymphoid cells has not been previously reported, it was necessary to locate a source of CTLA4 mRNA. cDNA was reverse transcribed from the total cellular RNA of H38 cells, as noted above, was used for cloning by PCR. For this purpose, the oligonucleotide, GCAATGCACGTGGC-CCAGCCTGCTGTGGTAGTG (SEQ ID NO.: 24) (encoding the first 11 amino acids in the predicted coding sequence) was used as a forward primer, and TGATGTAA-CATGTCTAGATCAATTGATGG-GAATAAAATAAGGCTG (SEQ ID NO.: 25) (homologous to the last 8 amino acids in CTLA4 and containing a Xba I site) as reverse primer. The template again was a cDNA synthesized from 1 micro gram RNA from H38 cells. Products of the PCR reaction were cleaved with the restriction endonucleases Nco I and Xba I and the resulting 316 bp product was gel purified. A 340 bp Hind III/Nco I fragment from the CTLAIg fusion described above was also gel-purified, and both restriction fragments were ligated into Hind III/Xba I cleaved CDM8 to form OMCTLA.

The resulting construct corresponded to full length CTLA4 and the oncostatin M signal peptide. The nucleotide sequence of the construct is shown in FIG. 3 and was designated OMCTLA4. The sequence for CTLA4 shown in FIG. 3 differs from the predicted human CTLA4 DNA sequence (Dariavach et al., supra) by a base change such that the previously reported alanine at amino acid position 110 of the amino acid sequence shown, encodes a threonine. This threonine is part of a newly identified N-linked glycosylation site that may be important for successful expression of the fusion protein.

Ligation products were transformed into MC1061/p3 *E. coli* cells and colonies were screened for the appropriate plasmids. Sequences of the resulting constructs were confirmed by DNA sequence analysis.

EXAMPLE 3

The following provides a description of the methods used to generate the nucleotide sequences encoding the B7Ig and CD28Ig fusion proteins.

Preparation of B7Ig and CD28Ig Fusion Proteins

Receptor-immunoglobulin C gamma (IgCγ) fusion proteins B7Ig and CD28Ig were prepared as described by Linsley et al., in *J. Exp. Med.* 173:721–730 (1991), incorporated by reference herein. Briefly, DNA encoding amino acid sequences corresponding to the respective receptor protein (e.g. B7) was joined to DNA encoding amino acid sequences corresponding to the hinge, CH2 and CH3 regions of human IgCγ1. This was accomplished as follows.

Polymerase Chain Reaction (PCR). For PCR, DNA fragments were amplified using primer pairs as described below for each fusion protein. PCR reactions (0.1 ml final volume) were run in Taq polymerase buffer (Stratagene, La Jolla, Calif.), containing 20 micro moles each of dNTP; 50–100 pmoles of the indicated primers; template (1 ng plasmid or cDNA synthesized from ≦1 micro gram total RNA using random hexamer primer, as described by Kawasaki in PCR Protocols, Academic Press, pp. 21–27 (1990), incorporated by reference herein); and Taq polymerase (Stratagene). Reactions were run on a thermocycler (Perkin Elmer Corp., Norwalk, Conn.) for 16–30 cycles (a typical cycle consisted of steps of 1 min at 94 degrees C., 1–2 min at 50 degrees C. and 1–3 min at 72 degrees C.).

Plasmid Construction. Expression plasmids containing cDNA encoding CD28, (as described by Aruffo and Seed, *Proc. Natl. Acad. Sci. USA* 84:8573 (1987)), were provided by Drs. Aruffo and Seed (Mass General Hospital, Boston, Mass.). Plasmids containing cDNA encoding CD5, (as described by Aruffo, *Cell* 61:1303 (1990)), were provided by Dr. Aruffo. Plasmids containing cDNA encoding B7, (as described by Freeman et al., *J. Immunol.* 143:2714 (1989)), were provided by Dr. Freeman (Dana Farber Cancer Institute, Boston, Mass.). For initial attempts at expression of soluble forms of CD28 and B7, constructs were made (OMCD28 and OMB7) as described by Linsley et al., *J. Exp. Med.*, supra, in which stop codons were introduced upstream of the transmembrane domains and the native signal peptides were replaced with the signal peptide from oncostatin M (Malik et al., *Mol. Cell Biol.* 9:2847 (1989)). These were made using synthetic oligonucleotides for reconstruction (OMCD28) or as primers (OMB7) for PCR. OMCD28, is a CD28 cDNA modified for more efficient expression by replacing the signal peptide with the analogous region from oncostatin M. CD28Ig and B7Ig fusion constructs were made in two parts. The 5' portions were made using OMCD28 and OMB7 as templates and the oligonucleotide, CTAGCCACTGAAGCTTCACCATGGGTG-TACTGCTCACAC (SEQ ID NO.: 26) (encoding the amino acid sequence corresponding to the oncostatin M signal peptide) as a forward primer, and either TGGCATGGGCTC-CTGATCAGGCTTAGAAGGTCCGGGAAA (SEQ ID NO.: 27) or, TTTGGGCTCCTGATCAGGAAAATGCTCT-TGCTTGGTTGT (SEQ ID NO.: 28) as reverse primers, respectively. Products of the PCR reactions were cleaved with restriction endonucleases (Hind III and BclI) as sites introduced in the PCR primers and gel purified.

The 3' portion of the fusion constructs corresponding to human IgCγ1 sequences was made by a coupled reverse transcriptase (from Avian myeloblastosis virus; Life Sciences Associates, Bayport, N.Y.)-PCR reaction using RNA from a myeloma cell line producing human-mouse chimeric mAb L6 (provided by Dr. P. Fell and M. Gayle, Bristol-Myers Squibb Company, Pharmaceutical Research Institute, Seattle, Wash.) as template. The oligonucleotide, AAG-CAAGAGCATTTTCCTGATCAGGAGC-CCAAATCTTCTGACAAAACTCACA CATCCCCAC-CGTCCCCAGCACCTGAACTCCTG (SEQ ID NO.: 29) was used as forward primer, and CTTCGACCAGTCTA-GAAGCATCCTCGTGCGACCGCGAGAGC (SEQ ID NO.: 30) as reverse primer. Reaction products were cleaved with BclI and XbaI and gel purified. Final constructs were assembled by ligating HindIII/BclI cleaved fragments containing CD28 or B7 sequences together with BclI/XbaI cleaved fragment containing IgCγ1 sequences into HindIII/XbaI cleaved CDM8. Ligation products were transformed into MC1061/p3 *E. coli* cells and colonies were screened for the appropriate plasmids. Sequences of the resulting constructs were confirmed by DNA sequencing.

The construct encoding B7 contained DNA encoding amino acids corresponding to amino acid residues from approximately position 1 to approximately position 215 of the extracellular domain of B7. The construct encoding CD28 contained DNA encoding amino acids corresponding to amino acid residues from approximately position 1 to approximately position 134 of the extracellular domain of CD28.

CD5Ig was constructed in identical fashion, using CAT-TGCACAGTCAAGCTTCCATGC-CCATGGGTTCTCTGGCCACCTTG (SEQ ID NO.: 31) as forward primer and ATCCACAGTGCAGTGATCATTTG-GATCCTGGCATGTGAC (SEQ ID NO.: 32) as reverse primer. The PCR product was restriction endonuclease digested and ligated with the IgCγ 1 fragment as described above. The resulting construct (CD5Ig) encoded a mature protein having an amino acid sequence containing amino acid residues from position 1 to position 347 of the sequence corresponding to CD5, two amino acids introduced by the construction procedure (amino acids DQ), followed by DNA encoding amino acids corresponding to the IgCγ 1 hinge region.

Cell Culture and Transfections. COS (monkey kidney cells) were transfected with expression plasmids expressing CD28 and B7 using a modification of the protocol of Seed and Aruffo (*Proc. Natl. Acad. Sci.* 84:3365 (1987)), incorporated by reference herein. Cells were seeded at $10^6$ per 10 cm diameter culture dish 18–24 h before transfection. Plasmid DNA was added (approximately 15 micro grams/dish) in a volume of 5 mls of serum-free DMEM containing 0.1 mM chloroquine and 600 micro grams/mil DEAE Dextran, and cells were incubated for 3–3.5 h at 37 degrees C. Transfected cells were then briefly treated (approximately 2 min) with 10% dimethyl sulfoxide in PBS and incubated at 37 degrees C. for 16–24 h in DMEM containing 10% FCS. At 24 h after transfection, culture medium was removed and replaced with serum-free DMEM (6 ml/dish). Incubation was continued for 3 days at 37 degrees C., at which time the spent medium was collected and fresh serum-free medium was added. After an additional 3 days at 37 degrees C., the spent medium was again collected and cells were discarded.

CHO cells expressing CD28, CD5 or B7 were isolated as described by Linsley et al., (1991) supra, as follows: Briefly, stable transfectants expressing CD28, CD5, or B7, were isolated following cotransfection of dihydrofolate reductase-deficient Chinese hamster ovary (dhfr⁻ CHO) cells with a mixture of the appropriate expression plasmid and the selectable marker, pSV2dhfr (Linsley et al., *Proc. Natl. Acad. Sci. USA* 87:5031 (1990)), incorporated by reference herein. Transfectants were then grown in increasing concentrations of methotrexate to a final level of 1 micro M and were maintained in DMEM supplemented with 10% fetal bovine serum (FBS), 0.2 mM proline and 1 micro M methotrexate. CHO lines expressing high levels of CD28 (CD28 CHO) or B7 (B7⁺ CHO) were isolated by multiple rounds of fluorescence-activated cell sorting (FACS$^R$) following indirect immunostaining with mAbs 9.3 or BB-1. Amplified CHO cells negative for surface expression of CD28 or B7 (dhfr⁺ CHO) were also isolated by FACS$^R$ from CD28-transfected populations.

Immunostaining and FACS$^R$ Analysis. Transfected CHO or COS cells or activated T cells were analyzed by indirect immunostaining. Before staining, CHO cells were removed from their culture vessels by incubation in PBS containing 10 mM EDTA. Cells were first incubated with murine mAbs 9.3 (Hansen et al., *Immunogenetics* 10:247 (1980)) or BB-1 (Yokochi et al., *J. Immunol.* 128:823 (1981)), or with Ig fusion proteins (all at 10 micro grams/ml in DMEM containing 10% FCS) for 1–2 h at 4° C. Cells were then washed, and incubated for an additional 0.5–2 h at 4° C. with a FITC-conjugated second step reagent (goat anti-mouse Ig serum for murine mAbs, or goat anti-human Ig Cγ serum for fusion proteins (Tago, Inc., Burlingame, Calif.)). Fluorescence was analyzed on a FACS IV$^R$ cell sorter (Becton Dickinson and CO., Mountain View, Calif.) equipped with a four decade logarithmic amplifier.

Purification of Ig Fusion Proteins. The first, second and third collections of spent serum-free culture media from transfected COS cells were used as sources for the purification of Ig fusion proteins. After removal of cellular debris by low speed centrifugation, medium was applied to a column (approximately 200–400 ml medium/ml packed bed volume) of immobilized protein A (Repligen Corp., Cambridge, Mass.) equilibrated with 0.05 M sodium citrate, pH 8.0 After application of the medium, the column was washed with 1 M potassium phosphate, pH 8, and bound protein was eluted with 0.05 M sodium citrate, pH 3. Fractions were collected and immediately neutralized by addition of 1/10 volume of 2 M Tris, pH 8. Fractions containing the peak of $A_{280}$ absorbing material were pooled and dialyzed against PBS before use. Extinction coefficients of 2.4 and 2.8 ml/mg for CD28Ig and B7Ig, respectively, were determined by amino acid analysis of solutions of known absorbance. The recovery of purified CD28Ig and B7Ig binding activities was nearly quantitative as judged by FACS$^R$ analysis after indirect fluorescent staining of B7⁺ and CD28⁺ CHO cells.

EXAMPLE 4

The following provides a description of the methods used to characterize CTLA4Ig.

Characterization of CTLA4 µl

To characterize the CTLA4Ig constructs, several isolates, CD28Ig, B7Ig, and CD5Ig, were prepared as described above and were transfected into COS cells as described in Examples 2 and 3, and were tested by FACS$^R$ analysis for binding of B7Ig. In addition to the above-mentioned constructs, CDM8 plasmids containing cDNAs encoding CD7 as described by Aruffo and Seed, (*EMBO Jour.* 6:3313–3316 (1987)), incorporated by reference herein, were also used.

mAbs. Murine monoclonal antibodies (mAbs) 9.3 (anti-CD28) and G19-4 (anti-CD3, G3–7 (anti-CD7), BB-1 (anti-B7 antigen) and rat mAb 187.1 (anti-mouse kappa chain) have been described previously (Ledbetter et al., *Proc. Natl. Acad. Sci.* 84:1384–1388 (1987); Ledbetter et al., *Blood* 75:1531 (1990); Yokochi et al., supra) and were purified from ascites before use. The hybridoma producing mAb OKT8 was obtained from the ATCC, Rockville, Md., and the mAb was also purified from ascites before use. mAb 4G9 (anti-CD19) was provided by Dr. E. Engleman, Stanford University, Palo Alto, Calif.). Purified human-mouse chimeric mAb L6 (having human Cγ1 Fc portion) was a gift of Dr. P. Fell and M. Gayle (Bristol-Myers Squibb Pharmaceutical Research Institute, Seattle, Wash.)

Immunostaining and FACS$^R$ Analysis. Prior to staining, COS or CHO cells were removed from their culture vessels by incubation in PBS containing 10 mM EDTA. Cells were first incubated with mAbs or Ig fusion proteins at 10 micro grams/ml in DMEM containing 10% FBS for 1–2 hr at 4 degrees C. Cells were then washed, and incubated for an additional 0.5–2 hrs at 4 degrees C. with FITC-conjugated goat anti-mouse immunoglobulin or with FITC-conjugated goat anti-human IgCγ serum (both from Tago, Burlingame, Calif.). When binding of both mAbs and Ig fusion proteins were measured in the same experiment, FITC-conjugated anti-mouse and anti-human second step reagents were mixed together before use. Fluorescence on a total of 10,000 cells was then analyzed by FACS$^R$.

Peripheral Blood Lymphocyte Separation and Stimulation. Peripheral blood lymphocytes (PBLs) were isolated by centrifugation through Lymphocyte Separation Medium (Litton Bionetics, Kensington, Md.). Alloreactive T cells were isolated by stimulation of PBL in a primary mixed lymphocyte reaction (MLR). PBL were cultured at $10^6$/ml irradiated (5000 rad) T51 LCL. EBV-transformed lymphoblastoid cell lines (LCL), PM (Bristol-Myers Squibb Co.) and T51 (Bristol-Myers Squibb Co.) were maintained in RPMI supplemented with 10% FBS. After 6 days, alloreactive "blasts" cells were cryopreserved. Secondary MLR were conducted by culturing thawed alloreactive blasts together with fresh irradiated T51 LCL in the presence and absence of mAbs and Ig fusion proteins. Cells were cultured in 96 well flat bottom plates ($4 \times 10^4$ alloreactive blasts and $1 \times 10^4$ irradiated T51 LCL cells/well, in a volume of 0.2 ml) in RPMI containing 10% FBS. Cellular proliferation of quadruplicate cultures was measured by uptake of [$^3$H]-thymidine during the last 6 hours of a 2–3 day culture.

PHA-activated T cells were prepared by culturing PBLs with 1 micro g/ml PHA (Wellcome, Charlotte, N.C.) for five days, and one day in medium lacking PHA. Viable cells were collected by sedimentation through Lymphocyte Separation Medium before use. Cells were stimulated with mAbs or transfected CHO cells for 4–6 hr at 37 degrees C., collected by centrifugation and used to prepare RNA.

CD4$^+$ T cells were isolated from PBLs by separating PBLs from healthy donors into T and non-T cells using sheep erythrocyte rosetting technique and further separating T cells by panning into CD4$^+$ cells as described by Damle et al., *J. Immunol.* 139:1501 (1987), incorporated by reference herein.

B cells were also purified from peripheral blood by panning as described by Wysocki and Sato, *Proc. Natl. Acad. Sci.* 75:2844 (1978), incorporated by reference herein, using anti-CD19 mAb 4G9. To measure T$_h$-induced Ig production, $10^6$ CD4$^+$ T cells were mixed with $10^6$ CD19$^+$ B cells in 1 ml of RPMI containing 10% FBS. Following culture for 6 days at 37 degrees C., production of human IgM was measured in the culture supernatants using solid phase ELISA as described by Volkman et al., *Proc. Natl. Acad. Sci. USA* 78:2528 (1981), incorporated by reference herein.

Briefly, 96-well flat bottom microtiter ELISA plates (Corning, Corning, N.Y.) were coated with 200 micro liter/well of sodium carbonate buffer (pH 9.6) containing 10 micro grams/ml of affinity-purified goat anti-human IgG or IgM antibody (Tago, Burlingame, Calif.), incubated overnight at 4° C., and then washed with PBS and wells were further blocked with 2% BSA in PBS (BSA-PBS).

Samples to be assayed were added at appropriate dilution to these wells and incubated with 200 micro liter/well of 1:1000 dilution of horseradish peroxidase (HRP)-conjugated F(ab')$_2$ fraction of affinity-purified goat anti-human IgG or IgM antibody (Tago). The plates were then washed, and 100 micro liters/well of o-phenylenediamine (Sigma Chemical Co., St. Louis, Mo.) solution (0.6 mg/ml in citrate-phosphate buffer with pH 5.5 and 0.045% hydrogen peroxide). Color development was stopped with 2 N sulfiric acid. Absorbance at 490 nm was measured with an automated ELISA plate reader.

Test and control samples were run in triplicate and the values of absorbance were compared to those obtained with known IgG or IgM standards run simultaneously with the supernatant samples to generate the standard curve using which the concentrations of Ig in the culture supernatant were quantitated. Data are expressed as ng/ml of Ig±SEM of either triplicate or quadruplicate cultures.

Immunoprecipitation Analysis and SDS PAGE. Cells were surface-labeled with $^{125}$I and subjected to immunoprecipitation analysis. Briefly, PHA-activated T cells were surface-labeled with $^{125}$I using lactoperoxidase and $H_2O_2$ as described by Vitetta et al., *J. Exp. Med.* 134:242 (1971), incorporated by reference herein. SDS-PAGE chromatography was performed on linear acrylamide gradients gels with stacking gels of 5% acrylamide. Gels were stained with Coomassie Blue, destained, and photographed or dried and exposed to X ray film (Kodak XAR-5).

Binding Assays. B7Ig was labeled with $^{125}$I to a specific activity of approximately $2 \times 10^6$ cpm/pmole. Ninety-six well plastic dishes were coated for 16–24 hrs with a solution containing CTLA4Ig (0.5 micro g in a volume of 0.05 ml of 10 mM Tris, pH 8). Wells were blocked with binding buffer (DMEM containing 50 mM BES (Sigma Chemical Co.), pH 6.8, 0.1% BAS, and 10% FCS) before addition of a solution (0.09 ml) containing $^{125}$I B7Ig (approximately $5 \times 10^5$ cpm) in the presence or absence of competitor. Following incubation for 2–3 hrs at 23 degrees C., wells were washed once with binding buffer, and four times with PBS. Bound radioactivity was then solubilized by addition of 0.5N NaOH, and quantified by gamma counting.

Binding to B7Ig. The functional activity of the OMCTLA4 construct encoding the complete human CTLA4 DNA gene, is shown in the experiment shown in FIG. 4. COS cells were transfected with expression plasmids CD7, OMCD28 and OMCTLA4 as described above. Forty-eight hours following transfection, cells were collected and incubated with medium only (no addition) or with mAbs 9.3, B7Ig, CD5Ig or G3–7. Cells were then washed and binding was detected by a mixture of FITC-conjugated goat anti-mouse Ig and FITC-conjugated goat anti-human Ig second step reagents. Transfected cells were tested for expression of the appropriate cell surface markers by indirect immunostaining and fluorescence was measured using FACS$^R$ analysis as described above.

Figure 4:
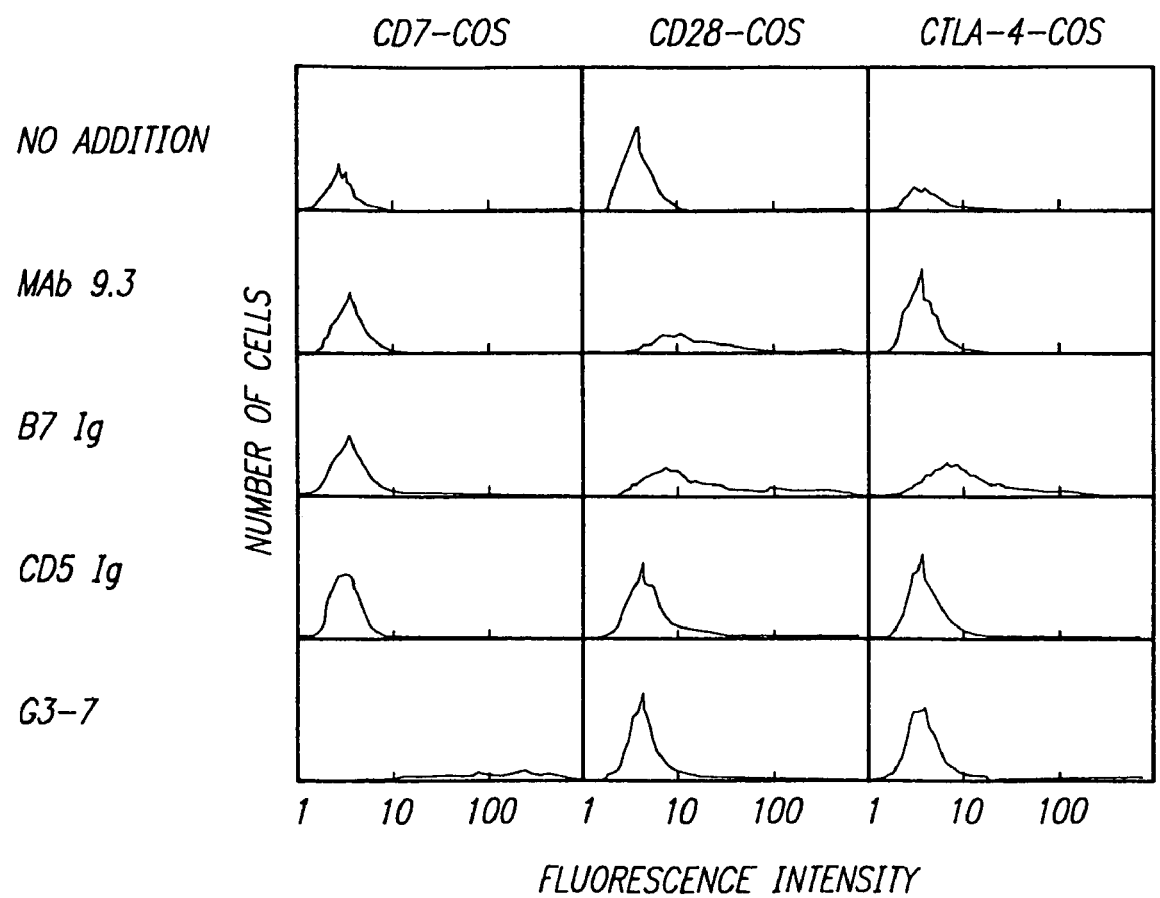
FIG. 4: Depicts the results of $FACS^R$ analysis of binding of the B7Ig fusion protein to CD28- and CTLA4-transfected COS cells as described in Example 4, infra.

As shown in FIG. 4, mAb 9.3 bound to CD28-transfected COS cells, but not to CTLA4-transfected cells. In contrast, the B7Ig fusion protein (but not control CD5Ig fusion protein) bound to both CD28- and CTLA4-transfected cells. CD7-transfected COS cells bound neither mAb 9.3 nor either of the fusion proteins. This indicates that CD28 and CTLA4 both bind the B cell activation antigen, B7. Furthermore, mAb 9.3 did not detectably bind CTLA4.

Binding of CTLA4Ig on B7 Positive CHO cells. To further characterize the binding of CTLA4Ig and B7, the binding activity of purified CTLA4Ig on B7$^+$ CHO cells and on a lymphoblastoid cell line (PM LCL) was measured in the experiment shown in FIG. 5. Amplified transfected CHO cell lines and PM LCLs were incubated with medium only (no addition) or an equivalent concentration of human IgCγ1-containing proteins (10 micro grams/ml) of CD5Ig, CD28Ig or CTLA4Ig. Binding was detected by FACS$^R$ following addition of FITC-conjugated goat anti-human Ig second step reagents. A total of 10,000 stained cells were analyzed by FACS$^R$.

Figure 5:
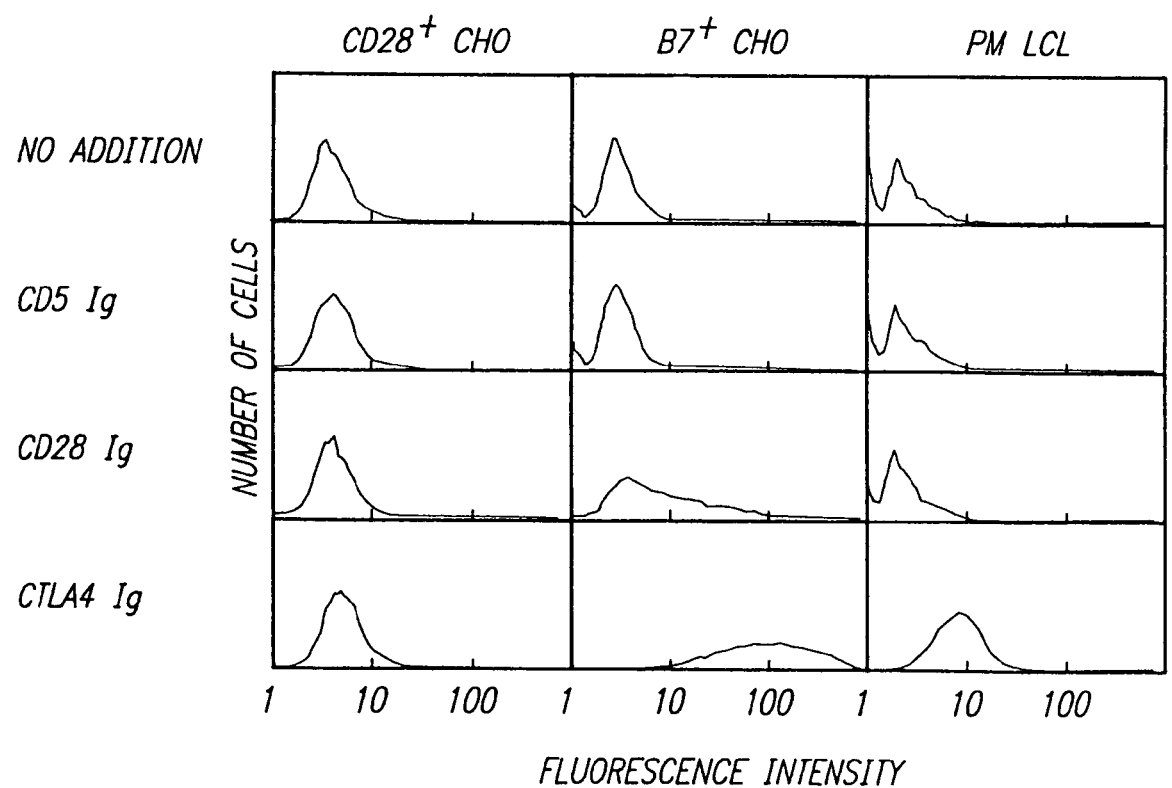
FIG. 5: Depicts the results of $FACS^R$ analysis of binding of purified CTLA4Ig on B7 antigen-positive ($B7^+$) CHO cells and on a lymphoblastoid cell line (PM LCL) as described in Example 4, infra.

As shown in FIG. 5, CD28Ig bound to B7$^+$ CHO cells but not to PM LCL, a cell line which expresses relatively low levels of the B7 antigen (Linsley et al., supra, 1990). CTLA4Ig bound more strongly to both cell lines than did CD28Ig, suggesting that it bound with higher affinity. Neither CD28Ig nor CTLA4Ig bound to CD28$^+$ CHO cells.

Affinity of Binding of CTLA4Ig and B7Ig. The apparent affinity of interaction between CTLA4Ig and B7Ig was then measured using a solid phase competition binding assay. Ninety-six well plastic dishes were coated with CTLA4Ig as described above. B7Ig was radiolabeled with $^{125}$I (5×10$^5$ cpm, 2×10$^6$ cpm/pmole), and added to a concentration of 4 nM in the presence of the indicated concentrations (FIG. 6) of unlabeled chimeric mAb L6, mAb 9.3, mAb BB-1 or B7Ig. Plate-bound radioactivity was determined and expressed as a percentage of radioactivity bound to wells treated without competitor (28,300 cpm). Each point represents the mean of duplicate determinations; replicates generally varied from the mean by $\leq$20%.

Concentrations were calculated based on a $M_r$ of 75,000 per binding site for mAbs and 51,000 per binding site for B7Ig.

Figure 6:
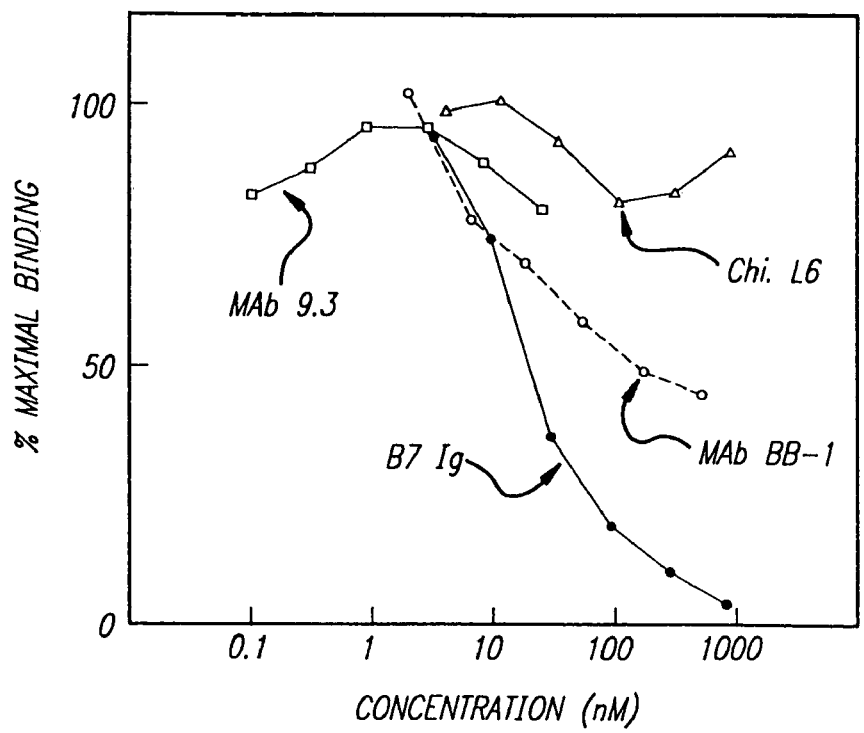
FIG. 6: Shows a graph illustrating competition binding analysis of $^{125}$I labeled B7Ig to immobilized CTLA4Ig as described in Example 4, infra.

As shown in FIG. 6, only mAb BB-1 and unlabeled B7Ig competed significantly for $^{125}$I-B7Ig binding (half maximal effects at approximately 22 nM and approximately 175 nM, respectively). Neither chimeric mAb L6, nor mAb 9.3 competed effectively at the concentrations tested. In other experiments, the concentrations of mAb 9.3 used were sufficient to inhibit binding of $^{125}$I-B7Ig to immobilized CD28Ig or to cell surface expressed CD28 by $\geq$90%.

Figure 7:
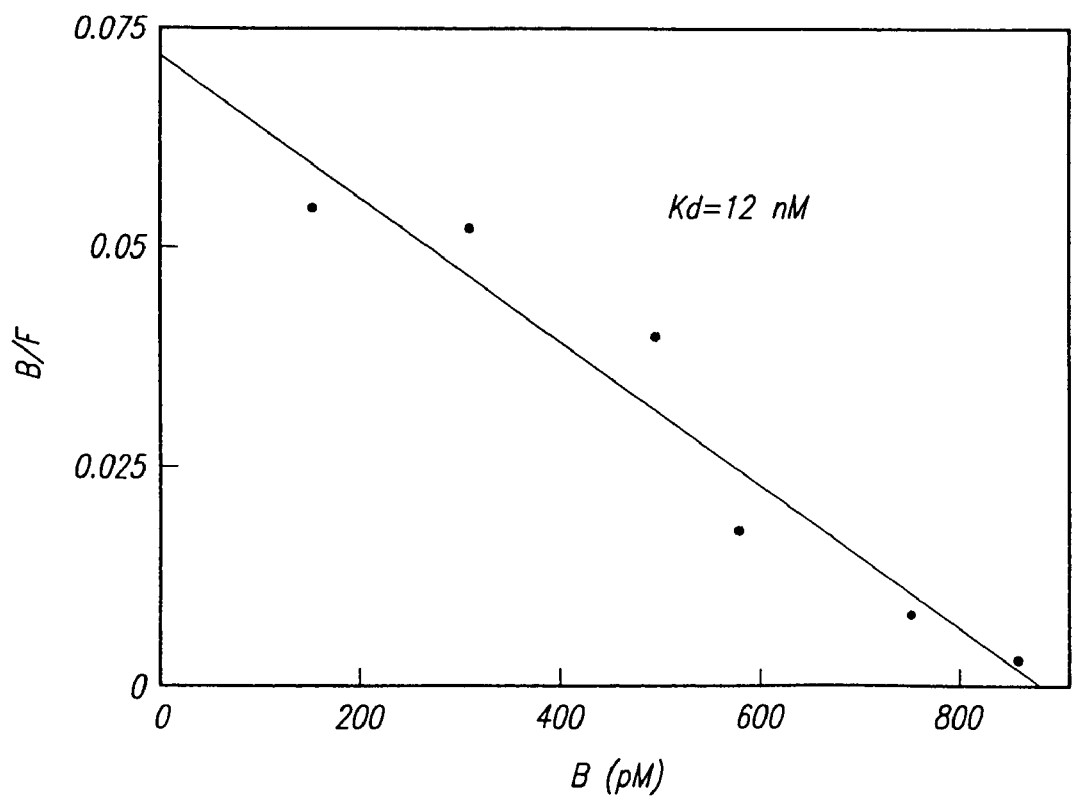
FIG. 7: Depicts a graph showing the results of Scatchard analysis of $^{125}$I-labeled B7Ig binding to immobilized CTLA4Ig as described in Example 4, infra.

When the competition data from FIG. 6 were plotted in a Scatchard representation, a dissociation constant, $K_d$, of approximately 12 nM was calculated for binding of $^{125}$I-B7 to immobilized CTLA4Ig (FIG. 7). This value is approximately 20 fold lower than the previously determined $K_d$ of binding between $^{125}$I-B7Ig and CD28 (approximately 200 nM) (Linsley et al, (1991), supra) indicating that CTLA4 is a higher affinity receptor for the B7 antigen than CD28 receptor.

Figure 8:
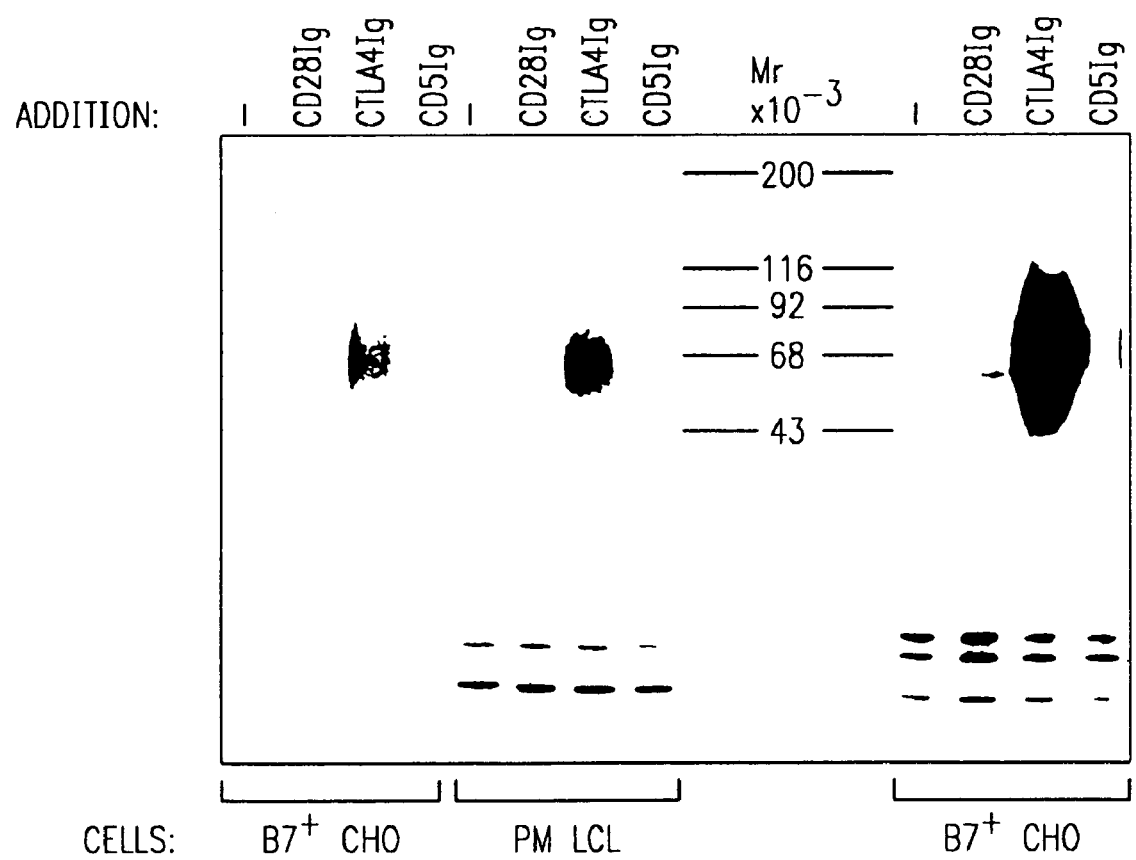
FIG. 8: Shows a photograph of a gel from SDS-PAGE chromatography of immunoprecipitation analysis of B7 positive CHO cells and PM LCL cells surface-labeled with $^{125}$I as described in Example 4, infra.

To identify the molecule(s) on lymphoblastoid cells which bound CTLA4Ig, $^{125}$I-surface labeled cells were subjected to immunoprecipitation analysis (FIG. 8). B7$^+$ CHO and PM LCL cells were surface-labeled with $^{125}$I, and extracted with a non-ionic detergent solution as described above. Aliquots of extracts containing approximately 1.5×10$^7$ cpm in a volume of 0.1 ml were subjected to immunoprecipitation analysis as described above with no addition, or 2 micro grams each of CD28Ig, CTLA4Ig or CD5Ig. Washed immunoprecipitates were then analyzed by SDS-PAGE (10–20% acrylamide gradient) under reducing conditions. The gel was then dried and subjected to autoradiography. The left panel of FIG. 8 shows an autoradiogram obtained after a 1 day exposure. The right panel of FIG. 8 shows an autoradiogram of the same gel after a 10 day exposure. The autoradiogram in the center panel of FIG. 8 was also exposed for 10 days. Positions of molecular weight standard are also indicated in this figure.

As shown by FIG. 8, a diffusely migrating ($M_r$ approximately 50,000–75,000; center at approximately 60,000) radiolabeled protein was immunoprecipitated by CTLA4Ig, but not by CD28Ig or CD5Ig. This molecule co-migrated with B7 immunoprecipitated from B7$^+$ CHO cells by CTLA4Ig, and much more weakly, by CD28Ig. These findings indicate that CTLA4Ig binds a single protein on lymphoblastoid cells which is similar in size to the B7 antigen.

Inhibition of Immune Responses In Vitro by CTLA4Ig

Inhibition of Proliferation. Previous studies have shown that the anti-CD28 mAb, mAb 9.3, and the anti-B7 mAb, mAb BB-1, inhibit proliferation of alloantigen specific $T_h$ cells, as well as immunoglobulin secretion by alloantigen-presenting B Cells (Damle, et al., *Proc. Natl. Acad. Sci.* 78:5096 (1981); Lesslauer et al., *Eur. J. Immunol.* 16:1289 (1986)). Because CTLA4 is a high affinity receptor for the B7 antigen as demonstrated herein, soluble CTLA4Ig was tested for its ability to inhibit these responses. The effects of CTLA4Ig on T cell proliferation were examined in the experiment shown in FIG. 9.

Figure 9:
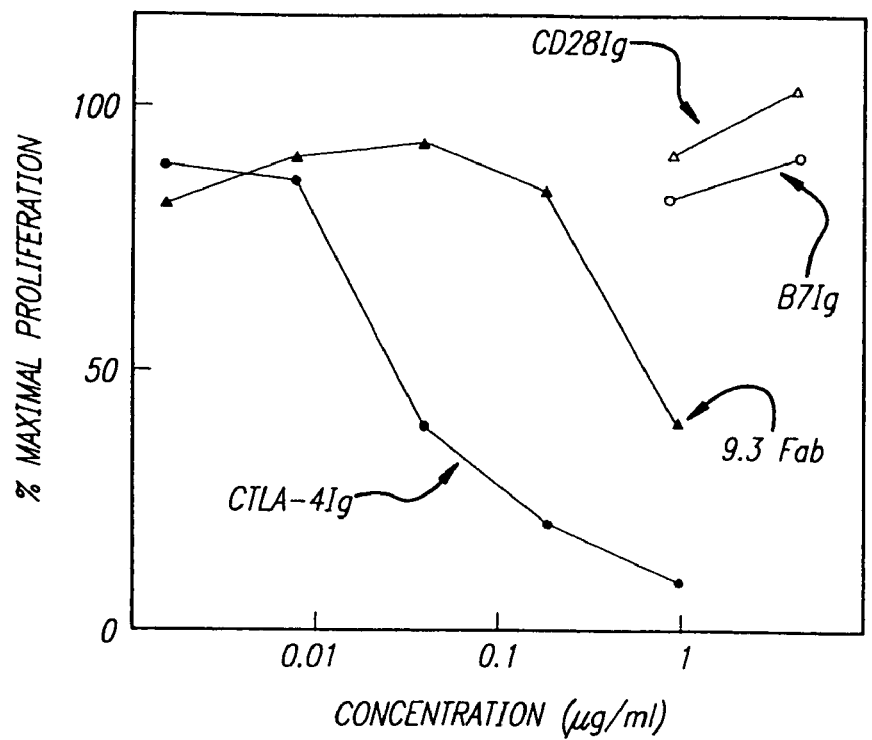
FIG. 9: Depicts a graph showing the effects on proliferation of T cells of CTLA4Ig as measured by [$^3$H]-thymidine incorporation as described in Example 4, infra.

Primary mixed lymphocyte reaction (MLR) blasts were stimulated with irradiated T51 lymphoblastoid cells (LC) in the absence or presence of concentrations of murine mAb 9.3 Fab fragments, or B7Ig, CD28Ig or CTLA4Ig immunoglobulin Cγ fusion proteins. Cellular proliferation was measured by [$^3$H]-thymidine incorporation after 4 days and is expressed as the percentage of incorporation by untreated cultures (21,000 cpm). FIG. 9 shows the mean of quadruplicate determinations (SEM$\leq$10%).

As shown in FIG. 9, CTLA4Ig inhibited the MLR reaction in a dose-dependant fashion by a maximum of >90% with a ½ maximal response at approximately 30 ng/ml (approximately 0.8 nM). The Fab fragment of mAb 9.3, which previously was shown to be a more potent inhibitor of MLR than whole mAb 9.3 (Damle et al., *J. Immunol.* 140:1753–1761 (1988)), also inhibited the MLR, but at higher concentrations (approximately 800 ng/ml or approximately 30 nM for ½ maximal response). B7Ig and CD28Ig did not significantly inhibit the MLR even at higher concentrations. In another experiment, addition of B7Ig together with CTLA4Ig partially overcame the inhibition of MLR by CTLA4Ig, indicating that the inhibition was specifically due to interactions with B7 antigen.

Figure 10:
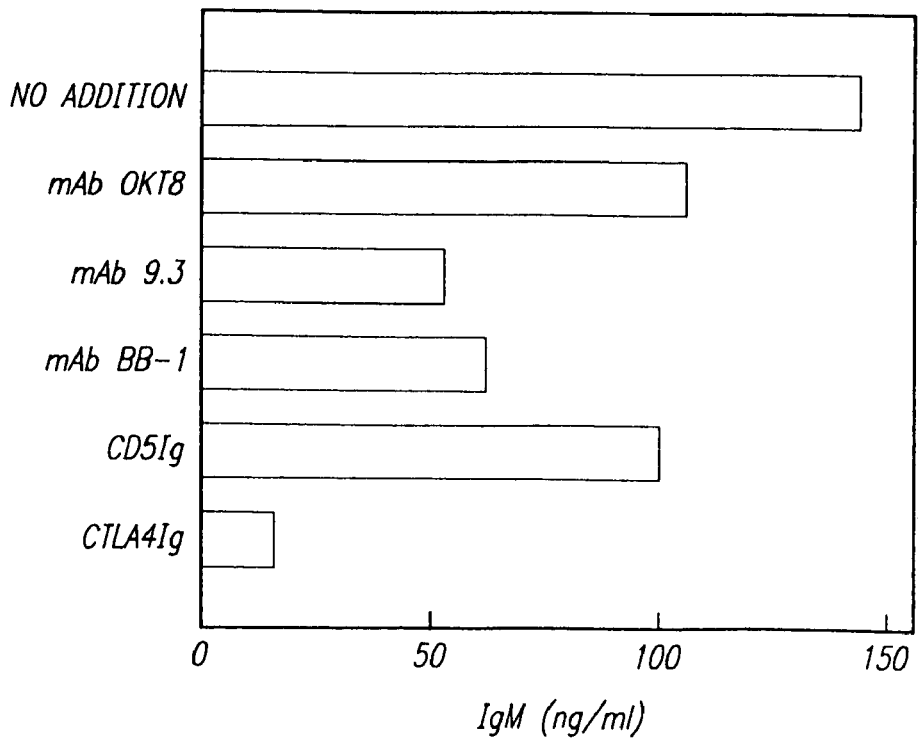
FIG. 10: Shows a bar graph illustrating the effects of CTLA4Ig on helper T cell ($T_h$)-induced immunoglobulin secretion by human B cells as determined by enzyme immunoassay (ELISA) as described in Example 4, infra.

Inhibition of Immunoglobulin Secretion. The effects of CTLA4Ig on helper T cell ($T_h$)-induced immunoglobulin secretion were also examined (FIG. 10). CD4$^+$ T cells were mixed with allogeneic CD 19$^+$ B cells in the presence or absence of the indicated immunoglobulin molecules as described above. Murine mAbs OKT8, 9.3 and BB-1 were added at 20 micro grams/ml, and Ig fusion proteins at 10 micro grams/ml. After 6 days of culture, concentrations of human IgM (SEM<5%) in culture supernatants were determined by enzyme immunoassay (ELISA) as described above. IgM production by B cells cultured in the absence of CD4$^+$ T cells was 11 ng/ml.

As shown in FIG. 10, CD4$^+$ T cells stimulated IgM production by allogenic CD 19$^+$ B Cells (in the absence of CD4$^+$ T cells, IgM levels were reduced by 93%). mAbs 9.3 and BB-1 significantly inhibited $T_h$-induced IgM production (63% and 65% inhibition, respectively). CTLA4Ig was even more effective as an inhibitor (89% inhibition) than were these mAbs. Inhibition by control Ig molecules, mAb OKT8 and CD5Ig, was much less ($\leq$30% inhibition). None of these molecules significantly inhibited Ig production measured in the presence of *Staphylococcal aureus* enterotoxin B. Similar results were obtained with CD4$^+$ T cells and B cells derived from other donors. These results indicate that the inhibition by CTLA4Ig is specific.

The above data also demonstrate that the CTLA4 and CD28 receptors are functionally as well as structurally related. Like CD28, CTLA4 is also a receptor for the B cell activation antigen, B7. CTLA4Ig bound $^{125}$I-B7 with an affinity constant, $K_d$, of approximately 12 nM, a value some 20 fold higher than the affinity between CD28 and B7Ig (approximately 200 nM). Thus, CTLA4 and CD28 may be thought of as high and low affinity receptors, respectively, for the same ligand, the B7 antigen.

The apparent affinity between CD28 and B7 is similar to the affinity reported for binding of soluble alloantigen to the T cell receptor of a murine T cell hybridoma (approximately 100 nM; Schnek et al., *Cell* 56:47 (1989)), and is higher affinity than interactions between CD2 and LFA3 (Recny et al., *J. Biol. Chem.* 265:8542 (1990)), or CD4 and MHC class II molecules (Clayton et al., *Nature* 339:548 (1989)). The affinity constant, $K_d$, between CTLA4 and B7 is even greater, and compares favorably with higher affinity mAbs ($K_d$ 2–10,000 nM; Alzari et al., *Ann. Rev. Immuno.* 6:555 (1988)). The $K_d$ between CTLA4 and B7 is similar to or greater than $K_d$ values of integrin receptors and their ligands (10–2000 nM; Hautanen et al., *J. Biol. Chem.* 264:1437–1442 (1989); Di Minno et al., *Blood* 61:140–148 (1983); Thiagarajan and Kelley, *J. Biol. Chem.* 263:035–3038 (1988)). The affinity of interaction between CTLA4 and B7 is thus among the highest yet reported for lymphoid adhesion systems.

These results demonstrate the first expression of a functional protein product of CTLA4 transcripts. CTLA4Ig, a fusion construct containing the extracellular domain of CTLA4 fused to an IgCγ1 domain, forms a disulfide-linked dimer of $M_r$ approximately 50,000 subunits. Because no interchain disulfides would be predicted to form in the Ig portion of this fusion, it seems likely that cysteines from CTLA4 are involved in disulfide bond formation. The analogous CD28Ig fusion protein (Linsley et al, supra, 1991) also contains interchain disulfide linkage(s). These results suggest that CTLA4 receptor, like CD28 (Hansen et al., *Immunogenetics* 10:247–260 (1980)), exists on the T cell surface as a disulfide linked homodimer. Although CD28 and CTLA4 are highly homologous proteins, they are immunologically distinct, because the anti-CD28 mAb, mAb 9.3, does not recognize CTLA4 (FIGS. 4 and 5).

It is not known whether CTLA4 can activate T cells by a signalling pathway analogous to CD28. The cytoplasmic domains of murine and human CTLA4 are identical (Dariavach et al., supra 1988), suggesting that this region has important functional properties. The cytoplasmic domains of CD28 and CTLA4 also share homology, although it is unclear if this is sufficient to impart similar signaling properties to the two molecules.

CTLA4Ig is a potent inhibitor of in vitro lymphocyte functions requiring T cell and B cell collaboration (FIGS. 9 and 10). These findings, together with previous studies, indicate the fundamental importance of interactions between B7 antigen and its counter-receptors, CD28 and/or CTLA4, in regulating both T and B lymphocyte responses. CTLA4Ig should be a useful reagent for future investigations on the role of these interactions during immune responses. CTLA4Ig is a more potent inhibitor of in vitro lymphocyte responses than either mAb BB-1 or mAb 9.3 (FIGS. 9 and 10). The greater potency of CTLA4Ig over mAb BB-1 is most likely due to the difference in affinities for B7 between these molecules (FIG. 6). CTLA4Ig is also more potent than mAb 9.3, probably because, unlike the mAb, it does not also have direct stimulatory effects on T cell proliferation (June et al., *Immunology Today* 11:211 (1989)) to counteract its inhibitory effects. The immunosuppressive effects of CTLA4Ig in vitro suggest that future investigations are warranted into possible therapeutic effects of this molecule for treatment of autoimmune disorders involving aberrant T cell activation or Ig production.

As will be apparent to those skilled in the art to which the invention pertains, the present invention may be embodied in forms other than those specifically disclosed above without departing from the spirit or essential characteristics of the invention. The particular embodiments of the invention described above, are, therefore, to be considered as illustrative and not restrictive. The scope of the present invention is as set forth in the appended claims rather than being limited to the examples contained in the foregoing description.

EXAMPLE 5

The following provides a description of the methods used to inhibit graft versus host disease in mice receiving human islet grafts.

Female BALB/c ($H-2^d$) and C57BL/6 ($H-2^d$) mice, 6 to 8 wk. of age were obtained from The Jackson Laboratory (Bar Harbor, Me.).

Human pancreatic islets cells were purified after collagenase digestion as described (C. Ricordi et al. Transplantation 52:519 (1991); A. G. Tzakis et al. Lancet 336:402 (1990); C. Ricordi, P. E. Lacy, E. H. Finke, B. J. Olack, D. W. Scharp, Diabetes 37:413 (1988)).

B6 or B10 mice, treated with streptozocin (175 mg per kilogram of body weight) 3 to 5 days before transplant and exhibiting nonfasting plasma glucose levels of greater than 280 mg/dl (with the majority over 300 mg/ml), were used as recipients.

Each animal received approximately 800 fresh human islets of 150 micro meters in diameter beneath the left renal capsule (D. Faustman and C. Coe, Science 252:1700 (1991); Y. J. Zeng et al. Transplantation 53:277 (1992)). Treatment was started immediately after transplantation.

Figure 11A:
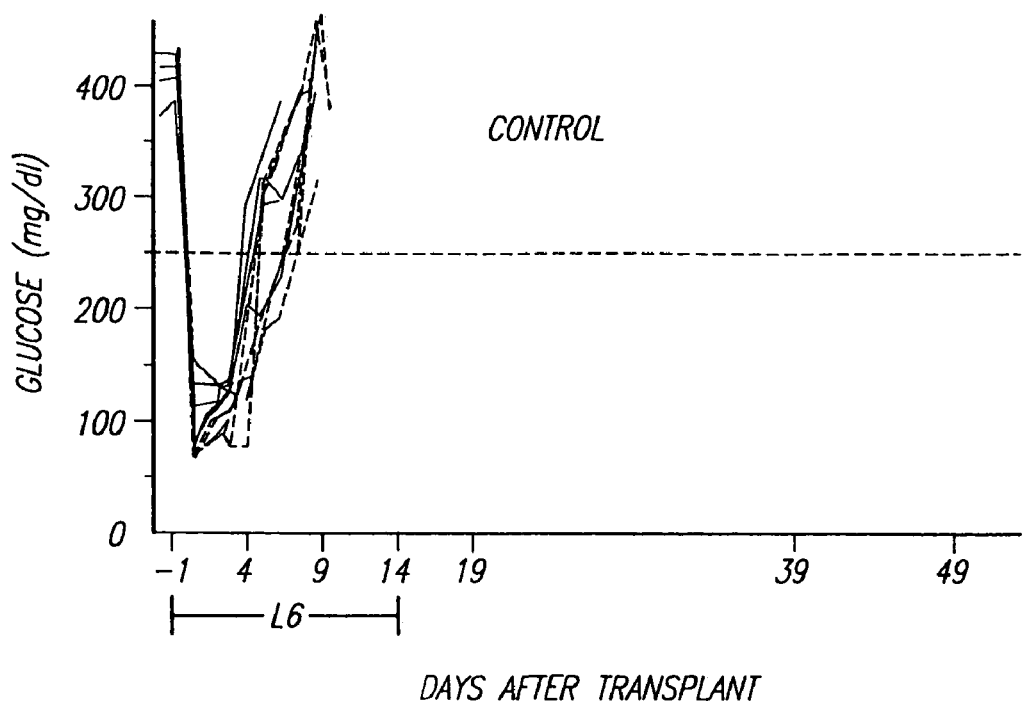
FIGS. 11a–c: Depicts graphs showing the survival of human pancreatic islet xenografts in mice, as described in Example 5, infra.

Control animals were treated with PBS (solid lines) or L6 (dotted lines) at 50 micro grams every other day for 14 days immediately after transplantation (FIG. 11A). L6 is a human IgG1 chimeric Mab. Islet transplants were considered rejected when glucose levels were greater than 250 mg/dl for three consecutive days. Animals treated with PBS (n=14) and L6 (n=8) had mean graft survivals of 5.6 and 6.4 days, respectively.

Figure 11B:
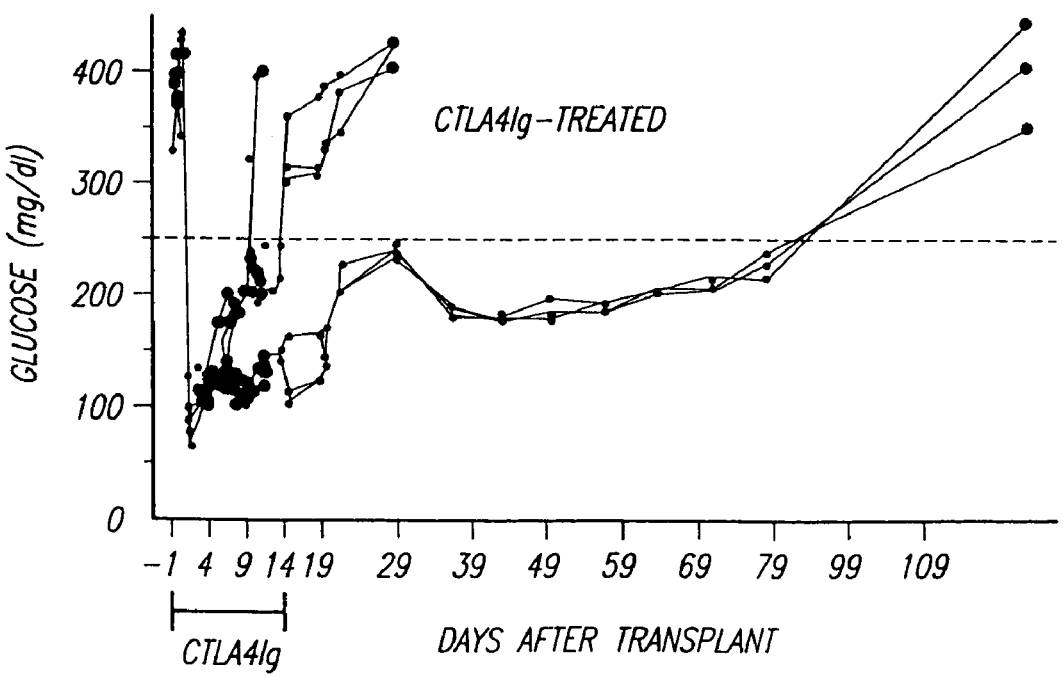

Animals were treated with 10 micro grams of CTLA4Ig for 14 consecutive days immediately after transplant (n=7) (FIG. 11B). Three out of seven animals maintained their grafts for >80 days. The remaining four animals had a mean graft survival of 12.75 days.

Figure 11C:
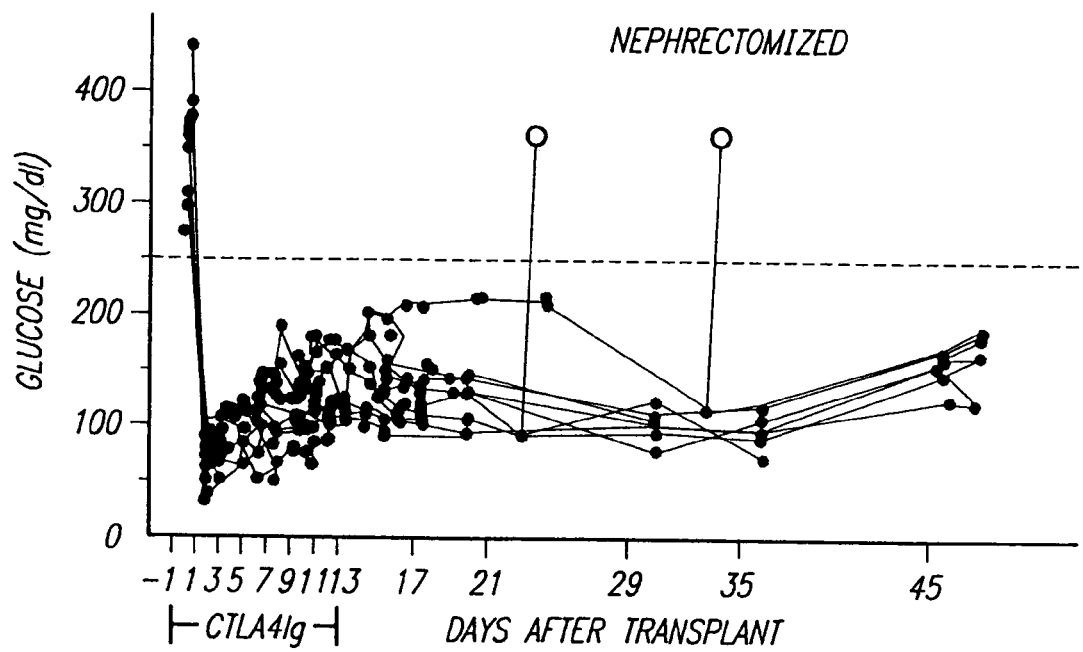

Animals were treated with 50 micro grams of CTLA4Ig every other day for 14 days immediately after human islet transplantation (FIG. 11C). All animals (n=12) treated with this dose maintained grafts throughout the analysis (FIG. 11C). Selected mice were nephrectomized on days 21 and 29 after the transplant to assess the graft's function (FIG. 11C).

Histology was performed on kidneys transplanted with human islet cells (FIGS. 12 A, B, C, D). The slides were analyzed blindly.

Hematoxylin and eosin staining of a control human islet grafted mouse 29 days after transplantation showed a massive lymphocyte infiltration (FIG. 12A). The same tissue, stained for insulin, showed no detectable insulin production (FIG. 12B).

Histological examination of tissue from a CTLA4Ig-treated mouse 21 days after transplant showed intact islets under the kidney capsule with very few lymphocytes infiltrating the transplanted tissue (FIG. 12C). The tissue was stained with hematoxylin and eosin. The same tissue from the CTLA4Ig-treated mouse, stained for insulin, showed the production of insulin by the grafted islets (FIG. 12D). Similar results were observed in graft tissue examined at later time points. The upper, middle, and lower arrowheads identify the kidney capsule, islet transplant, and kidney parenchyma, respectively.

In the histopathology assay all tissues were fixed in 10% buffered formalin and processed, and 5-micro meter sections were stained either with hematoxylin and eosin or for insulin with the avidin-biotin-peroxidase method (S. M. Hsu, L. Raine, H. Fanger, J. Histochem, Cytochem, 29:577 (1981)). Magnification was x 122.

In FIG. 13 streptozotocin-treated animals were transplanted as described hereinabove for FIG. 11. The mice were treated either with PBS (dotted lines) or with MAb to human B7 (solid lines) at a dose of 50 micro grams every other day for 14 days (FIG. 13). Control animals (treated with PBS) (n=3) had a mean graft survival of 3.5 days, whereas anti-B7-treated animals (n=5) maintained grafts from 9 to >50 days (FIG. 13).

In FIG. 14 normal glycemic, CTLA4Ig-treated, transplanted mice (dotted lines) were nephrectomized on day 44 after transplant and immediately retransplanted with either 1000 first party donor islets (dotted lines, solid circles) or 1000 second party islets (dotted lines, open circles) beneath the remaining kidney capsule.

These islets, frozen at the time of the first transplant, were thawed and cultured for 3 days before transplant to ensure islet function. B10 mice that had been treated with streptozotocin and exhibited nonfasting glucose levels of greater than 280 mg/dl were used as controls (solid lines) (FIG. 14). No treatment was given after transplantation.

Control animals rejected both the first party (solid lines, closed circles) and the second party (solid lines, open circles) islet grafts by day 4 after transplant (FIG. 14). The CTLA4Ig-treated mice retransplanted with second party islets had a mean graft survival of 4.5 days, whereas animals retransplanted with first party donor islets maintained grafts for as long as analyzed (>80 days) (FIG. 14).

CTLA4Ig significantly prolongs human islet graft survival in mice in a donor-specific manner thereby providing an approach to immunosuppression C57BL/6 (B6) or C57BL/10 (B10) mice were treated with streptozotocin to eliminate mouse pancreatic islet B cell function. Diabetic animals were grafted under the kidney capsule, and treatment was started immediately after surgery. Survival of the islet grafts was monitored by the analysis of blood glucose concentrations.

Transplanted control animals, treated with either phosphate-buffered saline (PBS)(n=14) or L6 (a human IgG1 chimeric MAb; n=8), had a mean graft survival of 5.6 and 6.4 days, respectively (FIG. 11A).

In contrast, islet rejection was delayed in animals treated with CTLA4Ig (10 micro grams per day for 14 days), with four out of the seven animals exhibiting moderately prolonged mean graft survival (12.75 days), whereas the remaining three animals maintained normal glucose levels for >80 days (FIG. 11B). This eventual increase in glucose concentration may be a result of islet exhaustion because no evidence of active cellular rejection was observed.

In the three mice that maintained long-term islet grafts, the transient increase in glucose concentrations around day 21 after the transplant may have represented a self-limited rejection episode consistent with the pharmacokinetics of CTLA4Ig clearance after therapy (P. S. Linsley et al., Science 257:792 (1992)).

In subsequent experiments, the dose of CTLA4Ig was increased to 50 micro grams per animal every other day for about 14 days. This treatment resulted in 100% of the animals maintaining normal islet function throughout the experiment with no signs of a rejection crisis (FIG. 11C).

In order to confirm that insulin production originated from the transplanted islets and not from the native mouse pancreas, we nephrectomized selected animals at days 21 and 29 to remove the islet grafts (FIG. 11C). In these animals, glucose concentrations increased to above 350 mg/dl within 24 hours, which indicated that the islet xenograft was responsible for maintaining normal glucose levels. It appears that the blocking of the CD28-B7 interaction inhibits xenogenic islet graft rejection.

The effects of treatment with the soluble receptor, namely CTLAIg fusion protein, were not a result of Fc binding (L6 did not effect graft rejection) or general effects on T cell or B cell function in vivo.

Histological analyses of islet xenograft from control (PBS treated) and CTLA4Ig treated mice were done (FIGS. 12A, 12B, 12C, 12D). The islet tissue from the control animal demonstrated evidence of immune rejection, with a marked lymphocytic infiltrate into the graft and few remaining islets (FIG. 12A).

Immunohistochemical staining showed that insulin-positive cells were present only rarely, and no somatostatin-positive cells were present at all (FIG. 12B). In contrast, transplant tissue from the CTLA4Ig-treated mice was devoid of any lymphocytic infiltrate (FIG. 12C).

The grafts were intact, with many islets visible. In addition, the B cells observed in the human islet tissue produced human insulin (FIG. 12D) and somatostatin.

The human CTLA4Ig used in this study reacts with both murine and human B7. One advantage of the xenogeneic transplant model is the availability of a MAb to human B7 that does not react with mouse B7 (T. Yokochi, R. D. Holly, E. A. Clark, J. Immunol. 128:823 (1982)). Thus, the role of human B7-bearing antigen-presenting cells (APCs) could be directly examined.

The mice were transplanted as described and then treated with 50 micro grams of MAb to human B7 every other day for 14 days after transplant. This treatment prolonged graft survival in treated mice (9 to >50 days) in comparison to that for control mice (FIG. 13). The anti-B7 MAb is unable to block rejection as effectively as CTLA4Ig.

The CTLA4Ig therapy resulted in graft acceptance in the majority of mice. However, the animals may not be tolerant. Transient immunosuppression can lead to permanent islet graft acceptance because of graft adaptation (the loss of immunogenicity as a result of the loss of APC function) (L. Hao, Y. Wang, R. G. Gill, K. J. Lafferty, J. Immunol. 139:4022 (1987); K. J. Lafferty, S. J. Prowse, M. Simeonovic, Annu. Rev. Immunol. 1:143 (1983)).

In order to differentiate between these possibilities, we nephrectomized selected xenografted, CTLA4Ig-treated mice (day 40) and retransplanted them under the remaining kidney capsule with either the original donor islets (first party) or unrelated second party human islets (FIG. 14).

Streptozotocin-treated control animals, having never received an islet graft, were also transplanted with either first or second party islets. No treatment after the transplant was given. Control animals rejected the first and second party islets by day 4. The CTLA4Ig-treated animals that had received the second party islets rejected these islets by day 5, whereas animals receiving first party donor islets maintained the grafts for >80 days (FIG. 14).

These results suggest that the CTLA4Ig treatment resulted in prolonged donor-specific unresponsiveness to the xenogeneic islets. The ability of the murine immune response to distinguish differences among the human islet donors also supports the direct recognition of the polymorphic MHC products expressed on the human islet cells.

EXAMPLE 6

The following provides a description of the methods used to induce a highly specific immune response in an animal subject.

Female BALB/c (H-$2^d$) and C57BL/6 (H-$2^d$) mice, 6 to 8 wk. of age were obtained from The Jackson Laboratory (Bar Harbor, Me.).

Monoclonal antibody 11B11 is a rat IgG1 anti-murine IL-4 (Ohara, J., and W. E. Paul, 1985, Production of a monoclonal antibody to and molecular characterization of B-cell stimulatory factor-1. Nature 315:333) (Verax (Lebanon, N.H.)).

BALB/c mice (five per group) were immunized intravenously with $10^8$ SRBC alone or together with 200 micro grams chimeric L6 mAb or human CTLA4Ig fusion protein. The indicated groups were treated 2 hrs. prior to injection of SRBCs by intraperitoneal injection of 2 mls of either rat immunoglobulin or rat anti-murine IL-4 mAb 11B11 at 5 mg/ml. Treatment with chimeric L6 mAb or CTLA4Ig was repeated daily for 4 additional days.

All animals were given intravenous injections of SRBCs (FIG. 15) or KLH (FIG. 16) on day 46. Specifically, in FIG. 15, the closed circle represents mice that were administered with only SRBC at day 0 and day 46. The open circle represents mice administered with only SRBC at day 46. The remaining mice represented in FIG. 15 were further administered with SRBC at day 46. In contrast, in FIG. 16, the mice were administered with a different immunogen, KLH, at day 46 only.

Serum concentrations of mice measured as having antibodies directed against SRBCs or KLH were determined by ELISA as described (Linsley et al., Science 1992).

Serum antibody titers were calculated as the dilution giving an $A_{450}$ of five times background. Serum antibody titer values from FIG. 15 were determined from pooled sera from five mice per group, while serum antibody titer values from FIG. 16 represents mean titers of five individual sera. Arrows indicate an SRBC or KLH injection at day 46.

FIGS. 15 and 16 show that the immunological response in mice injected concurrently with both CTLA4Ig and anti-IL4 (open triangle) is suppressed in an antigen-specific manner.

FIG. 15 shows that there is no rise in serum antibody titer (i.e. no primary or secondary immunological response) in mice injected concurrently with CTLA4Ig and anti-IL4 and injected with SRBC at day 0 and day 46. The combination of CTLA4Ig and anti-IL4 suppresses a primary and secondary immune response and induces long lasting immunological non-responsiveness to SRBC.

Additionally, FIG. 15 shows that there is no primary immunological response in mice injected concurrently with CTLA4Ig and the control rat Ig (Cappel, Organontecknika, Palo Alto, Calif.). However, these mice exhibit a secondary immunological response after injection with SRBC at day 46 (closed triangle, FIG. 15).

FIG. 16 shows that administration of CTLA4Ig and anti-IL4, followed by a different immunogen, KLH, at day 46 in mice does not suppress a primary immune response to KLH in mice. Instead, these mice exhibited a primary immune response to KLH (open triangle, FIG. 16). Thus, mice treated with CTLA4Ig and anti-IL4 exhibited a highly specific immune response depending on the antigen administered therein.

EXAMPLE 7

The following provides a description of the methods used to determine the regions within CTLA4 which are required for binding B7-1 (e.g., CD80), using CTLA4/CD28 chimeric molecules.

The regions in CTLA4Ig which are required for its high avidity binding to B7-1 have been identified by site-specific and homolog mutagenesis. The following is a description of how to make soluble CTLA4/CD28 hybrid fusion proteins which bind B7.

Materials and Methods

Monoclonal antibodies (mAbs). Murine mAb's specific for CTLA4 were prepared and characterized as previously described (Linsley et al. J. Ex. Med., (1992) 176:1595–1604). Antibody 9.3 (anti-CD28) has been described previously ((Hansen et al., *Immunogenetics* 10:247–260 (1980)).

Cell Culture. The preparation of stably transfected B7-1 positive CHO cells has been previously described (Linsley et al., in *J. Exp. Med.* 173:721–730 (1991); P. S. Linsley et al., J. Exp. Med. 174:561 (1991)).

Cells were maintained in DMEM supplemented with 10% fetal bovine serum (FBS), 0.2 mM proline, and 1 micro M methotrexate. COS cells were grown in DMEM supplemented with 10% FBS. CTLA4Ig was prepared in CHO cells as previously described (Example 1).

CTLA4Ig and CD28Ig site-directed mutant expression plasmids. Site-directed mutagenesis was performed on a vector encoding soluble chimeric form of CTLA4 (CTLA4Ig) in which the extracellular domain of CTLA4 was genetically fused to the hinge and constant regions of a human IgG heavy chain (Example 1). CTLA4Ig site-directed mutants were prepared by encoding the desired mutation in overlapping oligonucleotide primers and generating the mutants by PCR (Ho et al., 1989, supra.) using the CTLA4Ig plasmid construct as a template.

Six mutants were prepared which encoded substitutions to alanine in the highly conserved hexapeptide 97MYPPPY102 forming part of the putative CDR3-like domain (FIGS. 17 and 22) (Ho et al., 1989, supra.).

In addition, two mutants encoding the residues P103A and Y104A (MYPPAY (SEQ ID NO.: 40) and MYPPPA (SEQ ID NO.: 41), respectively) from the CD28Ig 99MYPPPY104 hexapeptide using CD28Ig as a template were also prepared by the same method.

Primers required for PCR reactions but not for introducing mutations included (1) a CDM8 forward (CDM8FP) primer encoding a complementary sequence upstream of the HindIII restriction site at the 5' end of the CDM8 stuffer region, and (2) a reverse primer (CDM8RP) encoding a complementary sequence downstream of the XbaI site at the 3' end of the CDM8 stuffer region.

These primers encoded the following sequences:

CDM8FP: 5'-AATACGACTCACTATAGG (SEQ ID NO.: 33)

CDM8RP: 5'-CACCACACTGTATTAACC (SEQ ID NO.: 34)

PCR conditions consisted of 6 min at 94 degrees C. followed by 25 cycles of 1 min at 94 degrees C., 2 min at 55 degrees C. and 3 min at 72 degrees C. Taq polymerase and reaction conditions were used as suggested by the vendor (Perkin Elmer Cetus, Emeryville, Calif.). PCR products were digested with HindIII and XbaI and ligated to HindIII/XbaI-cut CDM8 expression vector.

To confirm that the desired mutations had been inserted and to verify the absence of secondary mutations, each CTLA4Ig mutant fusion protein (an example of a soluble CTLA4 mutant fusion protein) was sequenced by the dideoxy chain termination/extension reaction with Sequenase reagents used according to the manufacturers recommendations (United States Biochemical Corp., Cleveland, Ohio).

Plasmids were transfected into COS cells (Aruffo et al., Cell 61:1303 (1990)) and the conditioned media was used as a source for the resulting Ig mutant fusion proteins.

CTLA4/CD28Ig hybrid expression plasmids. CTLA4/CD28Ig hybrid plasmids encoding the constructs HS2, HS4, HS4-A, HS4-B, and HS5 (FIG. 19) were prepared by PCR using overlapping oligonucleotide primers designed to introduce CTLA4 sequences into CD28Ig while, at the same time, deleting the equivalent region from CD28. The same CDM8 forward and reverse PCR primers described above were also used.

Each cDNA construct was genetically linked to cDNA encoding the hinge and constant regions of a human IgG1 in order to make soluble chimeras.

A HS6 hybrid was prepared in a similar manner to that described above except that the CDR1-like region in CTLA4Ig was replaced with the equivalent region from CD28Ig.

HS7, HS8, and HS9 constructs were prepared by replacing a ~350 base-pair HindIII/HpaI 5' fragment of HS4, HS4-A, and HS4-B, respectively, with the equivalent cDNA fragment similarly digested from HS5 thus introducing the CDR1-like loop of CTLA4 into those hybrids already containing the CTLA4 CDR3-like region.

HS10–HS13 constructs are domain homolog mutants which were prepared by introducing the CDR2-like loop of CTLA4Ig into previously constructed homolog mutants. This was done by overlapping PCR mutagenesis whereby primers were designed to introduce CTLA4 CDR2-like sequences into homolog templates while at the same time deleting the equivalent CD28 CDR2-like region from the molecule.

Accordingly, HS4 served as a template to make HS 10; HS7 served as a template to make HS 11; HS4-A served as a template to make HS12; and HS8 served as a template to make HS13 (FIG. 19). The CDM8 primers described above were also used in these constructions.

The HS14 hybrid construct was prepared by replacing the CDR2-like loop of CD28 with the equivalent loop from CTLA4Ig (FIG. 19).

Oligonucleotide primers designed to introduce these changes were used in overlapping PCR mutagenesis identical to that described for other mutants.

PCR reactions and subcloning into CDM8 were performed as described above. Again all mutants were sequenced by the dideoxy chain termination/extension reaction.

Plasmids encoding each of the mutants were transfected into COS cells and the resulting soluble Ig fusion proteins were quantitated in culture media and visualized by Western blot as described in following sections.

Quantitation of the resulting Ig fusion proteins in culture media. Soluble mutant fusion proteins were quantitated in an enzyme immunoassay by determining the amount of Ig present in serum-free COS cell culture media.

Microtiter plates (Immulon2; Dynatech Labs., Chantilly, Va.) were coated with 0.5 micro g/ml goat anti-human IgG (Jackson Immunoresearch Labs., West Chester, Pa.) for 16–24h at 4 degrees C. Wells were blocked for 1 h with specimen diluent (Genetic Systems, Seattle, Wash.), then washed with PBS containing 0.05% Tween 20 (PBS-Tw).

COS cell culture media containing fusion proteins was added at various dilutions and incubated for 1 h at 22 degrees C. Known concentrations of CTLA4Ig were also added to separate wells on each plate for a standard curve.

After washing, horseradish peroxidase (HRP)-conjugated goat anti-human IgG (Tago, Burlingame, Calif.) diluted 1:12,000 was added and incubated for 1 h at 22 degrees C. Wells were then washed and incubated with 3,3',5,5' tetramethylbenzidine (TMB) substrate (Genetic Systems) for 15 min before stopping the reaction by the addition of 1N $H_2SO_4$. Optical density was measured at dual wavelengths of 450 and 630 nm on a microtiter plate reader (Genetic Systems).

Concentration of mutant Ig fusion protein was determined by comparison with a standard curve of known concentrations of CTLA4Ig.

Immunoprecipitation and Western blot analysis. CTLA4/CD28Ig hybrid fusion proteins present in culture media were adsorbed to protein A-Sepharose by overnight incubation at 4 degrees C. The beads were washed with PBS containing 0.1% Nonidet-P40 (NP40) then SDS PAGE sample buffer was added and the eluted protein was loaded onto an SDS polyacrylamide gel.

Western blot transfer of protein onto nitrocellulose was done by standard procedures. Nitrocellulose membranes were then blocked with PBS containing 0.1% NP40 and 1% non-fat dry milk powder.

After washing in PBS-Tw membranes were incubated with alkaline phosphatase-conjugated goat anti-human IgG (Boehringer Mannheim, Indianapolis, Ind.) diluted 1:1,000 and incubated for 1 h at 22 degrees C. Blots were then washed and developed using standard procedures.

B7 positive CHO cell enzyme immunoassay. The ability of CTLA4Ig mutant fusion proteins, and CTLA4/CD28Ig hybrid fusion proteins to bind B7-1 stably expressed on CHO cells was determined by an enzyme immunoassay.

Round bottom tissue culture treated 96 well microtiter plates (Corning, Corning, N.Y.) were seeded with B7-1 positive CHO cells at $10^3$ cells/well. Two days later the confluent cells were fixed in 95% ethanol for 15 min.

After washing with PBS-Tw, mutant Ig fusion proteins were added at various concentrations and incubated for 1 h at 4 degrees C. After washing, HRP-conjugated goat anti-human IgG (Tago) diluted 1:10,000 was added and incubated for 1 h at 22 degrees C.

Wells were then washed and TMB substrate added as above and allowed to react for 30 min before stopping the reaction with 1N $H_2SO_4$. Absorbance of the wells was measured at 450 nm.

CD28Ig site-directed mutant fusion protein binding assay. Site-directed mutant fusion proteins of CD28Ig were assayed for their ability to bind to B7-1 by an indirect enzyme immunoassay.

Wells of ELISA plates were coated with a chimeric fusion protein containing the extracellular domain of human B7-1 fused to a mouse IgG1 Fc region, at 5 micro grams/ml for 16 h at 4 degrees C. Wells were blocked for 1 h with specimen diluent (Genetic Systems) then washed with PBS-Tw. COS cell culture media containing known concentrations of mutant fusion protein was added at various concentrations and incubated for 1 h at 22 degrees C.

Known concentrations of CD28Ig were also added to separate wells on each plate. After washing, HRP-conjugated goat anti-human IgG (Tago) diluted 1:10,000 was added and incubated for 1 h at 22 degrees C. TMB substrate was added and optical densities read as described for quantitation of Ig fusion proteins in culture media.

mAb binding to Ig fusion proteins. The ability of anti-CTLA4 mAb's and the anti-CD28 mAb 9.3 to bind CTLA4/CD28Ig hybrid fusion proteins and CTLA4Ig mutant fusion proteins was assessed by an enzyme immunoassay.

Wells of microtiter plates (Immulon 2) were coated with 0.5 micro grams/ml of goat anti-human IgG (Jackson) for 16–24 h at 4 degrees C. Plates were blocked for 1 h with specimen diluent (Genetic Systems), washed with PBS-Tw, then incubated with the Ig fusion proteins for 1 h at 22 degrees C. After washing, wells were incubated with mAb at 1 micro grams/ml for 1 h at 22 degrees C.

After further washing, HRP-conjugated goat anti-mouse Ig (Tago) diluted 1:10,000 was added and incubated for 1 h at 22 degrees C. TMB substrate was added and optical density measured as described above.

CTLA4 molecular model. An approximate three-dimensional model of the CTLA4 extracellular domain was generated based on the conservation of consensus residues of IGSF variable-like domains.

Using such IGSF consensus residues as "anchor points" for sequence alignments, CTLA4 residues were assigned to the A, B, C, C', C", D, E, F, G strands of an Ig variable fold (Williams/Barclay, 1988, supra.) and the connecting loop regions (FIG. 21).

The CTLA4 model was built (InsightII, Discover, Molecular Modeling and Mechanics Programs, respectively, Biosym Technologies, Inc., San Diego) using the variable heavy chain of HyHEL-5 (Sheriff et al., 1987 PNAS 84:8075–8079) as template structure. Side-chain replacements and loop conformations were approximated using conformational searching (Bruccoleri et al., 1988 335:564–568).

Several versions of the model with modified assignments of some residues to β-strands or loops were tested using 3D-profile analysis (Luthy et al., 1992, Nature 336:83–85) in order to improve the initial alignment of the CTLA4 extracellular region sequence with an IGSF variable fold.

Results

Construction and binding activity of CTLA4Ig and CD28Ig mutant fusion proteins. A sequence alignment of various homologues of CD28 and CTLA4 is demonstrated in FIG. 17. In FIG. 17, sequences of human (H), mouse (M), rat (R), and chicken (Ch) CD28 are aligned with human and mouse CTLA4. Residues are numbered from the mature protein N-terminus with the signal peptides and transmembrane domains underlined and the CDR-analogous regions noted. Dark shaded areas highlight complete conservation of residues while light shaded areas highlight conservative amino acid substitutions in all family members.

Regions of sequence conservation are scattered throughout the extracellular domains of these proteins with the most rigorous conservation seen in the hexapeptide MYPPPY (SEQ ID NO.: 35) motif located in the CDR3-like loop of both CTLA4 and CD28 (FIG. 17). This suggests a probable role for this region in the interaction with a B7 antigen, e.g., B7-1 and B7-2.

To test this possibility, site-directed alanine scanning mutations were introduced into this region of CTLA4Ig using PCR oligonucleotide primer-directed mutagenesis thereby resulting in CTLA4Ig mutant fusion proteins. Similarly two alanine mutations were introduced into the CD28Ig MYPPPY motif thereby resulting in CD28Ig mutant fusion proteins.

All cDNA constructs were sequenced to confirm the desired mutations before transfection into COS cells. The concentrations of mutant Ig fusion proteins in serum-free COS cell culture media were determined by an Ig quantitation assay.

The ability of each CTLA4Ig mutant fusion protein to bind to B7-1 expressed on stably transfected CHO cells was then determined by an indirect cell binding immunoassay. Binding of CD28Ig mutant fusion proteins to B7-1 was assessed by an indirect enzyme immunoassay. Each of these assays are described in Materials and Methods.

Mutagenesis of each residue of the CTLA4Ig MYPPPY motif to alanine had a profound effect on binding to B7-1 as shown in FIG. 18. FIG. 18 shows that mutations in the MYPPPY motif of CTLA4Ig and CD28Ig disrupt binding to B7-1. Site-directed mutant Ig fusion proteins were produced in transiently transfected COS cells, quantitated and tested for their ability to bind to B7-1.

In FIG. 18 fusion protein quantitations were repeated at least twice with replicate determinations. Specifically, FIG. 18 shows that CTLA4Ig mutants bind to stably transfected, ethanol-fixed B7-1+ CHO cells grown to confluency in ELISA tissue culture plates. Binding data is expressed as the average of duplicate wells and is representative of at least two experiments.

Y98A and P100A mutants bound to B7-1 but with considerably reduced ability relative to wild-type CTLA4Ig. In contrast, the mutants M97A, P99A, P101A and Y102A showed an almost complete loss of binding. Furthermore, the CD28Ig MYPPPY mutants P103A and Y104A did not display detectable binding to B7-1 immobilized on wells of ELISA plates.

B7-1 transfected CHO cells which were incubated with CTLA4Ig mutant fusion protein, labeled with anti-human FITC, and assayed using a FACSCAN showed equivalent results. These results clearly demonstrate a critical role for the MYPPPY motif in both CTLA4Ig and CD28Ig binding to B7-1.

Characterization of CTLA4/CD28Ig hybrid fusion proteins. Since the MYPPPY motif is common to both CTLA4Ig and CD28Ig, it alone cannot account for the observed differences in binding to B7-1 seen with CTLA4Ig and CD28Ig. The contribution of less well conserved residues to high avidity binding B7-1 was assessed using a series of homolog mutants.

The three CDR-like regions of CD28 were replaced in various combinations with the equivalent regions from the CTLA4 extracellular domain (FIG. 19). FIG. 19 is a map of CTLA4/CD28Ig mutant fusion proteins showing % binding activity to B7-1+ CHO cells relative to CTLA4-Ig. Conserved cysteine residues (C) are shown at positions 21, 92 and 120 respectively (CTLA4 numbering). Also shown is the position of the MYPPPY motif. Open areas represent CD28 sequence; filled areas represent CTLA4 sequence; cross-hatched areas represent beginning of IgG Fc.

Percent binding activities were determined by comparing binding curves (FIG. 20 A and B) relative to CTLA4-Ig and finding the concentration of a mutant required to give the same O.D. as that found for CTLA4-Ig. The ratio of mutant protein to CTLA4-Ig concentration at a particular O.D. was then expressed as % binding activity. At least two A450 readings were taken from the linear part of the CTLA4-Ig binding curve and the average % binding activity determined.

A total of 14 hybrid cDNA constructs were prepared, sequenced, and transfected into COS cells. Concentrations of Ig fusion proteins in serum-free culture media were determined and their electrophoretic mobility compared by SDS-PAGE including Western blotting analysis.

Under reducing conditions each chimeric protein migrated with a relative molecular mass ranging between that of CTLA4Ig (Mr-50 kDa) and CD28Ig (Mr-70 kDa) depending on the size of the exchanged region.

Under non-reducing conditions the proteins migrated primarily between 100–140 kDa indicating that these fusion proteins existed as disulfide-linked dimers despite mutagenesis of the cysteine residues in the hinge region of the Fc.

Since four of the five conserved cysteine residues in CTLA4 and CD28 are thought to be involved in intrachain disulfide bonds, dimerization of the fusion proteins was therefore most likely attributable to the fifth conserved cysteine residue at position 120 in CTLA4 (position 123 in CD28).

Binding of CTLA4/CD28Ig hybrid fusion proteins to B7-1. The hybrid fusion proteins were tested for their ability to bind to B7-1 by the same indirect cell binding immunoassay used to assay the site-specific CTLA4Ig and CD28Ig mutant fusion proteins.

Under these conditions the binding between CD28Ig and B7-1 is barely detectable (FIGS. 20A and B). However, replacing residues 97 to 125 (the CDR3-like extended region) of CD28 with the corresponding residues of CTLA4 resulted in an approximately two and a half orders of magnitude increase in binding of the CD28Ig analog to B7-1 (FIGS. 20A and B). FIGS. 20A and B show that CTLA4/CD28Ig mutant fusion proteins demonstrate involvement of CDR-analogous regions in high avidity binding to B7-1 CHO cells. Mutants were assayed as described in Example 4. Data is expressed as the average of duplicate wells and is representative of at least three experiments. From these curves % binding activity relative to CTLA4-Ig was determined as explained and shown in FIG. 19.

Binding to B7-1 by this construct, termed HS4 (FIG. 19), is approximately five fold less than wild type CTLA4Ig. The HS2 hybrid which includes additional N-terminal residues of CTLA4 (amino acids 1–21), did not improve the ability of the hybrid molecule to bind to B7-1 relative to HS4.

The HS6 construct which represents the CTLA4Ig sequence except that it contains the CDR1-like region of CD28 (residues 25–32), bound similarly. However, the additional inclusion of the CTLA4 CDR1-like region (residues 24–31) into the HS4 construct (termed HS7), showed further improved binding so that the binding affinity is approximately 44% of CTLA4Ig (FIG. 19).

In contrast, inclusion of the CDR2-like region of CTLA4 (residues 50–57) into HS4 (construct HS10), did not further increase binding (FIG. 19). A similar result was found for construct HS11 which had all three CDR-like region sequences of CTLA4 included into CD28Ig. The HS5 hybrid which contained only the CDR1-like domain of CTLA4 bound at very low levels.

The CTLA4/CD28Ig hybrid HS4-A encoded CTLA4Ig residues 95–112 in the C-terminally extended CDR3-like region; nine CTLA4 derived residues fewer than HS4 (FIG. 19). HS4-A bound B7-1 CHO cells less well than HS4 (FIGS. 19 and 20B). However, addition of the CTLA4 CDR1-like loop (HS8 hybrid), increased B7-1 binding from about 2% to nearly 60% of wild type binding.

On the other hand, addition of the CTLA4 CDR2-like loop into HS4-A (HS 12) did not increase binding relative to HS4-A; neither did addition of all three CTLA4 CDR-like regions (HS13, FIG. 19).

Another hybrid called HS4-B, encoded the CD28 CDR3-like region including the MYPPPY motif followed by CTLA4 residues 113–122 (FIG. 19).

HS4-B and HS4-A displayed similar binding to B7-1. Unlike HS4-A, however, the inclusion of the CTLA4 CDR1-like loop into HS4-B (HS9) did not improve binding (FIG. 19), suggesting that residues immediately adjacent to the CTLA4Ig MYPPPY motif were important determinants in high avidity binding.

Monoclonal antibody binding to CTLA4/CD28Ig hybrid-fusion proteins. The structural integrity of each hybrid fusion protein was examined by assessing their ability to bind mAb's specific for CTLA4 or CD28 in an enzyme immunoassay. The CTLA4 specific mAb's 7F8, 11D4 and 10A8 block ligand binding (Linsley et al. (1992) supra.).

These antibodies bound to each of the CTLA4Ig mutant fusion proteins except 11D4 which failed to bind to P99A and P101A. Since 7F8 and 10A8 bound to these mutants, the lack of binding by 11D4 can probably be attributed to mutagenesis perturbing the epitope recognized by 11D4.

Conversely, each antibody failed to bind to any of the homolog hybrid fusion proteins except 7F8 which bound to HS6, and 11D4 which bound weakly to HS8. As many of these homolog hybrid fusion proteins were, to some extent, able to bind to B7-1, it is likely that lack of binding by the antibodies was due to disruption of conformational epitopes formed by spatially adjacent but non-linear sequences.

The CD28 specific mAb 9.3 (Linsley et al. (1992) supra.) failed to bind to either of the CD28 site-directed mutant fusion proteins but bound to the hybrid fusion proteins HS4, HS4-A, HS7 and HS8. With HS2, weaker binding was observed. No binding was seen with the HS5 and HS6 constructs.

CTLA4 model. FIG. 21 shows a schematic representation of the CTLA4 model. The assignment of CTLA4 residues to CDR-like regions is shown in FIG. 17. The CTLA4 model suggests the presence of an additional (non-Ig) disulfide bond between residues Cys48 and Cys66 which supports the similarity of CTLA4 and the Ig variable fold.

The two possible N-linked glycosylation sites in CTLA4 map to solvent exposed positions of the Ig beta-strand framework regions. 3D-profile analysis indicated that the CTLA4 sequence is overall compatible with an Ig V-fold, albeit more distantly related.

Residue Val114 represents the last residue of the CTLA4Ig-like domain. The conformation of the region between Val114 and the membrane-proximal Cys120 which is thought to form the CTLA4 homodimer is highly variable in the CD28 family. The picture that emerges is that CD28 family members mainly utilize residues in two of three CDR-like regions for binding to B7-1.

The MYPPPY motif represents a conserved scaffold for binding which appears to be augmented by its C-terminal extension and which is specifically modulated by the highly variable CDR1-like region. CDR3 and CDR1-like regions are spatially contiguous in Ig-variable folds. The CDR2 like region is spatially distant and does not, in the case of the CD28 family, significantly contribute to the binding to B7-1.

| DESIGNATION | FRAMEWORK | MODIFICATIONS |
|---|---|---|
| HS1 | CTLA4 | 1–24 OF CD28 |
| | | 97–125 OF CD28 |
| HS2 | CD28 | 1–21 OF CTLA4 |
| | | 95–122 OF CTLA4 |
| HS3 | CTLA4 | 97–125 OF CD28 |
| HS4 | CD28 | 95–122 OF CTLA4 |
| HS4A | CD28 | 95–112 OF CTLA4 |
| HS4B | CD28 | 113–122 OF CTLA4 |
| HS5 | CD28 | 24–31 OF CTLA4 |
| HS6 | CTLA4 | 25–32 OF CD28 |
| HS7 | CD28 | 95–122 OF CTLA4 |
| | | 24–31 OF CTLA4 |
| HS8 | CD28 | 24–31 OF CTLA4 |
| | | 95–112 OF CTLA4 |
| HS9 | CD28 | 24–31 OF CTLA4 |
| | | 113–122 OF CTLA4 |
| HS10 | CD28 | 95–122 OF CTLA4 |
| | | 50–57 OF CTLA4 |
| HS11 | CD28 | 24–31 OF CTLA4 |
| | | 50–57 OF CTLA4 |
| | | 95–122 OF CTLA4 |
| HS12 | CD28 | 50–57 OF CTLA4 |
| | | 95–112 OF CTLA4 |
| HS13 | CD28 | 24–31 OF CTLA4 |
| | | 50–57 OF CTLA4 |
| | | 95–112 OF CTLA4 |
| HS14 | CD28 | 50–57 OF CTLA4 |

TABLE A

CTLA4-Ig/CD28-Ig homolog mutant junction sequences.

| MUTANT | | | | | | | |
|---|---|---|---|---|---|---|---|
| HS1 | -22CKYasp26- | | | | -92ckvEVM99- | | -123CPSDQE- |
| HS2 | -19fvcKYS25- | | | | -94CKIelm97- | | -120cpdDQE- |
| HS3 | | | | | -92ckvEVM99- | | -123CPSDQE- |
| HS4 | | | | | -94CKIe1m97- | | -120cpdDQE- |
| HS5 | -22CKYasp26- | -29ateFRA35- | | | | | -123CPSDQE- |
| HS6 | -21ceySYN27- | -30SREvrv34- | | | | | -120cpdDQE- |
| HS4-A | | | | | -94CKIelm97- | -110tqiHVK118- | -123CPSDQE- |
| HS4-B | | | | | | -113TIIyvi115- | -120cpdDQE- |
| HS7 | -22CKYasp26- | -29ateFRA35- | | | -94CKIelm97- | | -120cpdDQE- |
| HS8 | -22CKYasp26- | -29ateFRA35- | | | -94CKIelm97- | -110tqiHVK118- | -123CPSDQE- |
| HS9 | -22CKYasp26- | -29ateFRA35- | | | | -113TIIyvi115- | -120cpdDQE- |
| HS10 | | | -47VCVaty52- | -55gneLQV60- | -94CKIelm97- | | -120cpdDQE- |
| HS11 | -22CKYasp26- | -29ateFRA35- | -47VCVaty52- | -55gneLQV60- | -94CKIelm97- | | -120cpdDQE- |
| HS12 | | | -47VCVaty52- | -55gneLQV60- | -94CKIelm97- | -110tqiHVK118- | -123CPSDQE- |
| HS13 | -22CKYasp26- | -29ateFRA35- | -47VCVaty52- | -55gneLQV60- | -94CKIelm97- | -110tqiHVK118- | -123CPSDQE- |
| HS14 | | | -47VCVaty52- | -55gneLQV60- | | | -123CPSDQE- |

Junction sequences of the CTLA4/CD28-Ig hybrid fusion proteins. Amino acids are denoted by their single letter code with those in upper case being CD28 residues, those in lower case being CTLA4 residues and those in bold upper case being human IgGI residues.
Numbering is from the mature N-terminal of the respective proteins and refer to the adjacent amino acid in the table.

TABLE B. Binding of CTLA4 and CD28 monoclonal antibodies to CTLA4Ig and CD28Ig mutant fusion proteins and to CTLA4/CD28Ig hybrid fusion proteins.

TABLE B

Binding of CTLA4 and CD28 monoclonal antibodies to CTLA4Ig and CD28Ig mutant fusion proteins and to CTLA4/CD28Ig hybrid fusion proteins

|  | anti-CTLA4 mAbs | | anti-CD28 mAb | |
|---|---|---|---|---|
|  | 7F8 | 11D4 | 10A8 | 9.3 |
| CTLA4Ig MUTANT FUSION PROTEIN | | | | |
| AVPPPY (SEQ ID NO.: 36) | +++ | +++ | +++ | − |
| MAPPPY (SEQ ID NO.: 37) | ++ | + | ++ | − |
| MYAPPY (SEQ ID NO.: 38) | + | − | + | − |
| MYPAPY (SEQ ID NO.: 39) | +++ | ++++++ | +++ | − |
| MYPPAY (SEQ ID NO.: 40) | +++ | − | + | − |
| MYPPPA (SEQ ID NO.: 41) | +++ | ++ | +++ | − |
| AAPPPY (SEQ ID NO.: 42) | + | ++ | +++ | − |
| CD28Ig MUTANT FUSION PROTEIN | | | | |
| MYPPAY (SEQ ID NO.: 40) | − | − | − | − |
| MYPPPA (SEQ ID NO.: 41) | − | − | − | + |
| CTLA4/CD28Ig HYBRID FUSION PROTEINS | | | | |
| HS1 | − | − | − | − |
| HS2 | − | − | − | + |
| HS3 | − | − | − | − |
| HS4 | − | − | − | +++ |
| HS5 | − | − | − | − |
| HS6 | + | − | − | − |
| HS4-A | − | − | − | ++ |
| HS4-B | − | − | − | ++ |
| HS7 | − | − | − | +++ |
| HS8 | − | + | − | +++ |
| HS9 | − | + | − | − |
| HS10 | − | − | − | − |
| HS11 | − | − | − | + |
| HS12 | − | − | − | − |
| HS13 | − | − | − | − |
| HS14 | − | − | − | − |
| CTLA4Ig | +++ | +++ | +++ | − |
| CD28Ig | − | − | − | +++ |

Antibody binding was rated from that seen for wild type protein (+++) to above background (+), and no detectable binding (−).

EXAMPLE 8

The following provides a description of the methods used to generate the nucleotide sequences encoding the soluble CTLA4 mutant molecules having one or more substitution mutations in the extracellular CTLA4 portion. SA single-site mutants L104EIg were as generated and tested for binding kinetics for CD80 and/or CD86. Numerous single-site mutants were generated. The single-site mutants that were tested for binding to CD80 and CD86, or tested for allostimulation include the following: L104EIg (FIG. 23) and L104SIg. The L104EIg single-site mutant was used as a template to generate numerous double-site mutant CTLA4 sequences, including L104EA29YIg (FIG. 24), L104EA29LIg (FIG. 25), L104EA29TIg (FIG. 26), L104EA29WIg (FIG. 27), L104EG105FIg, and L104ES25RIg. Triple-site mutants were also generated, including L104EA29YS25KIg and L104EA29YS25RIg. The L104EIg nucleotide sequence was used as a template to generate the double-site mutant CTLA4 sequence, L104EA29YIg, which was tested for binding kinetics.

CTLA4Ig Codon Based Mutagenesis:

Single-site mutant nucleotide sequences were generated using CTLA4Ig (U.S. Pat. Nos. 5,844,095; 5,851,795; and 5,885,796) as a template. Mutagenic CTLA4Ig oligonucleotide PCR primers were designed for random mutagenesis of a specific codon by allowing any base at positions 1 and 2 of the codon, but only guanine or thymine at position 3 (XXG/T). In this manner, a specific codon encoding an amino acid could be randomly mutated to code for each of the 20 amino acids. PCR products encoding mutations in close proximity to E95-G107 of CTLA4Ig (FIG. 22), were digested with SacI/XbaI and subcloned into similarly cut CTLA4Ig πLN expression vector. This method was used to generate numerous nucleotide sequences encoding single-site CTLA4 mutant molecules (Example 9). The functional properties of some of the CTLA4 single-site mutants was analyzed (see Example 9). Some of the single-site mutants were identified as CTLA4 mutants of interest and were sequenced (see Example 8).

L104EIg was identified as a CTLA4 mutant molecule of interest (e.g, having single-site mutation). To generate double-site CTLA4 mutant molecules, the nucleotide sequence encoding L104EIg was used as a template for mutagenesis in proximity to S25-R33 of CTLA4Ig (e.g., serine at position +25 through arginine at position +33), a silent NheI restriction site was first introduced 5' to this region, by PCR primer-directed mutagenesis. PCR products were digested with NheI/XbaI and subcloned into similarly cut CTLA4Ig or L104EIg or L104EIg expression vectors. The functional properties of some of the CTLA4 double-site mutants was analyzed (see Example 9). Some of the double-site mutants were identified as CTLA4 mutants of interest and were sequenced (see Example 8).

L104E29YIg was identified as a CTLA4 molecule of interest (e.g., having double-site mutations). The nucleotide sequence encoding L104E29YIg was used to generate triple-site CTLA mutant molecules. The functional properties of some of the CTLA4 triple-site mutants was analyzed. Some of the triple-site mutants were sequenced (see Example 8).

This method was used to generate the double-site CTLA4 mutant molecule L104EA29YIg (FIG. 7).

EXAMPLE 9

The following provides a description of the methods used to identify the single- and double-and double-site mutant CTLA polypeptides, expressed from the constructs described in Example 8, that exhibited binding to CD80 and/or CD86 antigens.

Current in vitro and in vivo studies indicate that CTLA4Ig by itself is unable to completely block the priming of antigen specific activated T cells. In vitro studies with CTLA4Ig and either monoclonal antibody specific for CD80 or CD86 measuring inhibition of T cell proliferation indicate that anti-CD80 monoclonal antibody did not augment CTLA4Ig inhibition. However, anti-CD86 monoclonal antibody did, indicating that CTLA4Ig was not as effective at blocking CD86 interactions. These data support earlier findings by Linsley et al. (*Immunity*, 1994, 1:793–801) showing inhibition of CD80-mediated cellular responses required approximately 100 fold lower CTLA4Ig concentrations than for CD86-mediated responses. Based on these findings, it was surmised that soluble CTLA4 mutant molecules having a higher avidity for CD86 than wild type CTLA4 should be better able to block the priming of antigen specific activated cells than CTLA4Ig.

To this end, the soluble CTLA4 mutant molecules described in Example 8 above were screened using a novel screening procedure to identify several mutations in the extracellular domain of CTLA4 that improve binding avidity for CD80 and CD86.

In general, COS cells were transfected with individual miniprep plasmid cDNA and three day conditioned culture media applied to BIAcore biosensor chips (Pharmacia Biotech AB, Uppsala, Sweden) coated with soluble CD80Ig or CD86Ig. The specific binding and dissociation of mutant proteins was measured by surface plasmon resonance (O'Shannessy, D. J., et al., 1997 Anal. Biochem. 212: 457–468).

Screening Method

COS cells grown in 24 well tissue culture plates were transiently transfected with mutant CTLA4Ig and culture media collected 3 days later.

Conditioned COS cell culture media was allowed to flow over BIAcore biosensor chips derivatized with CD86Ig or CD80Ig, and mutant molecules were identified with off rates slower than that observed for wild type CTLA4Ig. The cDNAs corresponding to selected media samples were sequenced and DNA was prepared from these cDNAs to perform larger scale COS cell transient transfection, from which mutant CTLA4Ig protein was prepared following protein A purification of culture media.

BIAcore analysis conditions and equilibrium binding data analysis were performed as described in J. Greene et al. 1996 J. Biol. Chem. 271:26762.

BIAcore Data Analysis

Senosorgram baselines were normalized to zero response units (RU) prior to analysis. Samples were run over mock-derivatized flow cells to determine background RU values due to bulk refractive index differences between solutions. Equilibrium dissociation constants ($K_d$) were calculated from plots of $R_{eq}$ versus C, where $R_{eq}$ is the steady-state response minus the response on a mock-derivatized chip, and C is the molar concentration of analyte. Binding curves were analyzed using commercial nonlinear curve-fitting software (Prism, GraphPAD Software).

Experimental data were first fit to a model for a single ligand binding to a single receptor (1-site model, i.e., a simple langmuir system, A+B<–>AB), and equilibrium association constants ($K_d=[A]\cdot[B]\setminus[AB]$) were calculated from the equation $R=R_{max}\cdot C/(K_d+C)$. Subsequently, data were fit to the simplest two-site model of ligand binding (i.e., to a receptor having two non-interacting independent binding sites as described by the equation $R=R_{max1}\cdot C\setminus(K_{d1}+C)+R_{max2}\cdot C\setminus(K_{d2}+C)$.

The goodness-of-fits of these two models were analyzed visually by comparison with experimental data and statistically by an F test of the sums-of-squares. The simpler one-site model was chosen as the best fit unless the two-site model fit significantly better (p<0.1).

Association and disassociation analyses were performed using BIA evaluation 2.1 Software (Pharmacia). Association rate constants $k_{on}$ were calculated in two ways, assuming both homogenous single-site interactions and parallel two-site interactions. For single-site interactions, $k_{on}$ values were calculated according to the equation $R_t=R_{eq}(1-\exp^{-ks(t-t_0)})$, where $R_t$ is a response at a given time, t; $R_{eq}$ is the steady-state response; $t_0$ is the time at the start of the injection; and $k_s=dR/dt=k_{on}\cdot Ck_{off}$, where C is a concentration of analyte, calculated in terms of monomeric binding sites. For two-site interactions $k_{on}$ values were calculated according to the equation $R_t=R_{eq1}(1-\exp^{-ks1(t-t_0)})+R_{eq2}(1-\exp^{ks2(t-t_0)})$.

For each model, the values of $k_{on}$ were determined from the calculated slope (to about 70% maximal association) of plots of $k_s$ versus C.

Dissociation data were analyzed according to one site (AB=A+B) or two sites (AiBj=Ai+Bj) models, and rate constants ($k_{off}$) were calculated from best fit curves. The binding site model was used except when the residuals were greater than machine background (2-10RU, according to machine), in which case the two-binding site model was employed. Half-times of receptor occupancy were calculated using the relationship $t_{1/2}=0.6/k_{off}$.

TABLE I

Equilibrium binding constants (See also FIG. 28)

| | CD80Ig (Kd) | CD86Ig (Kd) |
|---|---|---|
| CTLA4Ig | 6.51 ± 1.08 | 13.9 ± 2.27 |
| L104EIg | 4.47 ± 0.36 | 6.06 ± 0.05 |
| L104EA29YIg | 3.66 ± 0.41 | 3.21 ± 0.23 |

BIAcore™ Analysis: All experiments were run on BIAcore™ or BIAcore™ 2000 biosensors (Pharmacia Biotech AB, Uppsala) at 25° C. Ligands were immobilized on research grade NCM5 sensor chips (Pharmacia) using standard N-ethyl-N'-(dimethylaminopropyl) carbodiimidN-hydroxysuccinimide coupling (Johnsson, B., et al. 1991 Anal. Biochem. 198: 268–277; Khilko, S. N., et al. 1993 J. Biol. Chem 268:5425–15434).

TABLE II

BIAcore analysis of Single-site CTLA4Ig mutants binding to CD86

| Single-site Mutant: | % of Mutants that Bind: | % Mutant Non-binding: |
|---|---|---|
| S25 | 95 | 5 |
| P26 | 94 | 6 |
| G27 | 91 | 9 |
| K28 | 57 | 43 |
| A29 | 74 | 26 |
| T30 | 95 | 5 |
| E31 | 5 | 95 |
| R33 | 5 | 95 |
| K93 | 78 | 22 |
| L96 | 81 | 19 |
| M97 | 4 | 96 |
| Y98 | 2 | 98 |
| P99 | 20 | 80 |
| P100 | 11 | 89 |
| P101 | 28 | 72 |
| Y102 | 2 | 98 |
| Y103 | 84 | 16 |
| L104 | 94 | 6 |
| G105 | 55 | 45 |
| I106 | 75 | 25 |
| G107 | 90 | 10 |
| Q111 | 95 | 5 |
| Y113 | 95 | 5 |
| I115 | 95 | 5 |

TABLE III

BIAcore analysis of Double-site CTLA4Ig mutants binding to CD86.

| Double-site Mutants: | % of Mutants that Bind: | % Mutant Non-binding: |
|---|---|---|
| L104ES25 | 95 | 5 |
| L104EP26 | 93 | 7 |

TABLE III-continued

BIAcore analysis of Double-site CTLA4Ig mutants binding to CD86.

| Double-site Mutants: | % of Mutants that Bind: | % Mutant Non-binding: |
|---|---|---|
| L104EG27 | 92 | 8 |
| L104EK28 | 70 | 30 |
| L104EA29 | 94 | 6 |
| L104ET30 | 95 | 5 |
| L104EK93 | 82 | 18 |
| L104EG105 | 94 | 6 |
| L104EI106 | 92 | 8 |
| L104EG107 | 90 | 10 |

TABLE IV

BIAcore analysis of Triple-site CTLA4Ig mutants binding to CD86

| Triple-site mutants: | % of Mutants that Bind: | % Mutant Non-binding: |
|---|---|---|
| L104EA29YS25 | 95 | 5 |
| L104EA29YP26 | 93 | 7 |
| L104EA29YG27 | 95 | 5 |
| L104EA29YK28 | 81 | 19 |
| L104EA29YT30 | 92 | 8 |
| L104EA29YL98 | 96 | 4 |

Flow Cytometry:

Murine MAb L307.4 (anti-CD80) was purchased from Becton Dickinson (San Jose, Calif.) and IT2.2 (anti-B7-0 [also known as CD86]), from Pharmingen (San Diego, Calif.). For immunostaining, CD80 and/or CD86 +CHO cells were removed from their culture vessels by incubation in phosphate-buffered saline containing 10 mM EDTA. CHO cells ($1-10\times10^5$) were first incubated with MAbs or immunoglobulin fusion proteins in DMEM containing 10% fetal bovine serum (FBS), then washed and incubated with fluorescein isothiocyanate-conjugated goat anti-mouse or anti-human immunoglobulin second step reagents (Tago, Burlingame, Calif.). Cells were given a final wash and analyzed on a FACScan (Becton Dickinson).

FACS analysis (FIGS. 29A and B) of CTLA4Ig and mutant molecules binding to stably transfected CD80+ and CD86+CHO cells was performed as described herein.

CD80+ and CD86+ CHO cells were incubated with increasing concentrations of CTLA4Ig, washed and bound immunoglobulin fusion protein was detected using fluorescein isothiocyanate-conjugated goat anti-human immunoglobulin.

In FIG. 29, L104EA29YIg (circles), or L104EIg (triangle) CHO cells ($1.5\times10^5$) were incubated with the indicated concentrations of CTLA4Ig (closed square), L104EA29YIg (circles), or L104EIg (triangle) for 2 hr. at 23° C., washed, and incubated with fluorescein isothiocyanate-conjugated goat anti-human immunoglobulin antibody. Binding on a total of 5,000 viable cells was analyzed (single determination) on a FACScan, and mean fluorescence intensity (MFI) was determined from data histograms using PC-LYSYS. Data have been corrected for background fluorescence measured on cells incubated with second step reagent only (MFI=7). Control L6 MAb (80 μg/ml) gave MFI<30. This is representative of four independent experiments.

The binding of L104EG105FIg, L104EIg, and CTLA4Ig (FIGS. 35A and B), or the binding of L104ES25RIg, L104EIg, and CTLA4Ig (FIGS. 37A and B) to CHO cells stably transfected with human CD80 or CD86 were also compared. The transfected CHO cells were incubated with increasing concentrations of proteins for 2 hours at 23 degrees C., washed and incubated with fluorescein-conjugated goat anti-human IgG. Binding on a total of 5,000 viable cells was analyzed on a FACScan, and mean fluorescence intensity determined from data histograms using PC-LYSYS.

Functional Assays:

Human CD4+T cells were isolated by immunomagnetic negative selection (Linsley et al., 1992 J. Exp. Med. 176: 1595–1604).

Inhibition of PMA plus CD80-CHO or CD86-CHO T cell stimulation (FIGS. 30A and B) was performed, comparing CTLA4Ig and L104EA29YIg. CD4+T cells ($8-10\times10^4$/well) were cultured in the presence of 1 nM PMA with or without irradiated CHO cell stimulators. Proliferative responses were measured by the addition of 1 μCi/well of [$^3$H] thymidine during the final 7 hr. of a 72 hr. culture.

Figure 34B:
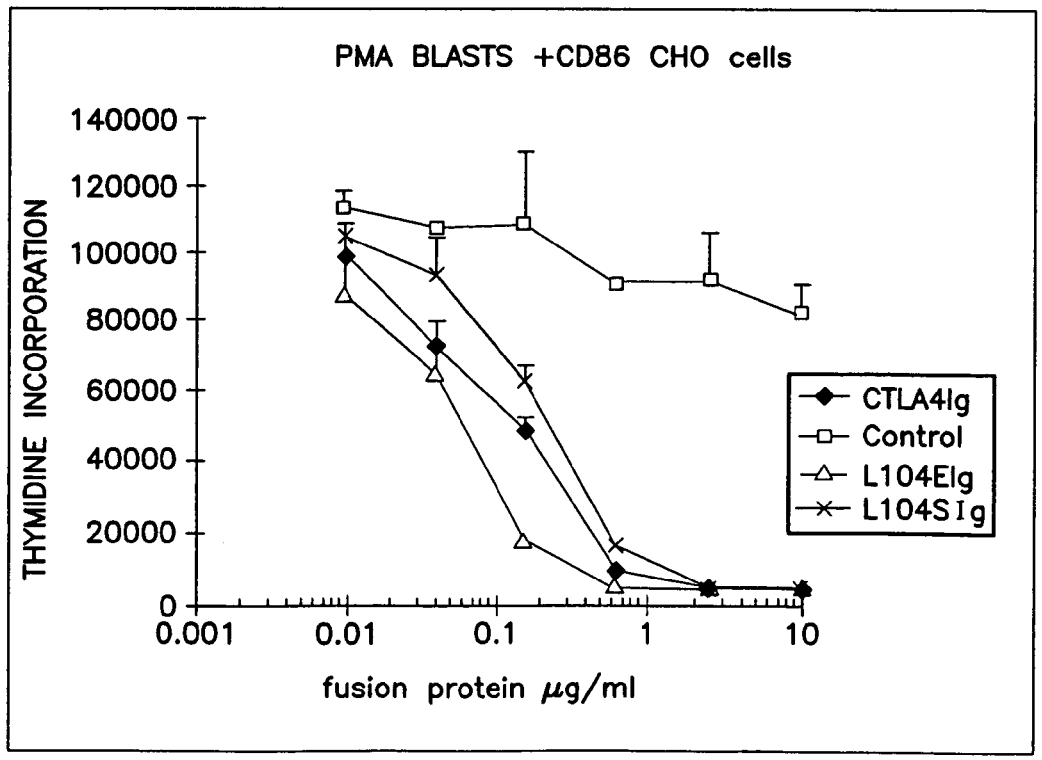

The effect of L104SIg, L104EIg, and CTLA4 were also compared. The effects of increasing concentrations of CTLA4Ig, L104EIg, L104SIg, or isotype matched negative control were measured on stably transfected CD80-CHO (FIG. 34A) and CD86-CHO cell costimulation of PMA-stimulated peripheral blood CD4+ T cells. T cells ($5.0\times10^4$ cells/well) stimulators (FIG. 34B). Proliferation was measure by the addition of 1.0 micro Ci/well of $^3$H-thymidine during the final 7 hours of a 72 hour culture. The symbols for L104EA29YIg (open circle), CTLA4Ig (closed square), and control (open triangle) represent means (±standard deviations) of triplicate determinations.

FIGS. 31 A and B, and 26 A and B show inhibition of allostimulated human T cells prepared above, and allostimulated with a human B LCL line called PM. T cells at $3.0\times10^4$/well and PM at $8.0\times10^3$/well. Primary allostimulation occurred for 6 days then the cells were pulsed with $^3$H-thymidine for 7 hours before incorporation of radiolabel was determined. Secondary allostimulation was performed as follows. Seven day primary allostimulated T cells were harvested over LSM (Ficol) and rested for 24 hours. T cells then restimulated (secondary) by adding PM in same ratio as above. Stimulation occurred for 3 days, then the cells were pulsed with radiolabel and harvested as above. To measure cytokine production (FIGS. 32 A and B), duplicate secondary allostimulation plates were set up. After 3 days, culture media was assayed using Biosource kits using conditions recommended by manufacturer.

The inhibition of proliferation of primary allostimulated Tcells was also performed using L104EIg and L104EG105FIg (FIG. 36). Purified CD4+ cells ($5.0\times10^4$ cells/well) were incubated with an irratiated LCL allogeneci B cell line ($1.0\times10^4$ cells/well) in the presence of increasing concentrations of CTLA4Ig, L104EIg, L104EG105FIg, or isotype negative control. Proliferation was measure by $^3$H-thymidine incorporation over the final 7 hours of a 6 day assay. Symbols for CTLA4Ig (closed diamond), control (closed square), L104EIg (open triangle), and L104EG105FIg (open square) represent means (±standard deviations) of triplicate determinations.

Monkey MLR (FIG. 33). PBMC'S from 2 monkeys purified over LSM and mixed ($3.5\times10^4$ cells/well from each monkey) with 2 ug/ml PHA. Stimulated 3 days then pulsed with radiolabel 16 hours before harvesting.

EXAMPLE 10

The following provides a description of the methods used to generate the soluble CTLA4 mutants, using phage display techniques.

High Avidity Mutagenesis of CTLA4Ig through Phage Display System

Recombinant phage display technology was performed to select CTLA4Ig mutant molecules which bind to CD80 and/or CD86. This method was used to screen millions of CTLA4 mutants, express them on the surface of phage particles, and select strong CD86Ig binders by a panning procedure. The pCANTAB 5E phagemid system (Pharmacia Biotech) was used in this study.

Expression of Wild Type CTLA4X (Extracellular Domain) in pCANTAB 5E Phase Display System Cloning:

The region encoding the complete CTLA4 extracellular domain was cloned into pCANTAB 5E vector to create a fusion protein with Gene III (phage coat protein). The pCANTAB 5E -CTLA4 X was transformed into TG1 *E. coli* bacterial cells.

Phage Rescue:

The bacteria containing the vector encoding the wild-type CTLA4-Gene III fusion protein was infected with helper phage. Phage particles were assembled in bacteria and released into the media. Each phage particle was expressed approximately 1 CTLA4-Gene III fusion protein on the surface. 0.1 ml of bacterial culture was added to 5 ml of 2× TY AG medium, the bacteria were grown at 30 degrees C. for 2 hours. 0.25 ml of M13K07 helper phage ($5\times10^{10}$/ml ) was added, the cells were shaked at 37 degrees C., 250 rpm for 1 hr. The cells were spun down and the supernatant was discarded. The cell pellet was resuspended in 5 ml 2× YT AK medium, shaken at 250 rpm, 37 degrees C. overnight. The cells were spun down and saved as the supernatant as phage stock.

Mutagenesis of CTLA4X

Mutation sites occurred in a region encompassed by tyrosine at position +23 through threonine at position +30 (e.g., Y23-T30). All amino acids residues within the Y23-T30 were mutated to each of the 20 amino acids, yielding a total diversity of nucleotide sequences of about $2.8\times10^{14}$.

Mutagenesis and Preparation of Phage Display Library

From tyrosine +23 to threonine +30, a pool of degenerate forward primers were generated having the following sequence:

5' CGA GGC ATC GCT AGC TTT GTG TGT GAG XXK XXK XXK XXK XXK XXK XXK XXK GAG GTC CGG GTG ACA GT 3' (SEQ ID NO.: 43)

Where X=any of the four nucleotides A, T, G, or C and K=either T, G, or C Each primer contained a Nhe I restriction enzyme cut site.

The reverse primer had the following sequence:

5' GGT TGC CGC ACA GAC TTC GGT CAC CTG GCT GTC AGC CTG CCG AAG CAC TGT CAC CCG GA 3' (SEQ ID NO.: 44).

This primer contained a Bste II restriction enzyme cut site.

By PCR, mutagenic inserts were prepared using the degenerate primers and the standard reverse primer. These inserts were digested with Nhe I and Bste II and ligated into pCANTAB-CX2 phagemid digested with the same enzymes and transformed into TG1 cells.

Preparation of Mutated B-C Loop-pCANTAB-CX2 Library:

45 electroporations were performed at 1.7 KV, 300 Ω, 251 μF, 4.5 ms with Bio-Rad Gene Pulser. The library size was $10^{12}$.

Phage Rescue:

Ten ml of amplified library cells were added to 40 ml 2× YT-G-A, the cells were grown from OD 0.115 to 0.332 at 37 degrees C. Total cells=$0.332\times10^{9}\times50=1.66\times10^{10}$ M13K07 helper phage ($20\times1.66\times10^{10}=3.32\times10^{11}$) were added to the culture and incubated at 30 degrees C. with shaking for 1.5 hours. The culture was spun down and the supernatant removed. The cells were resuspended into 50 ml 2×TY A-K medium and incubated at 30 degrees C. with shaking at 250 rpm overnight. The cells were spun down and the supernatant was saved. The phage was PEG precipitated from the supernatant. The precipitated phage was used for the first round panning procedure.

Panning:

The phage particles expressing a mutant CTLA4-Gene III fusion protein were allowed to bind to CD86 immobilized on plastic. The strong binders were preferentially selected and enriched. A 96-well plate was coated with CD86Ig at 4 micro grams/well at 4 degrees C. overnight. The wells were blocked with PBS-milk for 2 hours. The phage were mixed with equal volumes of PBS-milk and incubated at room temperature for 30 minutes. 200 micro liters of phage mixture was added to each well and incubated for 2 hours. The wells were washed with PBS tween and eluted with glycine buffer pH 2.2. The eluted phage were collected, used to reinfect TG1 cells, rescued and panned several times.

| Panning results: | | |
|---|---|---|
| 1st round: | Input phage | $6\times10^{11}$ |
| | Wash(×7) | $2.8\times10^{8}$ |
| | Elute | $3\times10^{8}$ |
| 2nd round: | Input phage | $4.8\times10^{11}$ |
| | Wash 10 | $7\times10^{7}$ |
| | Elute | $4.5\times10^{7}$ |
| 3rd round: | Input phage | $1\times10^{12}$ |
| | Wash 12 | $2\times10^{7}$ |
| | Elute | $3\times10^{7}$ |
| 4th round: | Input phage | $4\times10^{11}$ |
| | Wash 15 | $2\times10^{7}$ |
| | Elute | $1\times10^{9}$ |
| 5th round: | Input phage | $8\times10^{11}$ |
| | Wash 35 | $7\times10^{7}$ |
| | Elute | $5\times10^{9}$ |

Five mutants were enriched through these 5 rounds of panning.

Mut 9 F-E-P-K-R-G-V-Q (SEQ ID NO.: 45)

Mut 19 W-D-Q-Y-T-G-Y-G (SEQ ID NO.: 46)

Mut 71 W-D-A-Y-R-N-Q-Q (SEQ ID NO.: 47)

Mut 45 Y-D-H-P-Y-D-G-Q (SEQ ID NO.: 48)

Mut 4 W-D-Q-H-V-S-R-R (SEQ ID NO.: 49)

CTLA4 Y-A-S-P-G-K-A-T (SEQ ID NO.: 50)

What is claimed is:

1. A CTLA4Ig fusion protein reactive with B7 antigen and encoded by DNA deposited as ATCC 68629.

2. A CTLA4Ig fusion protein having the amino acid sequence of a CTLA4Ig fusion protein expressed by a cell deposited as ATCC 10762, wherein said CTLA4Ig fusion protein is reactive with B7 antigen.

3. A CTLA4Ig fusion protein expressed by a cell deposited as ATCC Accession No. 10762.

4. A CTLA4Ig fusion protein secreted by a cell deposited as ATCC Accession No. 10762.

5. A CTLA4Ig fusion protein having the amino acid sequence of a CTLA4Ig fusion protein secreted by a cell deposited as ATCC Accession No. 10762, wherein said CTLA4Ig fusion protein is reactive with B7 antigen.

6. The CTLA4Ig fusion protein of claim 1, 2, 3, 4, or 5, wherein the CTLA4Ig fusion protein exists as a dimer.

7. The CTLA4Ig fusion protein of claim 6, wherein the CTLA4Ig fusion protein exists as a homodimer.

8. The soluble CTLA4Ig fusion protein of claim 1, 2, 3, 4, or 5 comprising one or more glycosylated amino acid residues.

9. The CTLA4Ig fusion protein of claim 1, 2, 3, 4, or 5, having a molecular weight of about 100 kDa.

10. The CTLA4Ig fusion protein of claim 1, 2, 3, 4, or 5, wherein the CTLA4Ig is purified.

11. The CTLA4Ig fusion protein of claim 1, 2, 3, 4, or 5, wherein the CTLA4Ig is isolated.

12. A pharmaceutical composition comprising the CTLA4Ig fusion protein of claim 1, 2, 3, 4, or 5.

* * * * *

UNITED STATES PATENT AND TRADEMARK OFFICE
CERTIFICATE OF CORRECTION

PATENT NO. : 7,105,166 B1  Page 1 of 1
APPLICATION NO. : 09/609915
DATED : August 23, 2006
INVENTOR(S) : Bajorath Jurgen et al.

It is certified that error appears in the above-identified patent and that said Letters Patent is hereby corrected as shown below:

Title page, item
(75) Inventors:

"Philip Wallace" should be deleted

Signed and Sealed this

Thirteenth Day of February, 2007

JON W. DUDAS
*Director of the United States Patent and Trademark Office*

UNITED STATES PATENT AND TRADEMARK OFFICE
CERTIFICATE OF CORRECTION

PATENT NO.        : 7,105,166 B1                                     Page 1 of 1
APPLICATION NO. : 09/609915
DATED             : September 12, 2006
INVENTOR(S)       : Bajorath Jurgen et al.

It is certified that error appears in the above-identified patent and that said Letters Patent is hereby corrected as shown below:

Title page, item
(75) Inventors:

"Philip Wallace" should be deleted

This certificate supersedes Certificate of Correction issued February 13, 2007.

Signed and Sealed this

Sixth Day of March, 2007

JON W. DUDAS
*Director of the United States Patent and Trademark Office*

SEQUENCE LISTING

<160> NUMBER OF SEQ ID NOS: 50

<210> SEQ ID NO 1
<211> LENGTH: 636
<212> TYPE: DNA
<213> ORGANISM: Homo sapiens

<400> SEQUENCE: 1

```
atgggtgtac tgctcacaca gaggacgctg ctcagtctgg tccttgcact cctgtttcca      60
agcatggcga gcatggcaat gcacgtggcc cagcctgctg tggtactggc cagcagccga     120
ggcatcgcca gctttgtgtg tgagtatgca tctccaggca aagccactga ggtccgggtg     180
acagtgcttc ggcaggctga cagccaggtg actgaagtct gtgcggcaac ctacatgatg     240
gggaatgagt tgaccttcct agatgattcc atctgcacgg gcacctccag tggaaatcaa     300
gtgaacctca ctatccaagg actgagggcc atggacacgg actctacat ctgcaaggtg      360
gagctcatgt acccaccgcc atactacctg gcataggca acggaaccca gatttatgta      420
attgatccag aaccgtgccc agattctgac ttcctcctct ggatccttgc agcagttagt     480
tcggggttgt ttttttatag ctttctcctc acagctgttt ctttgagcaa aatgctaaag     540
aaaagaagcc ctcttacaac aggggtctat gtgaaaatgc ccccaacaga gccagaatgt     600
gaaaagcaat ttcagcctta ttttattccc atcaat                              636
```

<210> SEQ ID NO 2
<211> LENGTH: 212
<212> TYPE: PRT
<213> ORGANISM: Homo sapiens

<400> SEQUENCE: 2

```
Met Gly Val Leu Leu Thr Gln Arg Thr Leu Leu Ser Leu Val Leu Ala
 1               5                  10                  15

Leu Leu Phe Pro Ser Met Ala Ser Met Ala Met His Val Ala Gln Pro
            20                  25                  30

Ala Val Val Leu Ala Ser Ser Arg Gly Ile Ala Ser Phe Val Cys Glu
        35                  40                  45

Tyr Ala Ser Pro Gly Lys Ala Thr Glu Val Arg Val Thr Val Leu Arg
    50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                85                  90                  95

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
        115                 120                 125

Tyr Leu Gly Ile Gly Asn Gly Thr Gln Ile Tyr Val Ile Asp Pro Glu
    130                 135                 140

Pro Cys Pro Asp Ser Asp Phe Leu Leu Trp Ile Leu Ala Ala Val Ser
145                 150                 155                 160

Ser Gly Leu Phe Phe Tyr Ser Phe Leu Leu Thr Ala Val Ser Leu Ser
                165                 170                 175

Lys Met Leu Lys Lys Arg Ser Pro Leu Thr Thr Gly Val Tyr Val Lys
            180                 185                 190

Met Pro Pro Thr Glu Pro Glu Cys Glu Lys Gln Phe Gln Pro Tyr Phe
```

```
                195                 200                 205
Ile Pro Ile Asn
    210

<210> SEQ ID NO 3
<211> LENGTH: 223
<212> TYPE: PRT
<213> ORGANISM: Homo sapiens

<400> SEQUENCE: 3

Met Ala Cys Leu Gly Phe Gln Arg His Lys Ala Gln Leu Asn Leu Ala
1               5                   10                  15

Ala Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220

<210> SEQ ID NO 4
<211> LENGTH: 223
<212> TYPE: PRT
<213> ORGANISM: Mus musculus

<400> SEQUENCE: 4

Met Ala Cys Leu Gly Leu Arg Arg Tyr Lys Ala Gln Leu Gln Leu Pro
1               5                   10                  15

Ser Arg Thr Trp Pro Phe Val Ala Leu Leu Thr Leu Leu Phe Ile Pro
            20                  25                  30

Val Phe Ser Glu Ala Ile Gln Val Thr Gln Pro Ser Val Tyr Leu Ala
        35                  40                  45

Ser Ser His Gly Tyr Ala Ser Phe Pro Cys Glu Tyr Ser Pro Ser His
    50                  55                  60

Asn Thr Asp Glu Val Arg Val Thr Val Leu Arg Gln Thr Asn Asp Gln
65                  70                  75                  80

Met Thr Glu Val Cys Ala Thr Thr Phe Thr Glu Lys Asn Thr Val Gly
```

```
                 85                  90                  95
Phe Leu Asp Tyr Pro Phe Cys Ser Gly Thr Phe Asn Glu Ser Arg Val
            100                 105                 110
Asn Leu Thr Ile Gln Gly Leu Arg Ala Val Asp Thr Gly Leu Tyr Leu
            115                 120                 125
Cys Lys Val Glu Leu Met Tyr Pro Pro Tyr Phe Val Gly Met Gly
            130                 135                 140
Asn Gly Thr Gln Ile Tyr Ile Asp Pro Glu Pro Cys Pro Asp Ser
145                 150                 155                 160
Asp Phe Leu Leu Trp Ile Leu Tyr Ala Val Ser Leu Gly Leu Phe Phe
                165                 170                 175
Tyr Ser Phe Leu Val Ser Ala Val Ser Leu Ser Lys Met Leu Lys Lys
                180                 185                 190
Arg Ser Pro Leu Thr Thr Gly Val Tyr Val Lys Met Pro Pro Thr Glu
                195                 200                 205
Pro Glu Cys Glu Lys Gln Phe Gln Pro Tyr Phe Ile Pro Ile Asn
            210                 215                 220

<210> SEQ ID NO 5
<211> LENGTH: 218
<212> TYPE: PRT
<213> ORGANISM: Mus musculus

<400> SEQUENCE: 5

Met Thr Leu Arg Leu Leu Phe Leu Ala Leu Asn Phe Phe Ser Val Gln
1               5                   10                  15
Val Thr Glu Asn Lys Ile Leu Val Lys Gln Ser Pro Leu Leu Tyr Val
                20                  25                  30
Asp Ser Asn Glu Val Ser Leu Ser Cys Arg Tyr Ser Tyr Asn Leu Leu
            35                  40                  45
Ala Lys Glu Phe Arg Ala Ser Leu Tyr Lys Gly Val Asn Ser Asp Val
        50                  55                  60
Glu Val Cys Val Gly Asn Gly Asn Phe Thr Tyr Gln Pro Gln Phe Arg
65                  70                  75                  80
Ser Asn Ala Glu Phe Asn Cys Asp Gly Asp Phe Asp Asn Glu Thr Val
                85                  90                  95
Thr Phe Arg Leu Trp Asn Leu His Val Asn His Thr Asp Ile Tyr Phe
            100                 105                 110
Cys Lys Ile Glu Phe Met Tyr Pro Pro Tyr Leu Asp Asn Glu Arg
        115                 120                 125
Ser Asn Gly Thr Ile Ile His Ile Lys Glu Lys His Leu Cys His Thr
130                 135                 140
Gln Ser Ser Pro Lys Leu Phe Trp Ala Leu Val Val Ala Gly Val
145                 150                 155                 160
Leu Phe Cys Tyr Gly Leu Leu Val Thr Val Ala Leu Cys Val Ile Trp
                165                 170                 175
Thr Asn Ser Arg Arg Asn Arg Leu Leu Gln Val Thr Tyr Met Asn Met
            180                 185                 190
Thr Pro Arg Arg Pro Gly Leu Thr Arg Lys Pro Tyr Gln Pro Tyr Ala
            195                 200                 205
Pro Ala Arg Asp Phe Ala Ala Tyr Arg Pro
        210                 215

<210> SEQ ID NO 6
<211> LENGTH: 218
```

<212> TYPE: PRT
<213> ORGANISM: Rattus norvegicus

<400> SEQUENCE: 6

```
Met Thr Leu Arg Leu Leu Phe Leu Ala Leu Ser Phe Ser Val Gln
1               5                   10                  15

Val Thr Glu Asn Lys Ile Leu Val Lys Gln Ser Pro Leu Leu Val Tyr
            20                  25                  30

Asp Asn Asn Glu Val Ser Leu Ser Cys Arg Tyr Ser Tyr Asn Leu Leu
            35                  40                  45

Ala Lys Glu Phe Arg Ala Ser Leu Tyr Lys Gly Val Asn Ser Asp Val
    50                  55                  60

Glu Val Cys Val Gly Asn Gly Asn Phe Thr Tyr Gln Pro Gln Phe Arg
65                  70                  75                  80

Pro Asn Val Gly Phe Asn Cys Asp Gly Asn Phe Asp Asn Glu Thr Val
                    85                  90                  95

Thr Phe Arg Leu Trp Asn Leu Asp Val Asn His Thr Asp Ile Tyr Phe
                100                 105                 110

Cys Lys Ile Glu Val Met Tyr Pro Pro Tyr Leu Asp Asn Glu Lys
            115                 120                 125

Ser Asn Gly Thr Ile Ile His Ile Lys Glu Lys His Leu Cys His Ala
130                 135                 140

Gln Thr Ser Pro Lys Leu Phe Trp Pro Leu Val Val Val Ala Gly Val
145                 150                 155                 160

Leu Leu Cys Tyr Gly Leu Leu Tyr Thr Val Thr Leu Cys Ile Ile Trp
                165                 170                 175

Thr Asn Ser Arg Arg Asn Arg Leu Leu Gln Ser Asp Tyr Met Asn Met
            180                 185                 190

Thr Pro Arg Arg Leu Gly Pro Thr Arg Lys His Tyr Gln Pro Tyr Ala
            195                 200                 205

Pro Ala Arg Asp Phe Ala Ala Tyr Arg Pro
            210                 215
```

<210> SEQ ID NO 7
<211> LENGTH: 220
<212> TYPE: PRT
<213> ORGANISM: Homo sapiens

<400> SEQUENCE: 7

```
Met Leu Arg Leu Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
            20                  25                  30

Asp Asn Ala Tyr Asn Leu Ser Cys Lys Tyr Ser Tyr Asn Leu Phe Ser
            35                  40                  45

Arg Glu Phe Arg Ala Ser Leu His Lys Gly Leu Asp Ser Ala Val Glu
    50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
                100                 105                 110

Lys Ile Glu Val Met Tyr Pro Pro Tyr Leu Asp Asn Glu Lys Ser
            115                 120                 125
```

```
Asn Gly Thr Ile Ile His Val Lys Gly Lys His Leu Cys Pro Ser Pro
        130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Tyr Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
    210                 215                 220

<210> SEQ ID NO 8
<211> LENGTH: 221
<212> TYPE: PRT
<213> ORGANISM: Gallus gallus

<400> SEQUENCE: 8

Met Leu Gly Ile Leu Val Val Leu Cys Leu Ile Pro Ala Ala Asp Val
1               5                   10                  15

Thr Glu Asn Lys Ile Leu Val Ala Gln Arg Pro Leu Leu Ile Val Ala
            20                  25                  30

Asn Arg Thr Ala Thr Leu Val Cys Asn Tyr Thr Tyr Asn Gly Thr Gly
        35                  40                  45

Lys Glu Phe Arg Ala Ser Leu His Lys Gly Thr Asp Ser Ala Val Glu
    50                  55                  60

Val Cys Phe Ile Ser Trp Asn Met Thr Lys Ile Asn Ser Asn Ser Asn
65                  70                  75                  80

Lys Glu Phe Asn Cys Arg Gly Ile His Asp Lys Asp Lys Val Ile Phe
                85                  90                  95

Asn Leu Trp Asn Met Ser Ala Ser Gln Thr Asp Ile Tyr Phe Cys Lys
            100                 105                 110

Ile Glu Ala Met Tyr Pro Pro Pro Tyr Val Tyr Asn Glu Lys Ser Asn
        115                 120                 125

Gly Thr Val Ile His Tyr Arg Glu Thr Pro Ile Gln Thr Gln Glu Pro
    130                 135                 140

Glu Ser Ala Thr Ser Tyr Trp Val Met Tyr Ala Val Thr Gly Leu Leu
145                 150                 155                 160

Gly Phe Tyr Ser Met Leu Ile Thr Ala Val Phe Ile Ile Tyr Arg Gln
                165                 170                 175

Lys Ser Lys Arg Asn Arg Tyr Arg Gln Ser Asp Tyr Met Asn Met Thr
            180                 185                 190

Pro Arg His Pro Pro His Gln Lys Asn Lys Gly Tyr Pro Ser Tyr Ala
        195                 200                 205

Pro Thr Arg Asp Tyr Thr Ala Tyr Arg Ser Trp Gln Pro
    210                 215                 220

<210> SEQ ID NO 9
<211> LENGTH: 1152
<212> TYPE: DNA
<213> ORGANISM: Artificial Sequence
<220> FEATURE:
<223> OTHER INFORMATION: Description of Artificial Sequence: CTLA4Ig

<400> SEQUENCE: 9
atgggtgtac tgctcacaca gaggacgctg ctcagtctgg tccttgcact cctgtttcca    60
```

-continued

```
agcatggcga gcatggcaat gcacgtggcc cagcctgctg tggtactggc cagcagccga      120
ggcatcgcta gctttgtgtg tgagtatgca tctccaggca aagccactga ggtccgggtg      180
acagtgcttc ggcaggctga cagccaggtg actgaagtct gtgcggcaac ctacatgatg      240
gggaatgagt tgaccttcct agatgattcc atctgcacgg gcacctccag tggaaatcaa      300
gtgaacctca ctatccaagg actgagggca atggacacgg gactctacat ctgcaaggtg      360
gagctcatgt acccaccgcc atactacctg gcataggca acggaaccca gatttatgta       420
attgatccag aaccgtgccc agattctgat caggagccca atcttctga caaaactcac       480 acatccccac cgtccccagc acctgaactc ctgggtggat cgtcagtctt cctcttcccc      540
ccaaaaccca aggacaccct catgatctcc cggacccctg aggtcacatg cgtggtggtg      600
gacgtgagcc acgaagaccc tgaggtcaag ttcaactggt acgtggacgg cgtggaggtg      660
cataatgcca agacaaagcc gcgggaggag cagtacaaca gcacgtaccg ggtggtcagc      720
gtcctcaccg tcctgcacca ggactggctg aatggcaagg agtacaagtg caaggtctcc      780
aacaaagccc tcccagcccc catcgagaaa accatctcca agccaaagg gcagccccga       840 gaaccacagg tgtacaccct gcccccatcc cgggatgagc tgaccaagaa ccaggtcagc      900
ctgacctgcc tggtcaaagg cttctatccc agcgacatcg ccgtggagtg ggagagcaat      960
gggcagccgg agaacaacta caagaccacg cctcccgtgc tggactccga cggctccttc     1020
ttcctctaca gcaagctcac cgtggacaag agcaggtggc agcagggaa cgtcttctca      1080 tgctccgtga tgcatgaggc tctgcacaac cactacacgc agaagagcct ctccctgtct     1140
ccgggtaaat ga                                                        1152
```

<210> SEQ ID NO 10
<211> LENGTH: 383
<212> TYPE: PRT
<213> ORGANISM: Artificial Sequence
<220> FEATURE:
<223> OTHER INFORMATION: Description of Artificial Sequence: CTLA4Ig

<400> SEQUENCE: 10

```
Met Gly Val Leu Leu Thr Gln Arg Thr Leu Leu Ser Leu Val Leu Ala
1               5                   10                  15

Leu Leu Phe Pro Ser Met Ala Ser Met Ala Met His Val Ala Gln Pro
            20                  25                  30

Ala Val Val Leu Ala Ser Ser Arg Gly Ile Ala Ser Phe Val Cys Glu
        35                  40                  45

Tyr Ala Ser Pro Gly Lys Ala Thr Glu Val Arg Val Thr Val Leu Arg
    50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                85                  90                  95

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
        115                 120                 125

Tyr Leu Gly Ile Gly Asn Gly Thr Gln Ile Tyr Val Ile Asp Pro Glu
    130                 135                 140

Pro Cys Pro Asp Ser Asp Gln Glu Pro Lys Ser Ser Asp Lys Thr His
145                 150                 155                 160
```

```
Thr Ser Pro Pro Ser Pro Ala Pro Glu Leu Leu Gly Ser Ser Val
            165                 170                 175

Phe Leu Phe Pro Pro Lys Pro Lys Asp Thr Leu Met Ile Ser Arg Thr
            180                 185                 190

Pro Glu Val Thr Cys Val Val Asp Val Ser His Glu Asp Pro Glu
            195                 200                 205

Val Lys Phe Asn Trp Tyr Val Asp Gly Val Glu Val His Asn Ala Lys
210                 215                 220

Thr Lys Pro Arg Glu Glu Gln Tyr Asn Ser Thr Tyr Arg Val Val Ser
225                 230                 235                 240

Val Leu Thr Val Leu His Gln Asp Trp Leu Asn Gly Lys Glu Tyr Lys
            245                 250                 255

Cys Lys Val Ser Asn Lys Ala Leu Pro Ala Pro Ile Glu Lys Thr Ile
            260                 265                 270

Ser Lys Ala Lys Gly Gln Pro Arg Glu Pro Gln Val Tyr Thr Leu Pro
            275                 280                 285

Pro Ser Arg Asp Glu Leu Thr Lys Asn Gln Val Ser Leu Thr Cys Leu
            290                 295                 300

Val Lys Gly Phe Tyr Pro Ser Asp Ile Ala Val Glu Trp Glu Ser Asn
305                 310                 315                 320

Gly Gln Pro Glu Asn Asn Tyr Lys Thr Thr Pro Pro Val Leu Asp Ser
            325                 330                 335

Asp Gly Ser Phe Phe Leu Tyr Ser Lys Leu Thr Val Asp Lys Ser Arg
            340                 345                 350

Trp Gln Gln Gly Asn Val Phe Ser Cys Ser Val Met His Glu Ala Leu
            355                 360                 365

His Asn His Tyr Thr Gln Lys Ser Leu Ser Leu Ser Pro Gly Lys
            370                 375                 380

<210> SEQ ID NO 11
<211> LENGTH: 1152
<212> TYPE: DNA
<213> ORGANISM: Artificial Sequence
<220> FEATURE:
<223> OTHER INFORMATION: Description of Artificial Sequence: L104EIg

<400> SEQUENCE: 11
atgggtgtac tgctcacaca gaggacgctg ctcagtctgg tccttgcact cctgtttcca      60
agcatggcga gcatggcaat gcacgtggcc cagcctgctg tggtactggc cagcagccga     120
ggcatcgcta gctttgtgtg tgagtatgca tctccaggca aagccactga ggtccgggtg     180
acagtgcttc ggcaggctga cagccaggtg actgaagtct gtgcggcaac ctacatgatg     240
gggaatgagt tgaccttcct agatgattcc atctgcacgg gcacctccag tggaaatcaa     300
gtgaacctca ctatccaagg actgagggcc atggacacgg actctacat ctgcaaggtg     360 gagctcatgt acccaccgcc atactacgag ggcataggca cggaaccca gatttatgta     420 attgatccag aaccgtgccc agattctgat caggagccca atcttctga caaaactcac     480 acatccccac cgtccccagc acctgaactc ctggggggat cgtcagtctt cctcttcccc     540
ccaaaaccca aggacaccct catgatctcc cggacccctg aggtcacatg cgtggtggtg     600
gacgtgagcc acgaagaccc tgaggtcaag ttcaactggt acgtggacgg cgtggaggtg     660
cataatgcca agacaaagcc gcgggaggag cagtacaaca gcacgtaccg tgtggtcagc     720
gtcctcaccg tcctgcacca ggactggctg aatggcaagg agtacaagtg caaggtctcc     780
aacaaagccc tcccagcccc catcgagaaa accatctcca agccaaagg gcagccccga     840
```

-continued

```
gaaccacagg tgtacaccct gcccccatcc cgggatgagc tgaccaagaa ccaggtcagc      900
ctgacctgcc tggtcaaagg cttctatccc agcgacatcg ccgtggagtg ggagagcaat      960
gggcagccgg agaacaacta caagaccacg cctcccgtgc tggactccga cggctccttc     1020
ttcctctaca gcaagctcac cgtggacaag agcaggtggc agcaggggaa cgtcttctca     1080
tgctccgtga tgcatgaggc tctgcacaac cactacacgc agaagagcct ctccctgtct     1140
ccgggtaaat ga                                                         1152
```

<210> SEQ ID NO 12
<211> LENGTH: 383
<212> TYPE: PRT
<213> ORGANISM: Artificial Sequence
<220> FEATURE:
<223> OTHER INFORMATION: Description of Artificial Sequence: L104EIg

<400> SEQUENCE: 12

```
Met Gly Val Leu Leu Thr Gln Arg Thr Leu Leu Ser Leu Val Leu Ala
1               5                   10                  15

Leu Leu Phe Pro Ser Met Ala Ser Met Ala Met His Val Ala Gln Pro
            20                  25                  30

Ala Val Val Leu Ala Ser Ser Arg Gly Ile Ala Ser Phe Val Cys Glu
        35                  40                  45

Tyr Ala Ser Pro Gly Lys Ala Thr Glu Val Arg Val Thr Val Leu Arg
    50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                85                  90                  95

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
        115                 120                 125

Tyr Glu Gly Ile Gly Asn Gly Thr Gln Ile Tyr Val Ile Asp Pro Glu
    130                 135                 140

Pro Cys Pro Asp Ser Asp Gln Glu Pro Lys Ser Ser Asp Lys Thr His
145                 150                 155                 160

Thr Ser Pro Pro Ser Pro Ala Pro Glu Leu Leu Gly Gly Ser Ser Val
                165                 170                 175

Phe Leu Phe Pro Pro Lys Pro Lys Asp Thr Leu Met Ile Ser Arg Thr
            180                 185                 190

Pro Glu Val Thr Cys Val Val Val Asp Val Ser His Glu Asp Pro Glu
        195                 200                 205

Val Lys Phe Asn Trp Tyr Val Asp Gly Val Glu Val His Asn Ala Lys
    210                 215                 220

Thr Lys Pro Arg Glu Glu Gln Tyr Asn Ser Thr Tyr Arg Val Val Ser
225                 230                 235                 240

Val Leu Thr Val Leu His Gln Asp Trp Leu Asn Gly Lys Glu Tyr Lys
                245                 250                 255

Cys Lys Val Ser Asn Lys Ala Leu Pro Ala Pro Ile Glu Lys Thr Ile
            260                 265                 270

Ser Lys Ala Lys Gly Gln Pro Arg Glu Pro Gln Val Tyr Thr Leu Pro
        275                 280                 285

Pro Ser Arg Asp Glu Leu Thr Lys Asn Gln Val Ser Leu Thr Cys Leu
    290                 295                 300
```

| | | | | | | | | | | | | | | |
|---|---|---|---|---|---|---|---|---|---|---|---|---|---|---|
|Val|Lys|Gly|Phe|Tyr|Pro|Ser|Asp|Ile|Ala|Val|Glu|Trp|Glu|Ser|Asn|
|305| | | |310| | | |315| | | |320| | |

Gly Gln Pro Glu Asn Asn Tyr Lys Thr Thr Pro Pro Val Leu Asp Ser
                325                    330                    335

Asp Gly Ser Phe Phe Leu Tyr Ser Lys Leu Thr Val Asp Lys Ser Arg
                340                    345                    350

Trp Gln Gln Gly Asn Val Phe Ser Cys Ser Val Met His Glu Ala Leu
        355                    360                    365

His Asn His Tyr Thr Gln Lys Ser Leu Ser Leu Ser Pro Gly Lys
   370                      375                    380

<210> SEQ ID NO 13
<211> LENGTH: 1152
<212> TYPE: DNA
<213> ORGANISM: Artificial Sequence
<220> FEATURE:
<223> OTHER INFORMATION: Description of Artificial Sequence: L104EA29YIg

<400> SEQUENCE: 13

```
atgggtgtac tgctcacaca gaggacgctg ctcagtctgg tccttgcact cctgtttcca      60
agcatggcga gcatggcaat gcacgtggcc cagcctgctg tggtactggc cagcagccga     120
ggcatcgcta gctttgtgtg tgagtatgca tctccaggca aatatactga ggtccgggtg     180
acagtgcttc ggcaggctga cagccaggtg actgaagtct gtgcggcaac ctacatgatg     240
gggaatgagt tgaccttcct agatgattcc atctgcacgg gcacctccag tggaaatcaa     300
gtgaacctca ctatccaagg actgagggcc atggacacgg actctacat ctgcaaggtg     360
gagctcatgt acccaccgcc atactacgag ggcataggca acggaaccca gatttatgta     420
attgatccag aaccgtgccc agattctgat caggagccca atcttctga caaaactcac     480
acatccccac cgtccccagc acctgaactc ctggggggat cgtcagtctt cctcttcccc     540
ccaaaaccca aggacaccct catgatctcc cggacccctg aggtcacatg cgtggtggtg     600
gacgtgagcc acgaagaccc tgaggtcaag ttcaactggt acgtggacgg cgtggaggtg     660
cataatgcca agacaaagcc gcgggaggag cagtacaaca gcacgtaccg tgtggtcagc     720
gtcctcaccg tcctgcacca ggactggctg aatggcaagg agtacaagtg caaggtctcc     780
aacaaagccc tcccagcccc catcgagaaa accatctcca agccaaagg gcagccccga     840
gaaccacagg tgtacaccct gcccccatcc cgggatgagc tgaccaagaa ccaggtcagc     900
ctgacctgcc tggtcaaagg cttctatccc agcgacatcg ccgtggagtg ggagagcaat     960
gggcagccgg agaacaacta caagaccacg cctcccgtgc tggactccga cggctccttc    1020
ttcctctaca gcaagctcac cgtggacaag agcaggtggc agcaggggaa cgtcttctca    1080
tgctccgtga tgcatgaggc tctgcacaac cactacacgc agaagagcct ctccctgtct    1140
ccgggtaaat ga                                                        1152
```

<210> SEQ ID NO 14
<211> LENGTH: 383
<212> TYPE: PRT
<213> ORGANISM: Artificial Sequence
<220> FEATURE:
<223> OTHER INFORMATION: Description of Artificial Sequence: L104EA29YIg

<400> SEQUENCE: 14

Met Gly Val Leu Leu Thr Gln Arg Thr Leu Leu Ser Leu Val Leu Ala
1               5                    10                   15

```
Leu Leu Phe Pro Ser Met Ala Ser Met Ala Met His Val Ala Gln Pro
            20                  25                  30
Ala Val Val Leu Ala Ser Ser Arg Gly Ile Ala Ser Phe Val Cys Glu
        35                  40                  45
Tyr Ala Ser Pro Gly Lys Tyr Thr Glu Val Arg Val Thr Val Leu Arg
    50                  55                  60
Gln Ala Asp Ser Gln Val Thr Glu Val Cys Ala Ala Thr Tyr Met Met
65                  70                  75                  80
Gly Asn Glu Leu Thr Phe Leu Asp Asp Ser Ile Cys Thr Gly Thr Ser
                85                  90                  95
Ser Gly Asn Gln Val Asn Leu Thr Ile Gln Gly Leu Arg Ala Met Asp
            100                 105                 110
Thr Gly Leu Tyr Ile Cys Lys Val Glu Leu Met Tyr Pro Pro Pro Tyr
        115                 120                 125
Tyr Glu Gly Ile Gly Asn Gly Thr Gln Ile Tyr Val Ile Asp Pro Glu
    130                 135                 140
Pro Cys Pro Asp Ser Asp Gln Glu Pro Lys Ser Ser Asp Lys Thr His
145                 150                 155                 160
Thr Ser Pro Pro Ser Pro Ala Pro Glu Leu Leu Gly Gly Ser Ser Val
                165                 170                 175
Phe Leu Phe Pro Pro Lys Pro Lys Asp Thr Leu Met Ile Ser Arg Thr
            180                 185                 190
Pro Glu Val Thr Cys Val Val Val Asp Val Ser His Glu Asp Pro Glu
        195                 200                 205
Val Lys Phe Asn Trp Tyr Val Asp Gly Val Glu Val His Asn Ala Lys
    210                 215                 220
Thr Lys Pro Arg Glu Glu Gln Tyr Asn Ser Thr Tyr Arg Val Val Ser
225                 230                 235                 240
Val Leu Thr Val Leu His Gln Asp Trp Leu Asn Gly Lys Glu Tyr Lys
                245                 250                 255
Cys Lys Val Ser Asn Lys Ala Leu Pro Ala Pro Ile Glu Lys Thr Ile
            260                 265                 270
Ser Lys Ala Lys Gly Gln Pro Arg Glu Pro Gln Val Tyr Thr Leu Pro
        275                 280                 285
Pro Ser Arg Asp Glu Leu Thr Lys Asn Gln Val Ser Leu Thr Cys Leu
    290                 295                 300
Val Lys Gly Phe Tyr Pro Ser Asp Ile Ala Val Glu Trp Glu Ser Asn
305                 310                 315                 320
Gly Gln Pro Glu Asn Asn Tyr Lys Thr Thr Pro Pro Val Leu Asp Ser
                325                 330                 335
Asp Gly Ser Phe Phe Leu Tyr Ser Lys Leu Thr Val Asp Lys Ser Arg
            340                 345                 350
Trp Gln Gln Gly Asn Val Phe Ser Cys Ser Val Met His Glu Ala Leu
        355                 360                 365
His Asn His Tyr Thr Gln Lys Ser Leu Ser Leu Ser Pro Gly Lys
    370                 375                 380

<210> SEQ ID NO 15
<211> LENGTH: 1152
<212> TYPE: DNA
<213> ORGANISM: Artificial Sequence
<220> FEATURE:
<223> OTHER INFORMATION: Description of Artificial Sequence: L104EA29LIg

<400> SEQUENCE: 15
```

-continued

```
atgggtgtac tgctcacaca gaggacgctg ctcagtctgg tccttgcact cctgttccca    60
agcatggcga gcatggcaat gcacgtggcc cagcctgctg tggtactggc cagcagccga   120
ggcatcgcta gctttgtgtg tgagtatgca tctccaggca aattgactga ggtccgggtg   180
acagtgcttc ggcaggctga cagccaggtg actgaagtct gtgcggcaac ctacatgatg   240
gggaatgagt tgaccttcct agatgattcc atctgcacgg gcacctccag tggaaatcaa   300
gtgaacctca ctatccaagg actgagggcc atggacacgg gactctacat ctgcaaggtg   360
gagctcatgt acccaccgcc atactacgag ggcataggca acggaaccca gatttatgta   420
attgatccag aaccgtgccc agattctgat caggagccca atcttctga caaaactcac   480
acatccccac cgtccccagc acctgaactc ctgggggat cgtcagtctt cctcttcccc    540
ccaaaaccca aggacaccct catgatctcc cggacccctg aggtcacatg cgtggtggtg   600
gacgtgagcc acgaagaccc tgaggtcaag ttcaactggt acgtggacgg cgtggaggtg   660
cataatgcca agacaaagcc gcgggaggag cagtacaaca gcacgtaccg tgtggtcagc   720
gtcctcaccg tcctgcacca ggactggctg aatggcaagg agtacaagtg caaggtctcc   780
aacaaagccc tcccagcccc catcgagaaa accatctcca aagccaaagg cagccccga   840
gaaccacagg tgtacaccct gcccccatcc cgggatgagc tgaccaagaa ccaggtcagc   900
ctgacctgcc tggtcaaagg cttctatccc agcgacatcg ccgtggagtg ggagagcaat   960
gggcagccgg agaacaacta caagaccacg cctcccgtgc tggactccga cggctccttc  1020
ttcctctaca gcaagctcac cgtggacaag agcaggtggc agcaggggaa cgtcttctca  1080
tgctccgtga tgcatgaggc tctgcacaac cactacacgc agaagagcct ctccctgtct  1140
ccgggtaaat ga                                                      1152
```

<210> SEQ ID NO 16
<211> LENGTH: 383
<212> TYPE: PRT
<213> ORGANISM: Artificial Sequence
<220> FEATURE:
<223> OTHER INFORMATION: Description of Artificial Sequence: L104EA29LIg

<400> SEQUENCE: 16

```
Met Gly Val Leu Leu Thr Gln Arg Thr Leu Leu Ser Leu Val Leu Ala
1               5                  10                  15

Leu Leu Phe Pro Ser Met Ala Ser Met Ala Met His Val Ala Gln Pro
            20                  25                  30

Ala Val Val Leu Ala Ser Ser Arg Gly Ile Ala Ser Phe Val Cys Glu
        35                  40                  45

Tyr Ala Ser Pro Gly Lys Leu Thr Glu Val Arg Val Thr Val Leu Arg
    50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                85                  90                  95

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
        115                 120                 125

Tyr Glu Gly Ile Gly Asn Gly Thr Gln Ile Tyr Val Ile Asp Pro Glu
    130                 135                 140

Pro Cys Pro Asp Ser Asp Gln Glu Pro Lys Ser Ser Asp Lys Thr His
145                 150                 155                 160
```

```
Thr Ser Pro Pro Ser Pro Ala Pro Glu Leu Leu Gly Gly Ser Ser Val
            165                 170                 175

Phe Leu Phe Pro Pro Lys Pro Lys Asp Thr Leu Met Ile Ser Arg Thr
        180                 185                 190

Pro Glu Val Thr Cys Val Val Val Asp Val Ser His Glu Asp Pro Glu
    195                 200                 205

Val Lys Phe Asn Trp Tyr Val Asp Gly Val Glu Val His Asn Ala Lys
    210                 215                 220

Thr Lys Pro Arg Glu Glu Gln Tyr Asn Ser Thr Tyr Arg Val Val Ser
225                 230                 235                 240

Val Leu Thr Val Leu His Gln Asp Trp Leu Asn Gly Lys Glu Tyr Lys
            245                 250                 255

Cys Lys Val Ser Asn Lys Ala Leu Pro Ala Pro Ile Glu Lys Thr Ile
            260                 265                 270

Ser Lys Ala Lys Gly Gln Pro Arg Glu Pro Gln Val Tyr Thr Leu Pro
        275                 280                 285

Pro Ser Arg Asp Glu Leu Thr Lys Asn Gln Val Ser Leu Thr Cys Leu
    290                 295                 300

Val Lys Gly Phe Tyr Pro Ser Asp Ile Ala Val Glu Trp Glu Ser Asn
305                 310                 315                 320

Gly Gln Pro Glu Asn Asn Tyr Lys Thr Thr Pro Pro Val Leu Asp Ser
            325                 330                 335

Asp Gly Ser Phe Phe Leu Tyr Ser Lys Leu Thr Val Asp Lys Ser Arg
            340                 345                 350

Trp Gln Gln Gly Asn Val Phe Ser Cys Ser Val Met His Glu Ala Leu
        355                 360                 365

His Asn His Tyr Thr Gln Lys Ser Leu Ser Leu Ser Pro Gly Lys
    370                 375                 380

<210> SEQ ID NO 17
<211> LENGTH: 1152
<212> TYPE: DNA
<213> ORGANISM: Artificial Sequence
<220> FEATURE:
<223> OTHER INFORMATION: Description of Artificial Sequence: L104EA29TIg

<400> SEQUENCE: 17
atgggtgtac tgctcacaca gaggacgctg ctcagtctgg tccttgcact cctgtttcca      60
agcatggcga gcatggcaat gcacgtggcc cagcctgctg tggtactggc cagcagccga     120
ggcatcgcta gctttgtgtg tgagtatgca tctccaggca aaactactga ggtccgggtg     180
acagtgcttc ggcaggctga cagccaggtg actgaagtct gtgcggcaac ctacatgatg     240
gggaatgagt tgaccttcct agatgattcc atctgcacgg gcacctccag tggaaatcaa     300
gtgaacctca ctatccaagg actgagggcc atggacacgg gactctacat ctgcaaggtg     360
gagctcatgt acccaccgcc atactacgag ggcataggca cggaaccca gatttatgta     420 attgatccag aaccgtgccc agattctgat caggagccca atcttctga caaaactcac     480 acatccccac cgtcccagc acctgaactc ctggggggat cgtcagtctt cctcttcccc     540
ccaaaaccca aggacaccct catgatctcc cggaccctg aggtcacatg cgtggtggtg     600
gacgtgagcc acgaagaccc tgaggtcaag ttcaactggt acgtggacgg cgtggaggtg     660
cataatgcca agacaaagcc gcgggaggag cagtacaaca gcacgtaccg tgtggtcagc     720
gtcctcaccg tcctgcacca ggactggctg aatggcaagg agtacaagtg caaggtctcc     780
```

-continued

```
aacaaagccc tcccagcccc catcgagaaa accatctcca aagccaaagg gcagccccga    840
gaaccacagg tgtacaccct gcccccatcc cgggatgagc tgaccaagaa ccaggtcagc    900
ctgacctgcc tggtcaaagg cttctatccc agcgacatcg ccgtggagtg ggagagcaat    960
gggcagccgg agaacaacta caagaccacg cctcccgtgc tggactccga cggctccttc   1020
ttcctctaca gcaagctcac cgtggacaag agcaggtggc agcagggaa cgtcttctca    1080 tgctccgtga tgcatgaggc tctgcacaac cactacacgc agaagagcct ctccctgtct   1140
ccgggtaaat ga                                                      1152
```

<210> SEQ ID NO 18
<211> LENGTH: 383
<212> TYPE: PRT
<213> ORGANISM: Artificial Sequence
<220> FEATURE:
<223> OTHER INFORMATION: Description of Artificial Sequence: L104EA29TIg

<400> SEQUENCE: 18

```
Met Gly Val Leu Leu Thr Gln Arg Thr Leu Leu Ser Leu Val Leu Ala
1               5                   10                  15

Leu Leu Phe Pro Ser Met Ala Ser Met Ala Met His Val Ala Gln Pro
            20                  25                  30

Ala Val Val Leu Ala Ser Ser Arg Gly Ile Ala Ser Phe Val Cys Glu
        35                  40                  45

Tyr Ala Ser Pro Gly Lys Thr Thr Glu Val Arg Val Thr Val Leu Arg
    50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                85                  90                  95

Ser Gly Asn Gln Val Asn Leu Thr Ile Gln Gly Leu Arg Ala Met Asp
            100                 105                 110

Thr Gly Leu Tyr Ile Cys Lys Val Glu Leu Met Tyr Pro Pro Pro Tyr
        115                 120                 125

Tyr Glu Gly Ile Gly Asn Gly Thr Gln Ile Tyr Val Ile Asp Pro Glu
    130                 135                 140

Pro Cys Pro Asp Ser Asp Gln Glu Pro Lys Ser Ser Asp Lys Thr His
145                 150                 155                 160

Thr Ser Pro Pro Ser Pro Ala Pro Glu Leu Leu Gly Gly Ser Ser Val
                165                 170                 175

Phe Leu Phe Pro Pro Lys Pro Lys Asp Thr Leu Met Ile Ser Arg Thr
            180                 185                 190

Pro Glu Val Thr Cys Val Val Val Asp Val Ser His Glu Asp Pro Glu
        195                 200                 205

Val Lys Phe Asn Trp Tyr Val Asp Gly Val Glu Val His Asn Ala Lys
    210                 215                 220

Thr Lys Pro Arg Glu Glu Gln Tyr Asn Ser Thr Tyr Arg Val Val Ser
225                 230                 235                 240

Val Leu Thr Val Leu His Gln Asp Trp Leu Asn Gly Lys Glu Tyr Lys
                245                 250                 255

Cys Lys Val Ser Asn Lys Ala Leu Pro Ala Pro Ile Glu Lys Thr Ile
            260                 265                 270

Ser Lys Ala Lys Gly Gln Pro Arg Glu Pro Gln Val Tyr Thr Leu Pro
        275                 280                 285

Pro Ser Arg Asp Glu Leu Thr Lys Asn Gln Val Ser Leu Thr Cys Leu
```

```
                    290             295             300
Val Lys Gly Phe Tyr Pro Ser Asp Ile Ala Val Glu Trp Glu Ser Asn
305                 310                 315                 320

Gly Gln Pro Glu Asn Asn Tyr Lys Thr Thr Pro Pro Val Leu Asp Ser
                325                 330                 335

Asp Gly Ser Phe Phe Leu Tyr Ser Lys Leu Thr Val Asp Lys Ser Arg
            340                 345                 350

Trp Gln Gln Gly Asn Val Phe Ser Cys Ser Val Met His Glu Ala Leu
                355                 360                 365

His Asn His Tyr Thr Gln Lys Ser Leu Ser Leu Ser Pro Gly Lys
    370                 375                 380

<210> SEQ ID NO 19
<211> LENGTH: 1152
<212> TYPE: DNA
<213> ORGANISM: Artificial Sequence
<220> FEATURE:
<223> OTHER INFORMATION: Description of Artificial Sequence: L104EA29WIg

<400> SEQUENCE: 19
atgggtgtac tgctcacaca gaggacgctg ctcagtctgg tccttgcact cctgtttcca      60
agcatggcga gcatggcaat gcacgtggcc cagcctgctg tggtactggc cagcagccga     120
ggcatcgcta gctttgtgtg tgagtatgca tctccaggca aatggactga ggtccgggtg     180
acagtgcttc ggcaggctga cagccaggtg actgaagtct gtgcggcaac ctacatgatg     240
gggaatgagt tgaccttcct agatgattcc atctgcacgg gcacctccag tggaaatcaa     300
gtgaacctca ctatccaagg actgagggcc atggacacgg gactctacat ctgcaaggtg     360
gagctcatgt acccaccgcc atactacgag ggcataggca cggaaccca gatttatgta      420 attgatccag aaccgtgccc agattctgat caggagccca atcttctga caaaactcac      480 acatccccac cgtccccagc acctgaactc ctggggggat cgtcagtctt cctcttcccc     540
ccaaaaccca aggacaccct catgatctcc cggacccctg aggtcacatg cgtggtggtg     600
gacgtgagcc acgaagaccc tgaggtcaag ttcaactggt acgtggacgg cgtggaggtg     660
cataatgcca agacaaagcc gcgggaggag cagtacaaca gcacgtaccg tgtggtcagc     720
gtcctcaccg tcctgcacca ggactggctg aatggcaagg agtacaagtg caaggtctcc     780
aacaaagccc tcccagcccc catcgagaaa accatctcca aagccaaagg gcagccccga     840
gaaccacagg tgtacaccct gcccccatcc cgggatgagc tgaccaagaa ccaggtcagc     900
ctgacctgcc tggtcaaagg cttctatccc agcgacatcg ccgtggagtg ggagagcaat     960
gggcagccgg agaacaacta caagaccacg cctcccgtgc tggactccga cggctccttc    1020
ttcctctaca gcaagctcac cgtggacaag agcaggtggc agcaggggaa cgtcttctca    1080
tgctccgtga tgcatgaggc tctgcacaac cactacacgc agaagagcct ctccctgtct    1140
ccgggtaaat ga                                                         1152

<210> SEQ ID NO 20
<211> LENGTH: 383
<212> TYPE: PRT
<213> ORGANISM: Artificial Sequence
<220> FEATURE:
<223> OTHER INFORMATION: Description of Artificial Sequence: L104EA29WIg

<400> SEQUENCE: 20

Met Gly Val Leu Leu Thr Gln Arg Thr Leu Leu Ser Leu Val Leu Ala
1               5                   10                  15
```

```
Leu Leu Phe Pro Ser Met Ala Ser Met Ala Met His Val Ala Gln Pro
             20                  25                  30

Ala Val Val Leu Ala Ser Ser Arg Gly Ile Ala Ser Phe Val Cys Glu
         35                  40                  45

Tyr Ala Ser Pro Gly Lys Trp Thr Glu Val Arg Val Thr Val Leu Arg
     50                  55                  60

Gln Ala Asp Ser Gln Val Thr Glu Val Cys Ala Ala Thr Tyr Met Met
65                  70                  75                  80

Gly Asn Glu Leu Thr Phe Leu Asp Asp Ser Ile Cys Thr Gly Thr Ser
                 85                  90                  95

Ser Gly Asn Gln Val Asn Leu Thr Ile Gln Gly Leu Arg Ala Met Asp
             100                 105                 110

Thr Gly Leu Tyr Ile Cys Lys Val Glu Leu Met Tyr Pro Pro Pro Tyr
         115                 120                 125

Tyr Glu Gly Ile Gly Asn Gly Thr Gln Ile Tyr Val Ile Asp Pro Glu
    130                 135                 140

Pro Cys Pro Asp Ser Asp Gln Glu Pro Lys Ser Ser Asp Lys Thr His
145                 150                 155                 160

Thr Ser Pro Pro Ser Pro Ala Pro Glu Leu Leu Gly Gly Ser Ser Val
                165                 170                 175

Phe Leu Phe Pro Pro Lys Pro Lys Asp Thr Leu Met Ile Ser Arg Thr
            180                 185                 190

Pro Glu Val Thr Cys Val Val Val Asp Val Ser His Glu Asp Pro Glu
        195                 200                 205

Val Lys Phe Asn Trp Tyr Val Asp Gly Val Glu Val His Asn Ala Lys
    210                 215                 220

Thr Lys Pro Arg Glu Glu Gln Tyr Asn Ser Thr Tyr Arg Val Val Ser
225                 230                 235                 240

Val Leu Thr Val Leu His Gln Asp Trp Leu Asn Gly Lys Glu Tyr Lys
                245                 250                 255

Cys Lys Val Ser Asn Lys Ala Leu Pro Ala Pro Ile Glu Lys Thr Ile
            260                 265                 270

Ser Lys Ala Lys Gly Gln Pro Arg Glu Pro Gln Val Tyr Thr Leu Pro
        275                 280                 285

Pro Ser Arg Asp Glu Leu Thr Lys Asn Gln Val Ser Leu Thr Cys Leu
    290                 295                 300

Val Lys Gly Phe Tyr Pro Ser Asp Ile Ala Val Glu Trp Glu Ser Asn
305                 310                 315                 320

Gly Gln Pro Glu Asn Asn Tyr Lys Thr Thr Pro Pro Val Leu Asp Ser
                325                 330                 335

Asp Gly Ser Phe Phe Leu Tyr Ser Lys Leu Thr Val Asp Lys Ser Arg
            340                 345                 350

Trp Gln Gln Gly Asn Val Phe Ser Cys Ser Val Met His Glu Ala Leu
        355                 360                 365

His Asn His Tyr Thr Gln Lys Ser Leu Ser Leu Ser Pro Gly Lys
    370                 375                 380

<210> SEQ ID NO 21
<211> LENGTH: 65
<212> TYPE: DNA
<213> ORGANISM: Homo sapiens

<400> SEQUENCE: 21
ctcagtctgg tccttgcact cctgtttcca agcatggcga gcatggcaat gcacgtggcc      60
``` cagcc                                                                65

<210> SEQ ID NO 22
<211> LENGTH: 33
<212> TYPE: DNA
<213> ORGANISM: Homo sapiens

<400> SEQUENCE: 22
tttgggctcc tgatcagaat ctgggcacgg ttg                                 33

<210> SEQ ID NO 23
<211> LENGTH: 72
<212> TYPE: DNA
<213> ORGANISM: Homo sapiens

<400> SEQUENCE: 23
ctagccactg aagcttcacc aatgggtgta ctgctcacac agaggacgct gctcagtctg    60
gtccttgcac tc                                                        72

<210> SEQ ID NO 24
<211> LENGTH: 33
<212> TYPE: DNA
<213> ORGANISM: Homo sapiens

<400> SEQUENCE: 24
gcaatgcacg tggcccagcc tgctgtggta gtg                                 33

<210> SEQ ID NO 25
<211> LENGTH: 45
<212> TYPE: DNA
<213> ORGANISM: Homo sapiens

<400> SEQUENCE: 25
tgatgtaaca tgtctagatc aattgatggg aataaaataa ggctg                    45

<210> SEQ ID NO 26
<211> LENGTH: 39
<212> TYPE: DNA
<213> ORGANISM: Artificial Sequence
<220> FEATURE:
<223> OTHER INFORMATION: Description of Artificial Sequence: Oncostatin
      M signal peptide forward primer

<400> SEQUENCE: 26
ctagccactg aagcttcacc atgggtgtac tgctcacac                           39

<210> SEQ ID NO 27
<211> LENGTH: 39
<212> TYPE: DNA
<213> ORGANISM: Artificial Sequence
<220> FEATURE:
<223> OTHER INFORMATION: Description of Artificial Sequence: Oncostatin
      M signal peptide reverse primer

<400> SEQUENCE: 27
tggcatgggc tcctgatcag gcttagaagg tccgggaaa                           39

<210> SEQ ID NO 28
<211> LENGTH: 39
<212> TYPE: DNA
<213> ORGANISM: Artificial Sequence
<220> FEATURE:
<223> OTHER INFORMATION: Description of Artificial Sequence: Oncostatin
      M signal peptide reverse primer

```
<400> SEQUENCE: 28
tttgggctcc tgatcaggaa aatgctcttg cttggttgt                               39

<210> SEQ ID NO 29
<211> LENGTH: 84
<212> TYPE: DNA
<213> ORGANISM: Artificial Sequence
<220> FEATURE:
<223> OTHER INFORMATION: Description of Artificial Sequence: Human
      IgCgamma1 forward primer

<400> SEQUENCE: 29
aagcaagagc attttcctga tcaggagccc aaatcttctg acaaaactca cacatcccca        60
ccgtccccag cacctgaact cctg                                              84

<210> SEQ ID NO 30
<211> LENGTH: 41
<212> TYPE: DNA
<213> ORGANISM: Artificial Sequence
<220> FEATURE:
<223> OTHER INFORMATION: Description of Artificial Sequence: Human
      IgCgamma1 reverse primer

<400> SEQUENCE: 30
cttcgaccag tctagaagca tcctcgtgcg accgcgagag c                            41

<210> SEQ ID NO 31
<211> LENGTH: 47
<212> TYPE: DNA
<213> ORGANISM: Artificial Sequence
<220> FEATURE:
<223> OTHER INFORMATION: Description of Artificial Sequence: CD5Ig
      forward primer

<400> SEQUENCE: 31
cattgcacag tcaagcttcc atgcccatgg gttctctggc caccttg                     47

<210> SEQ ID NO 32
<211> LENGTH: 39
<212> TYPE: DNA
<213> ORGANISM: Artificial Sequence
<220> FEATURE:
<223> OTHER INFORMATION: Description of Artificial Sequence: CD5Ig
      reverse primer

<400> SEQUENCE: 32
atccacagtg cagtgatcat ttggatcctg gcatgtgac                              39

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: CDM8
      forward primer

<400> SEQUENCE: 33
aatacgactc actatagg                                                     18

<210> SEQ ID NO 34
<211> LENGTH: 18
<212> TYPE: DNA
<213> ORGANISM: Artificial Sequence
<220> FEATURE:
<223> OTHER INFORMATION: Description of Artificial Sequence: CDM8
```

```
                    reverse primer

<400> SEQUENCE: 34
caccacactg tattaacc                                                18

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: CTLA4/CD28

<400> SEQUENCE: 35

Met Tyr Pro Pro Pro Tyr
1               5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: CTLA4Ig
      mutant fusion protein

<400> SEQUENCE: 36

Ala Tyr Pro Pro Pro Tyr
1               5

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: CTLA4Ig
      mutant fusion protein

<400> SEQUENCE: 37

Met Ala Pro Pro Pro Tyr
1               5

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: CTLA4Ig
      mutant fusion protein

<400> SEQUENCE: 38

Met Tyr Ala Pro Pro Tyr
1               5

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: CTLA4Ig
      mutant fusion protein

<400> SEQUENCE: 39

Met Tyr Pro Ala Pro Tyr
1               5

<210> SEQ ID NO 40
<211> LENGTH: 6
<212> TYPE: PRT
```

```
<213> ORGANISM: Artificial Sequence
<220> FEATURE:
<223> OTHER INFORMATION: Description of Artificial Sequence:
      CTLA4/CD28Ig mutant fusion protein

<400> SEQUENCE: 40

Met Tyr Pro Pro Ala Tyr
1               5

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence:
      CTLA4/CD28Ig mutant fusion protein

<400> SEQUENCE: 41

Met Tyr Pro Pro Pro Ala
1               5

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: CTLA4Ig
      mutant fusion protein

<400> SEQUENCE: 42

Ala Ala Pro Pro Pro Tyr
1               5

<210> SEQ ID NO 43
<211> LENGTH: 68
<212> TYPE: DNA
<213> ORGANISM: Artificial Sequence
<220> FEATURE:
<223> OTHER INFORMATION: k is either c, g or t
<220> FEATURE:
<221> NAME/KEY: misc_feature
<222> LOCATION: (28)..(29)
<223> OTHER INFORMATION: n is either a, c, g or t
<220> FEATURE:
<221> NAME/KEY: misc_feature
<222> LOCATION: (30)..(30)
<223> OTHER INFORMATION: k is either c, g or t
<220> FEATURE:
<221> NAME/KEY: misc_feature
<222> LOCATION: (31)..(32)
<223> OTHER INFORMATION: n is either a, c, g or t
<220> FEATURE:
<221> NAME/KEY: misc_feature
<222> LOCATION: (33)..(33)
<223> OTHER INFORMATION: k is either c, g or t
<220> FEATURE:
<221> NAME/KEY: misc_feature
<222> LOCATION: (34)..(35)
<223> OTHER INFORMATION: n is either a, c, g or t
<220> FEATURE:
<221> NAME/KEY: misc_feature
<222> LOCATION: (36)..(36)
<223> OTHER INFORMATION: k is either c, g or t
<220> FEATURE:
<221> NAME/KEY: misc_feature
<222> LOCATION: (37)..(38)
<223> OTHER INFORMATION: n is either a, c, g or t
<220> FEATURE:
<221> NAME/KEY: misc_feature
<222> LOCATION: (39)..(39)
<223> OTHER INFORMATION: k is either c, g or t
<220> FEATURE:
<221> NAME/KEY: misc_feature
```

```
<222> LOCATION: (40)..(41)
<223> OTHER INFORMATION: n is either a, c, g or t
<220> FEATURE:
<221> NAME/KEY: misc_feature
<222> LOCATION: (42)..(42)
<223> OTHER INFORMATION: k is either c, g or t
<220> FEATURE:
<221> NAME/KEY: misc_feature
<222> LOCATION: (43)..(44)
<223> OTHER INFORMATION: n is either a, c, g or t
<220> FEATURE:
<221> NAME/KEY: misc_feature
<222> LOCATION: (45)..(45)
<223> OTHER INFORMATION: k is either c, g or t
<220> FEATURE:
<221> NAME/KEY: misc_feature
<222> LOCATION: (46)..(47)
<223> OTHER INFORMATION: n is either a, c, g or t
<220> FEATURE:
<221> NAME/KEY: misc_feature
<222> LOCATION: (48)..(48)
<223> OTHER INFORMATION: k is either c, g or t
<220> FEATURE:
<221> NAME/KEY: misc_feature
<222> LOCATION: (49)..(50)
<223> OTHER INFORMATION: n is either a, c, g or t
<220> FEATURE:
<221> NAME/KEY: misc_feature
<222> LOCATION: (51)..(51)
<223> OTHER INFORMATION: k is either c, g or t

<400> SEQUENCE: 43
cgaggcatcg ctagctttgt gtgtgagnnk nnknnknnkn nknnknnknn kgaggtccgg      60
gtgacagt                                                              68

<210> SEQ ID NO 44
<211> LENGTH: 59
<212> TYPE: DNA
<213> ORGANISM: Artificial Sequence
<220> FEATURE:
<223> OTHER INFORMATION: Description of Artificial Sequence: Phage
      display reverse primer

<400> SEQUENCE: 44
ggttgccgca cagacttcgg tcacctggct gtcagcctgc cgaagcactg tcacccgga      59

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: CTLA4
      mutant

<400> SEQUENCE: 45

Phe Glu Pro Lys Arg Gly Val Gln
1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: CTLA4
      mutant

<400> SEQUENCE: 46

Trp Asp Gln Tyr Thr Gly Tyr Gly
1               5
```

```
-continued

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: CTLA4
      mutant

<400> SEQUENCE: 47

Trp Asp Ala Tyr Arg Asn Gln Gln
1               5

<210> SEQ ID NO 48
<211> LENGTH: 8
<212> TYPE: PRT
<213> ORGANISM: Artificial Sequence
<220> FEATURE:
<223> OTHER INFORMATION: Description of Artificial Sequence: CTLA4
      mutant

<400> SEQUENCE: 48

Tyr Asp His Pro Tyr Asp Gly Gln
1               5

<210> SEQ ID NO 49
<211> LENGTH: 8
<212> TYPE: PRT
<213> ORGANISM: Artificial Sequence
<220> FEATURE:
<223> OTHER INFORMATION: Description of Artificial Sequence: CTLA4
      mutant

<400> SEQUENCE: 49

Trp Asp Gln His Val Ser Arg Arg
1               5

<210> SEQ ID NO 50
<211> LENGTH: 8
<212> TYPE: PRT
<213> ORGANISM: Artificial Sequence
<220> FEATURE:
<223> OTHER INFORMATION: Description of Artificial Sequence: CTLA4

<400> SEQUENCE: 50

Tyr Ala Ser Pro Gly Lys Ala Thr
1               5
```